(12) United States Patent
Pinchot

(10) Patent No.: US 8,066,955 B2
(45) Date of Patent: Nov. 29, 2011

(54) PROCESSING APPARATUS FABRICATION

(75) Inventor: James M. Pinchot, Parma, OH (US)

(73) Assignee: James M. Pinchot, Cleveland, OH (US)

( * ) Notice: Subject to any disclaimer, the term of this patent is extended or adjusted under 35 U.S.C. 154(b) by 697 days.

(21) Appl. No.: 12/050,334

(22) Filed: Mar. 18, 2008

(65) Prior Publication Data

US 2008/0213141 A1 Sep. 4, 2008

Related U.S. Application Data

(63) Continuation-in-part of application No. 11/247,124, filed on Oct. 11, 2005, which is a continuation of application No. 10/688,233, filed on Oct. 17, 2003, now Pat. No. 6,994,245.

(60) Provisional application No. 60/919,309, filed on Mar. 21, 2007.

(51) Int. Cl.
*B01J 8/02* (2006.01)

(52) U.S. Cl. ........ 422/211; 422/600; 422/601; 422/603; 228/103; 228/252

(58) Field of Classification Search .................. 422/191, 422/211, 600, 601, 603; 228/103, 252; 378/147
See application file for complete search history.

(56) References Cited

U.S. PATENT DOCUMENTS

| | | | |
|---|---|---|---|
| 3,701,619 A | 10/1972 | Appeldoorn | |
| 3,881,701 A | 5/1975 | Schoenman et al. | |
| 3,988,589 A | 10/1976 | Leask | |
| 4,450,706 A | 5/1984 | Engelmohr | |
| 4,516,632 A * | 5/1985 | Swift et al. | 165/167 |
| 4,647,435 A * | 3/1987 | Nonnenmann | 422/180 |
| 4,869,421 A | 9/1989 | Norris et al. | |
| 5,031,483 A | 7/1991 | Weaver | |
| 5,071,503 A | 12/1991 | Berman | |
| 5,137,369 A | 8/1992 | Hodan | |
| 5,250,263 A | 10/1993 | Manz | |
| 5,398,193 A | 3/1995 | DeAngelis | |
| 5,415,715 A * | 5/1995 | Delage et al. | 156/197 |
| 5,514,232 A | 5/1996 | Burns | |
| 5,534,328 A | 7/1996 | Ashmead et al. | |
| 5,544,771 A | 8/1996 | Lee et al. | |
| 5,580,523 A | 12/1996 | Bard | |
| 5,595,712 A | 1/1997 | Harbster et al. | |
| 5,658,537 A | 8/1997 | Dugan | |
| 5,683,828 A | 11/1997 | Spear et al. | |
| 5,690,763 A * | 11/1997 | Ashmead et al. | 156/60 |
| 5,727,618 A | 3/1998 | Mundinger et al. | |
| 5,779,833 A | 7/1998 | Cawley et al. | |

(Continued)

OTHER PUBLICATIONS

A Novel Cross-Fow Microreactor for Kinetic Studies of Catalytic Processes by Sameer K. Ajmera, Cyril Delattre, martin A. Schmidt, and Klavs F. Jensen, MicroChemical Systems, Technology Center.

*Primary Examiner* — Walter D Griffin
*Assistant Examiner* — Huy-Tram Nguyen
(74) *Attorney, Agent, or Firm* — Fay Sharpe LLP; Brian E. Turung

(57) ABSTRACT

A processing apparatus that is formed from a plurality of metal layers that are stacked and aligned together and then connected together to form one or more portions of the processing apparatus.

18 Claims, 27 Drawing Sheets

U.S. PATENT DOCUMENTS

| | | |
|---|---|---|
| 5,843,385 A | 12/1998 | Dugan |
| 5,847,958 A | 12/1998 | Shaikh et al. |
| 5,872,714 A | 2/1999 | Shaikh et al. |
| 5,961,932 A | 10/1999 | Ghosh et al. |
| 5,993,750 A | 11/1999 | Ghosh et al. |
| 6,048,432 A | 4/2000 | Ecer |
| 6,057,481 A | 5/2000 | Brockwell et al. |
| 6,075,840 A | 6/2000 | Pellegrino et al. |
| 6,129,973 A | 10/2000 | Martin et al. |
| 6,167,910 B1 | 1/2001 | Chow |
| 6,185,278 B1 * | 2/2001 | Appleby et al. ............. 378/149 |
| 6,192,596 B1 | 2/2001 | Bennett |
| 6,200,536 B1 | 3/2001 | Tonkovich |
| 6,240,161 B1 | 5/2001 | Siochi |
| 6,271,524 B1 | 8/2001 | Wainer et al. |
| 6,287,436 B1 | 9/2001 | Pelletier et al. |
| 6,324,438 B1 | 11/2001 | Cormier |
| 6,352,577 B1 | 3/2002 | Martin et al. |
| 6,377,661 B1 | 4/2002 | Guru et al. |
| 6,388,816 B2 | 5/2002 | Brown et al. |
| 6,396,902 B2 | 5/2002 | Tybinkowski et al. |
| 6,409,072 B1 | 6/2002 | Breuer et al. |
| 6,484,776 B1 | 11/2002 | Meilunas et al. |
| 6,488,838 B1 | 12/2002 | Tonkovich |
| 6,490,812 B1 | 12/2002 | Bennett et al. |
| 6,494,614 B1 | 12/2002 | Bennett et al. |
| 6,507,642 B2 | 1/2003 | Fujishige et al. |
| 6,526,123 B2 | 2/2003 | Ein-Gal |
| 6,527,890 B1 | 3/2003 | Huang et al. |
| 6,533,840 B2 | 3/2003 | Martin et al. |
| 6,556,657 B1 | 4/2003 | Tybinkowski et al. |
| 6,561,208 B1 | 5/2003 | O'Connor et al. |
| 6,575,218 B1 | 6/2003 | Burns et al. |
| 6,587,742 B2 | 7/2003 | Manuel et al. |
| 6,592,696 B1 | 7/2003 | Burdon et al. |
| 6,643,302 B1 | 11/2003 | Nishikawa et al. |
| 6,645,432 B1 | 11/2003 | Anderson et al. |
| 6,654,656 B2 | 11/2003 | Kesavadas et al. |
| 6,672,502 B1 * | 1/2004 | Paul et al. ..................... 228/164 |
| 6,676,835 B2 | 1/2004 | O'Connor et al. |
| 6,692,700 B2 | 2/2004 | Handique |
| 6,695,044 B1 | 2/2004 | Symonds |
| 6,700,427 B1 | 3/2004 | Sherman |
| 6,729,352 B2 | 5/2004 | O'Connor et al. |
| 6,989,134 B2 | 1/2006 | Tonkovich |
| 7,014,835 B2 | 3/2006 | Mathias |
| 7,220,390 B2 | 5/2007 | Tonkovich |
| 7,288,231 B2 | 10/2007 | Tonkovich |
| 7,455,709 B2 * | 11/2008 | Ohno et al. .................... 55/523 |
| 7,521,025 B2 * | 4/2009 | Ohno et al. ................... 422/168 |
| 2002/0009741 A1 | 1/2002 | Simpson et al. |
| 2002/0048644 A1 | 4/2002 | Han |
| 2002/0106311 A1 | 8/2002 | Golbig et al. |
| 2002/0119079 A1 | 8/2002 | Breuer et al. |
| 2002/0189530 A1 | 12/2002 | David |
| 2002/0195048 A1 | 12/2002 | David |
| 2002/0195052 A1 | 12/2002 | David |
| 2003/0027022 A1 | 2/2003 | Arana et al. |
| 2003/0083410 A1 | 5/2003 | Baur et al. |
| 2003/0091496 A1 | 5/2003 | Resasco et al. |
| 2003/0128812 A1 | 7/2003 | Appleby et al. |
| 2003/0152488 A1 | 8/2003 | Tonkovich et al. |
| 2003/0158410 A1 | 8/2003 | Nickel et al. |
| 2003/0164118 A1 | 9/2003 | Nickel et al. |
| 2003/0180216 A1 | 9/2003 | TeGrotenhuis et al. |
| 2003/0204285 A1 | 10/2003 | Thomas et al. |
| 2003/0204288 A1 | 10/2003 | Thomas et al. |
| 2003/0223909 A1 | 12/2003 | Oberbeck et al. |
| 2003/0235272 A1 * | 12/2003 | Appleby et al. ............. 378/147 |
| 2004/0156478 A1 * | 8/2004 | Appleby et al. ............. 378/147 |
| 2005/0266991 A1 * | 12/2005 | Ohno et al. ................... 502/439 |

* cited by examiner

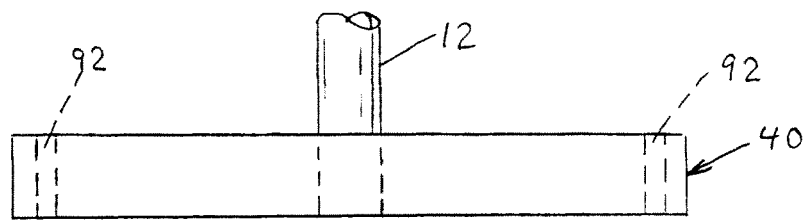
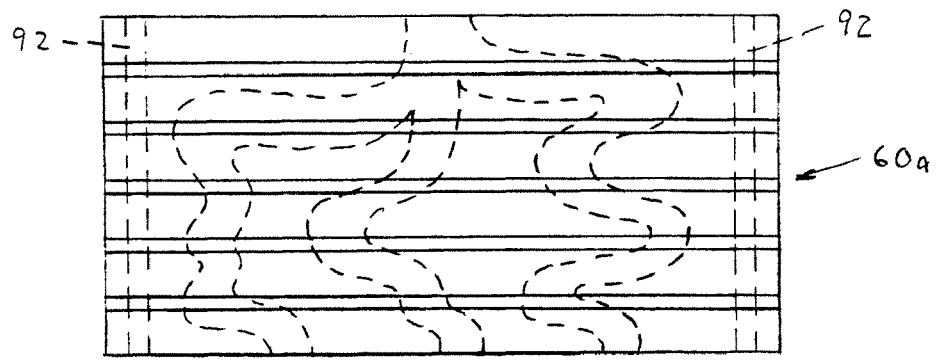
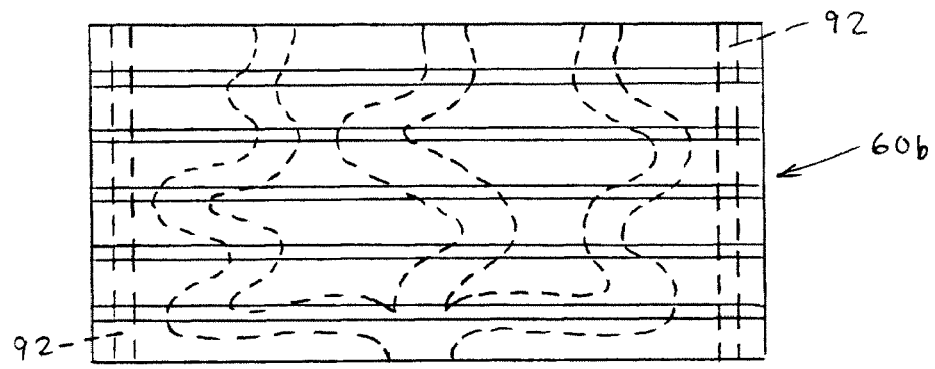
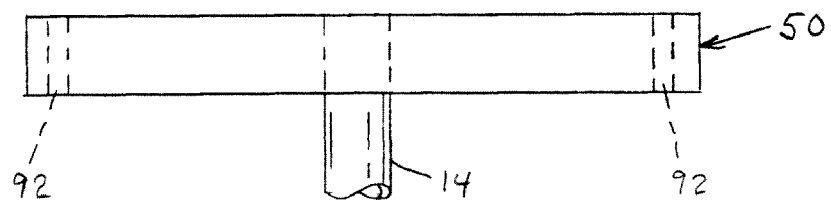
FIG. 4B

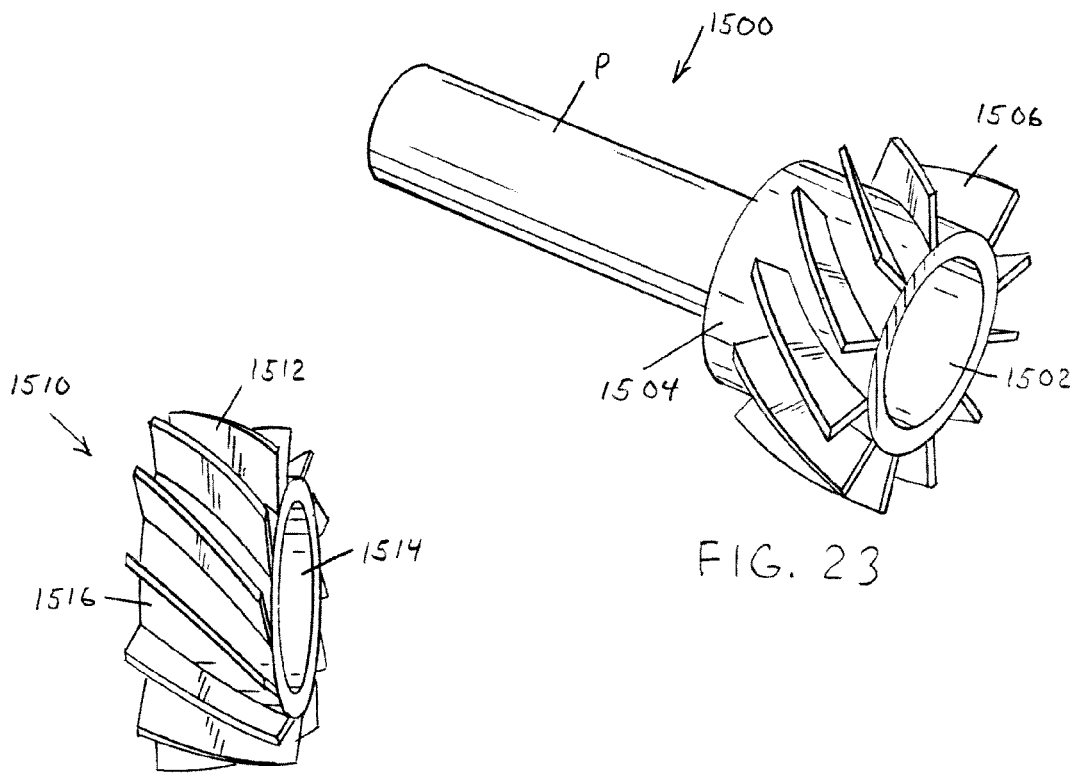
FIG. 23
FIG. 24
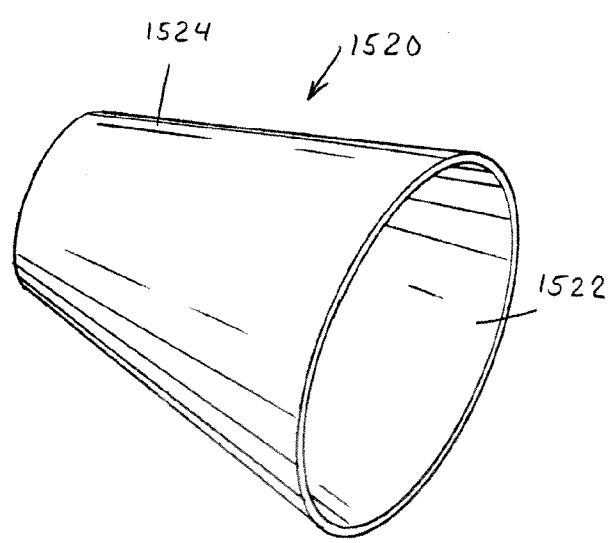
FIG. 25

PROCESSING APPARATUS FABRICATION

The present invention claims priority on U.S. Provisional Application Ser. No. 60/919,309 filed Mar. 21, 2007, which is incorporated herein.

The present invention is a continuation-in-part of U.S. patent application Ser. No. 11/247,124 filed Oct. 11, 2005, which in turn is a continuation of U.S. application Ser. No. 10/688,233 filed Oct. 17, 2003, now U.S. Pat. No. 6,994,245, all of which are incorporated herein by reference.

This invention generally relates to a chemical and/or heat processing apparatus, and more particularly to a chemical and/or heat processing apparatus assembled from layers of materials having specific compositions and/or shapes for used in one or more chemical applications, biological applications, and/or energy applications.

BACKGROUND OF INVENTION

The field of energy, chemistry and biology continues to advance at a rapid pace. New chemical and biological agents are developed daily in laboratory settings. New fuel cells and heat exchangers are also being developed to meet the energy needs of the future. However, conventional processing equipment suffers from a number of disadvantages. It has long been recognized in the chemical industry that "scale up" from laboratory bench-scale to commercial production scale is difficult. Results achieved in the laboratory are often difficult to duplicate at production rates in production facilities. Methods of controlling and optimizing processes for producing such chemical and biological compounds are becoming better understood. The control of parameters such as temperature, pressure, mixing conditions, relative volumes of reactants, and uses of catalysts are also becoming better understood. Traditionally, newly discovered chemical and biological compounds and/or processes involving either the production of such compounds, or processes involving the use of such compounds, have initially been carried out in "bench-scale" environments. Promising chemicals, biological agents, and/or processes are ultimately produced in mass quantity by application to industrial-scale processes. However, problems are often encountered in scaling up the process from the laboratory to industrial-scale production.

Conventional chemical processing equipment typically holds a relatively large volume of materials and consequently has a relatively large volume to surface area ratio. As a result, different portions of the reactant materials contained within such equipment are exposed to different histories of conditions. In the case of a conventional tank reactor, for example, even when temperature conditions at the walls of the reactor are well controlled, the portions of the reactants that are not in close proximity to the walls of the reactor may experience different temperature histories, especially if a significant temperature gradient exists, which might occur if the chemical reaction is strongly exothermic. Rapid stirring of the reactants may reduce this temperature history difference, but will not eliminate it. As a result of the nonhomogeneous temperature history, different portions of the reactants may chemically react differently. Undesired reactions may occur in portions of the reactants that are exposed to histories of higher than desired temperatures. This may result in the production of undesired waste products, which may be hazardous and which must be properly disposed of. In extreme situations reaction rates may accelerate to uncontrollable levels, which may cause safety hazards, such as potential explosions. If, however, the volume to surface area ratio of the processing apparatus is substantially reduced, the degree of precision of control of homogeneity of temperature history of the reactants can be substantially improved.

Other common problems associated with moving from bench-scale production to industrial-scale production involve changes in process conditions between the bench-scale environment and the industrial environment. For instance, the temperature of the reactants in a beaker or flask in a laboratory is easier to keep constant than the temperature in a production tank having a capacity of hundreds of gallons, as is often the case in a chemical processing plant. In addition, high pressures and temperatures are easier to maintain in small laboratory sized vessels than in much larger vessels used for production scale operation. In many instances, it is cost prohibitive or not feasible to scale up a reaction vessel from a bench-scale environment to industrial-scale processes. Variations in other process conditions within a large tank are also more difficult to control, and frequently affect the quality and yield of the desired product.

Another aspect of laboratory development of processes to produce chemical or biological compounds is that often potentially dangerous chemicals are used to create the desired product. Fires and explosions in research laboratories and contaminant injury to personnel and property are well-known risks, especially in the chemical research industry. The risks are not limited only to research, since industrial chemical or biological production facilities also may experience fires and explosions related to chemical production using dangerous chemicals. Often, due to the quantities of chemicals used in industrial-scale processes, such accidents are significantly more devastating in an industrial setting than similar accidents in a research setting.

The materials of construction of conventional chemical processing apparatus, such as steel and specialty iron alloys, furthermore may be subject to corrosion and wear, may have undesirable effects on catalytic activity, or may "poison" a catalyst.

It has been recognized that a high degree of flow turbulence enhances the ability to rapidly mix two or more reactants together. Rapid mixing is important for fast-acting chemical reactions. A high degree of turbulence is also known to enhance heat transfer. Thus, a structure having both a low volume to surface area ratio and a high degree of flow turbulence can be particularly advantageous for precise control of certain types of chemical processing.

Recently, increased attention has been directed to the use of micro-reactors for both development and production of chemical and biological processes. These types of reactors offer several advantages. As stated above, the control of chemical processes within very small reactors is typically easier than the control of a similar process in a large-scale production tank. Once a reaction process has been developed and optimized in a micro-reactor, it can be scaled up to industrial production level by replicating the micro-reactors in sufficient quantity to achieve the required production output of the process. If such reactors can be fabricated in quantity, and for a modest cost, industrial quantities of a desired product can be manufactured with a capital expenditure equal to or even less than that of a traditional chemical production facility. An additional benefit is that because the volume of material in each individual reactor is small, the effect of an explosion or fire is minimized, and with proper design, an accident in one reactor can be prevented from propagating to other reactors.

The use of micro-reactors has also resulted in an increase in safety in laboratory settings. In the research setting, the use of micro-reactors generally results in less exposure to hazardous substances and conditions by research personnel than when using traditional "batch chemistry" equipment, which equipment typically requires the researcher to physically handle chemicals in a variety of glass containers, often in the presence of a heat source. An accident in such an environment is likely to increase the risk of exposure to hazardous chemicals, and cause damage to the laboratory. However, when using a micro-reactor, the micro-reactor is typically a self-contained unit that minimizes the researcher's potential exposure to chemical substances. When using a micro-reactor, the researcher is not required to physically manipulate containers of chemical materials to carry out a desired reaction. As such, the micro-reactor can be located in an area that will protect the researcher from an accident that could result in a fire or explosion.

Another area in which micro-reactors offer an advantage over conventional chemical process development and production is in the mixing of reactants. A mixing channel of the proper scale encourages a laminar flow of the reactants within the channel and is readily achievable in a micro-reactor. Laminar flow can enhance mixing by diffusion, which can eliminate the need to expend energy to physically stir or agitate the reactants.

Micro reactors are particularly applicable to the pharmaceutical industry, which engages in chemical research on many new chemical compounds every year, in the effort to find drugs or chemical compounds with desirable and commercially valuable properties. Enhancing the safety and efficiency of such research is valuable. When coupled with the potential that micro-reactors can eliminate the problems of moving from bench-scale production to industrial production, it is apparent that a micro-reactor suitable for use in carrying out a variety of chemical processes, and having an efficient and low-cost design is desirable.

Several different designs for micro-reactors have been developed. Some of these designs are disclosed in U.S. Pat. Nos. 3,701,619; 5,534,328; 5,580,523; 5,690,763; 5,961,932; 6,192,596; 6,200,536; 6,490,812; 6,488,838; 6,989,134; 7,000,427; 7,014,835; and 7,220,390; 7,288,231; and U.S. patent application Nos. 2002/0106311 published Aug. 8, 2002; 2002/0048644 published Apr. 25, 2002; and 2003/0091496 published May 15, 2003. All of these patents and patent applications are incorporated herein by reference for teachings concerning reactors, materials used to manufacture the reactors, techniques used to manufacture the reactors, and catalysts used in association with the reactors.

One example of a micro-reactor is disclosed in U.S. Pat. Nos. 5,534,328 and 5,690,763, both of which are incorporated herein by reference. These two patents describe reactor structures for chemical manufacturing and production, fabricated from a plurality of interconnected layers. Generally, each layer has at least one channel or groove formed in it and most include orifices that serve to connect one layer in fluid communication with another. These layers are preferably made from silicon wafers, because silicon is relatively inert to the chemicals that may be processed in the reactor, and because the techniques required to mass produce silicon wafers that have had the required channels and other features etched into their surfaces are well known. A disadvantage of the micro-reactors described in the two patents stems from the rather expensive and complicated process required for manufacturing the devices. While silicon wafer technology has advanced to the state that wafers having desired surface features can readily be mass produced, the equipment required is capital intensive, and unless unit production is extremely high, the substantial costs are difficult to offset. While the two patents suggest that other materials can be used to fabricate the layers, such as metal, glass, or plastic, the surface features required (grooves, channels, etc.) must still be formed in the selected material. The specific surface features taught by the two patents require significant manufacturing steps to fabricate. For instance, while forming an opening through a material is relatively easy, forming a groove or channel that penetrates only part way through the material comprising a layer is more difficult, as the manufacturing process must not only control the size of the surface feature, but the depth as well. When forming an opening that completely penetrates through a material comprising a layer, depth control does not need to be so precisely controlled. The two patents teach that both openings which completely penetrate the layers, and surface features (grooves/channels) that do not completely penetrate the individual layers are required. Hence, multiple processing steps must be employed in the fabrication of each layer, regardless of the material selected.

U.S. Pat. No. 5,580,523, which is incorporated herein by reference, describes a modular micro-reactor that includes a series of modules connected in fluid communication, each module having a particular function (fluid flow handling and control, mixing, chemical processing, chemical separation, etc.). The patent teaches that the plurality of modules are mounted laterally on a support structure, and not stacked. In a preferred embodiment of the invention, silicon wafer technology is again used to etch channels and/or other features into the surface of a silicon wafer. Other disclosed fabrication techniques include injection molding, casting, and micro-machining of metals and semiconductor substrates. Again, the processing required to fabricate the individual modules goes beyond merely forming a plurality of openings into each component. Furthermore, the lateral layout of the reactor described in the patent requires a larger footprint (Basis Area) than a stacked plate reactor. The reactor requires more modules, thus a larger footprint of the entire reactor is required. In contrast, when additional plates are added to a stacked plate reactor, the footprint of the reactor does not change, which can be a distinct advantage, as in many work environments, the area an apparatus occupies on a workbench or floor is more valuable than the vertical height of the apparatus. As such, the disclosed reactor does not minimize the footprints and still does not provide flexibility to add components to customize the reactor for a particular process or application.

U.S. Pat. No. 5,961,932, which is incorporated herein by reference, discloses a reactor that is formed from a plurality of ceramic layers, which are connected in fluid communication, and wherein at least one layer includes a permeable partition. In the preferred embodiment, the patent describes that channels and passageways are formed in each layer. The particular process involves fabricating the layers from "green" or uncured ceramic, which once shaped as desired, must be sintered. The sintering process changes the size of the ceramic layer so that the sizes of the features formed into the ceramic layer in the initial stages of production are different from the finished product. One problem with this reactor design is that the dimensions of the individual components cannot be rigidly controlled during fabrication since the components shrink. Such shrinkage can negatively affect the dimensions of the finished reactor. As such, precise dimensional control of fluid pathways in the reactor are difficult to maintain to achieve the desired flow rates through the reactor.

In U.S. patent application No. 2002/0106311 published Aug. 8, 2002 entitled "Enhancing Fluid Flow in a Stacked Plate Microreactor," which is incorporated herein by reference, a stacked plate chemical reactor in which simple plates are stacked together to form the reactor is disclosed. The stacked plates include openings that define fluid pathways and processing volumes within the stacked plates. In a preferred embodiment, an n-fold internal array is achieved by providing a first group of simple plates defining a reaction unit that includes bypass fluid channels and reaction fluid channels for each reactant, such that a portion of each reactant is directed to subsequent groups of simple plates defining additional reaction units. A chemical reactor with variable output is obtained by reversibly joining reactor stacks comprising irreversibly joined reaction units, these reaction units consisting of a plurality of simple plates. Other embodiments disclosed in the patent application employ at least one of the arrays of parallel fluid channels having different widths, bifurcated fluid distribution channels to achieve a substantially even flow equipartition for fluids with varying viscosities flowing within the fluid channels of each reaction unit.

In several of the prior art reactors identified above, relatively complicated manufacturing techniques are required. The manufacture of layers of silicon material requires a large capital investment. Sintering of a ceramic material requires the precise control of the shrinkage process, or individual components of a desired size cannot be achieved. In all cases, these reactors require complicated structures (for example, fluid channels and reaction channels) to be etched or otherwise fabricated in each layer. Additionally, orifices or passages also need to be formed in each layer, so that fluids can move between adjacent layers of the reactor. Thus, a series of different manufacturing steps typically must be performed for each layer. As such, it is desirable to provide a reactor design offering the advantages described above, which is relatively simple to manufacture, so as to minimize capital investment in scaling up production from the laboratory to the industrial production levels.

While a single micro-reactor can produce only a limited volume of product, additional micro-reactors can be added in parallel to increase production capacity. When additional modular micro-reactor units are added, additional systems for reactant supply, heat transfer media supply, and product collection are typically required, which not only increase the complexity of the system, but also require more space for duplicative fluid systems. Furthermore, even minor differences in feed rates for some of the duplicate reactor modules can negatively affect product quality. Finally, more sophisticated control and monitoring are required to manage additional reaction modules and feed systems. It would therefore be desirable to provide a micro-reactor capable of n-fold parallelization without requiring that additional fluid and control systems be provided.

In an array of identical fluid channels having a single common reactant distribution channel and a single common product collection channel, with the reactant inlet and the product outlet located at opposite ends, where the common reactant distribution and the common product collection channel have the same cross sectional area, if the viscosity of the product relative to the reactants is substantially the same, then the pressure drop through the array can be considered the same, and the resulting flow distribution is fairly even, with only slightly lower flow rates in the central fluid channels. However, the flow distribution through such an array is not even if the viscosity of the product is significantly different from the viscosities of the reactants. When such an array is employed to process a reaction whose product has a significantly different viscosity compared to the viscosity of the mixture of the nonreacted reactants, broad residence time distributions result in the array due to the fact that the pressure drop in the common reactant distribution channel no longer balances with the pressure drop in the common product collection channel. The flow rates within each individual fluid channel in the array are no longer identical. If the viscosity of the product is significantly greater than the viscosity of the mixed but nonreacted reactants, then the flow rates in the individual fluid channels in the array tend to increase across the array for channels closest to the common product outlet. Thus the highest flow rate is experienced in the fluid channel in the array that is closest to the common product outlet, while the lowest flow rate is experienced in the fluid channel in the array that is located furthest from the common product outlet. This phenomenon is different if the viscosity of the product is less than the viscosity of the mixed but nonreacted reactants. Thus for lower viscosity products, the highest flow rate is experienced in the fluid channel in the array that is closest to the common reactant inlet, while the lowest flow rate is experienced in the fluid channel in the array that is located furthest from the common reactant inlet. The greater the relative change in viscosity the greater the variation in flow rates across the array. This imbalance leads to different residence times being associated with different fluid channels, resulting in an undesirable residence time distribution within the whole reaction unit. In certain cases, the additional residence time can lead to undesired cross reactions, and even clogging of the "slowest" fluid channels. As such, it is desirable to provide a micro-reactor including a plurality of fluid channels that is capable of processing reactant mixtures undergoing a significant viscosity change without the above-described residence time distributions and related problems.

For the specific residence time distributions discussed above, relative to reactant mixtures produced in fluid channels in which a plurality of different reactants are mixed, only one type of undesirable residence time distribution is of concern. Residence time distribution problems of this type can also arise in fluid channels used to direct reactants before mixing, as well as products for collection. It is desirable to provide a micro-reactor that includes a plurality of fluid channels adapted to provide substantially equal residence time distributions for fluid flow within the micro-reactor.

Computer modeling of reactors has increased in popularity due to increased computer processing power and increased sophistication in modeling software. As such, reactors are commonly modeled to have increased complexity (e.g., various passageway configurations for increased reactor residence time; passageway configurations to maintained desired flow patterns, temperature profiles, pressure profiles, etc.). These complex reactor designs are difficult, if not impossible, to manufacture and/or are cost prohibitive to manufacture by use of prior art reactor design techniques. Many chemical manufacturing processes also require exposure to catalytic materials to complete the chemical process. Precious metals such as gold, platinum, palladium, iridium, rhodium, silver and the like are used as catalysts in various chemical reactions. In the past, separate reactors had to be produced that contained each different catalyst material. The use of a plurality of reactors resulted in an increase in cost and complexity of a chemical reactor system.

In the energy area, fuel cells are gaining in popularity. Many different fuel cell concepts have been developed; however, particle applications of some of the fuel cell concepts has been impaired due to the complex designs of such fuel cells. Examples of various prior art fuel cells that can be improved by the present invention are illustrated in U.S. Pat. Nos. 3,839,091; 3,959,094; 4,373,109; 4,474,652; 4,609,441; 4,673,473; 4,861,965; 4,972,064; 5,148,001; 5,376,470; 5,492,777; 5,599,638; 5,599,638; 5,656,388; 5,773,162; 5,795,496; 5,888,665; 5,928,806; 5,961,863 and 6,653,596; and PCT patent applications WO 98/22989; WO 98/45694; WO 99/16137; and WO 99/39841 all of which are incorporated herein by reference.

In view of the current state of the art, there is a need for a processing apparatus that can be economically manufactured, can incorporate unique and sophisticated flow patters through the apparatus, and can be design to withstand very low and/or very high temperatures and/or pressure when such temperatures and/or pressure are required. When the processing apparatus is designed for use as a reactor or micro-reactor, there is also a need for a reactor or micro-reactor that can maintain a desired relatively narrow temperature range for a process when desired, has a relatively modest footprint when desired, can provide desired diffusion mixing, can process reaction mixtures that form a product with different viscosities when required, can provide desired residence time distributions for fluid flow within the micro-reactor, and/or can include different types of catalytic materials.

SUMMARY OF THE INVENTION

The present invention pertains to a processing apparatus and method for manufacturing processing apparatus. The processing apparatus of the present invention is particularly suited for use in the reaction of specialty chemicals for the pharmaceutical industry, and will be described with particular reference thereto; however, the invention has much broader applications and the processing apparatus in accordance with the present invention can be used in association with a wide variety of chemical reactions in the chemical, biological, food, and/or pharmaceutical industry, and/or can be used in other or additional applications. The processing apparatus of the present invention could also or alternatively be used in applications that involve a) the production of energy (e.g., fuel cells [e.g., direct oxidation fuel cell, reformer fuel cell, etc.], solar cells, automotive fuel production from natural gas (e.g., Fischer-Tropsch process, etc.), methane processing, methanol production (e.g., methanol from carbon dioxide and hydrogen, etc.), production of alcohols from natural gas (e.g., methanol, ethanol, etc.), coal gasification processes, hydrogenation processes, etc.), b) propulsion systems (e.g., rocket engines, etc.); c) environmental waste processing (e.g., pollution and/or waste control systems, landfill gas processing, methanol production from $CO_2$, reduction of $NO_x$ and/or $SO_x$ gasses, reduction of bio-waste, water purification systems, emissions control [e.g., $CO_2$ sequestering, etc.], etc.); d) biomedical applications (e.g., enzyme production, etc.), heat exchange application (e.g., furnaces, etc.); and/or f) MEMS technology, etc. The applications listed above are merely a few non-limiting examples of applications that the processing apparatus of the present invention can be used. It will be appreciated that the processing apparatus of the invention can include one or more passageways that enable fluids and/or solids to at least partially flow through the processing apparatus. As such, the present invention encompasses any type of reactor, vessel, etc. that includes one or more passageways that are at least partially formed by the novel method and process described in this invention. In the specialty chemical industry (e.g., the pharmaceutical industry), relatively small amounts of chemical compounds are manufactured; however, larger reactor vessels are typically used to form these chemicals. Consequently, it is not uncommon for a reactor vessel to be running at 30% or less capacity. During the manufacture of many types of specialty chemicals or pharmaceutical agents, catalysts are commonly used to promote the reaction of the chemicals. Commonly, one or more precious metals such as, but not limited to, gold, platinum, palladium, iridium, rhodium, ruthenium, and/or silver, are used as catalysts. As can be appreciated, other or additional types of metal or nonmetal materials can be used as a catalyst to form the specialty chemical or pharmaceutical agent or other type of product (e.g., cobalt, copper, copper-chromium, copper-alumina, iridium, lead, molybdenum, nickel, osmium, palladium, platinum, rhodium, ruthenium, silver, silver oxide, vanadium, zinc, zinc-chromium oxide, etc.). As can also be appreciated, when the processing apparatus is used to form other types of material (e.g., methanol from natural gas, methanol from carbon dioxide, etc.) and/or is used in other types of applications (e.g., fuel cells, removal of undesired gasses, etc.), the catalyst may or may not include a precious metal. For example, anodized aluminum can be used to promote the conversion of natural gas into methanol. The present invention also encompasses these non-limiting types of applications mention above. In prior art reactors that included a precious metal as a catalyst, each different precious metal that was used as a catalyst was typically placed in a separate reactor so that the precious metal could be later recovered after the catalyst had been at least partially spent. The use of one or more catalysts, each of which were placed in a large reactor vessel, commonly resulted in a large capital expenditure on equipment that was only partially used for the formation of a particular chemical. In addition to the inefficient use of large reactor vessels during the manufacture of specialty chemicals, the use of large reactor vessels makes it difficult to maintain and/or control the required reaction parameters (e.g., reaction temperature, pressure, mixing rates, flow rates, etc.). The processing apparatus of the present invention is designed to overcome these shortcomings of past reactors. The processing apparatus of the present invention can have a modular design; however, this is not required. This modular design, when used, can take many forms. In one non-limiting modular design, the processing apparatus has a top or front portion, a middle portion, and a bottom or back portion; however, this is not required. The top or front portion of the processing apparatus can be designed to be secured to one or more pipes, tubes or the like that feed the reactants to the processing apparatus; however, this is not required. As can be appreciated, one or more reactants can also or alternatively be feed into the processing apparatus at the middle portion and/or the bottom or back portion of the processing apparatus; however, this is not required. As can be appreciated, the reactants are typically in liquid and/or gas form; however, solid reactants and/or some combination of solid, liquid and/or gas can be used. The bottom or back portion of the processing apparatus can be designed to be secured to one or more pipes, tubes or the like that direct the reacted reactants from the processing apparatus; however, this is not required. As can be appreciated, one or more reacted reactants can also or alternatively be removed from the processing apparatus at the middle portion and/or the top or front portion of the processing apparatus; however, this is not required. Typically the top or front portion and bottom or back portion of the processing apparatus do not contain a catalyst when a catalyst is used in the processing apparatus; however, a catalyst can be positioned in and/or be formed in the top or front portion and/or bottom or back portion of the processing apparatus if so desired. Typically the top or front portion and bottom or back portion of the processing apparatus are made of similar materials; however, this is not required. The middle portion of the processing apparatus typically includes one or more catalysts, when a catalyst is used in the processing apparatus; however this is not required. Although the processing apparatus has been described as having one or more reactants that are directed into the processing apparatus, it can be appreciated that some or all of the materials directed into the processing apparatus may not change in chemical composition as the materials pass through the processing apparatus. For instance, a portion or all of the processing apparatus can be designed as a heat exchanger. In such a configuration, the one or more materials passing into the processing apparatus can be used to solely transfer heat to another material in and/or about the processing apparatus. In one non-limiting example, the processing apparatus is designed to enable heating and/or cooling fluids (e.g., water, glycol, etc.) at least partially passed into the processing apparatus to absorb heat and/or radiate heat as the heating and/or cooling fluids pass into and at least partially through the heating and/or cooling fluids. In one non-limiting configuration, the heating and/or cooling fluids could be used has a component of a furnace wherein heat from the combustion of gas is at least partially transferred to another fluid flowing in the processing apparatus and/or to another fluid flowing about the processing apparatus. As can be appreciated, the combustion of gas can occur at least partially outside of and/or inside the processing apparatus.

In one non-limiting aspect of the present invention, the processing apparatus has a modular design. The modular design of processing apparatus enables the components of the processing apparatus to be better customized for a particular application. For instance, if a processing apparatus was required to handle a flow rate of A liters and be exposed to a catalyst B for a period of time C, a top or front portion and a bottom or back portion of the processing apparatus could be selected to handle flow rate A and a middle portion that includes or is made of catalyst B and having a sufficient surface area to achieve a time of exposure C would be selected. Alternatively or additionally, if a processing apparatus was required to handle a flow rate of A liters and needed to be resident in the processing apparatus for a period of time C, a top or front portion and a bottom or back portion of the processing apparatus could be selected to handle flow rate A and a middle portion that included enough passageways and passageway lengths in combination with the passageways and passageway lengths of the top or front portion and a bottom or back portion would be selected to provide the desired residence time. These three components could then be secured together to form at least a portion of the processing apparatus. If however, a processing apparatus was required to handle a flow rate of A liters and be exposed to a catalyst D for a period of time E and, or a different residence time in the processing apparatus was required, the same top or font portion and a bottom or back portion used in the previous processing apparatus could be used and a different middle portion that includes or is made of catalyst D and having a sufficient surface area to achieve a time of exposure E and/or a different middle portion that included the needed passageways and passageway lengths would then be selected. As such, the modular design of the processing apparatus can be used to increase the versatility of uses for the processing apparatus. In one non-limiting embodiment of the invention, the top or front portion and/or the bottom or back portion of the processing apparatus can be standardized for broad flow rate ranges and the middle portion can be customized to achieve the desired flow rate and/or resident times in the middle portion; however, this is not required. In this particular non-limiting embodiment, the number of different components for the top or front portion and the bottom or back portion can be reduced so as to reduce the cost of the modular processing apparatus. For instance, three sets of top or front portions and bottom or back portions could be used wherein set A can handle liquid flow rates of up to 1 liter per minute, set B can handle liquid flow rates of up to 10 liters per minute, and set C can handle liquid flow rates of up to 100 liters per minute. As can be appreciated, these are merely exemplary flow rate ratings and the one of more sets can have different flow rate ratings. Continuing with the example, if a processing apparatus was to be used to handle liquid flow rates of 15-25 liters per minute, set B would be selected for use in the processing apparatus and a custom middle portion would then be selected that includes passage sizes that would limit the flow rate of liquid through the middle portion to about 25 liters per minute. In another example, if a processing apparatus was to be used to handle liquid flow rates of 50-75 liters per minute, set B would again be selected for use in the processing apparatus and a custom middle portion would then be selected that includes passage sizes that would limit the flow rate of liquid through the middle portion to about 75 liters per minute. In still another example, if a processing apparatus was to be used to handle liquid flow rates of 0.5 liters per minute, set A would be selected for use in the processing apparatus and a custom middle portion would then be selected that includes passage sizes that would limit the flow rate of liquid through the middle portion to about 0.5 liters per minute. As can be appreciated from these examples, a few standard sets of top or front portions and bottom or back portions can be manufactured for use in a wide variety of processing apparatus designs.

In still another and/or alternative non-limiting aspect of the present invention, the size and shape of one or more passageways in one or more of the portions of the processing apparatus can be selected to achieve a) a desire flow profile (e.g., laminar flow, turbulent flow, etc.) of the materials through the one or more passageways, b) a desired residence time of the materials in the one or more passageways, c) a desired amount of surface area contact between the materials flowing through the one or more passageways and the walls and/or surface features of the one or more passageways, d) the desired amount of throughput through the reactor, e) the desired mount of heat transfer to or from the one or more material flowing in and/or about the processing apparatus, and/or f) the desired temperature and/or pressure of the one or more materials in the processing apparatus. The type of flow profile can be used to affect the mixing rates of the materials in the processing apparatus and/or reaction rate of one or more materials in the processing apparatus. The number of passageways, the size of the passageways at various points along the length of the passageway, and/or the shape (e.g., circular-shaped, oval-shaped, triangular-shaped, diamond-shaped, cone-shaped, square-shaped, rectangular-shaped, other polygonal shapes, etc.) of the passageway can be selected to achieve a desired flow profile for the materials pass through the passageways, obtain the desired surface area exposure to the materials passing through the passageways, obtain the desired pressure drop in the passageways, and/or minimize pressure drop in the passageways. For instance, it has been found in some applications that a triangular shaped passageway can be used to increase flow rates through the passageways, minimize pressure drop as materials pass through the passageways, and in some instances increase the exposure of the walls of the passageways to the materials passing through the passageways. Generally, the maximum diameter or cross-sectional width of the one or more passageways is at least about 0.01 µm, typically at least about 5 µm, and more typically at least about 10 µm. The upper limit of the maximum diameter or cross-sectional width of the one or more passageways is non-limiting and will generally depend of the use and configuration of the processing apparatus. Typically the upper limit of the maximum diameter or cross-sectional width of the one or more passageways is about 500,000 µm, typically up to about 50,000 µm, and more typically up to about 10,000 µm; however, other sizes can be used. For micro-reactor applications, the maximum diameter or cross-sectional width of one or more portions of the one or more passageways is generally up to about 5000 μm, and typically up to about 2000 μm; however, other sizes can be used. As can be appreciated, the maximum diameter or cross-sectional width of at least one passageway and/or shape of at least one passageway can be varied along the length of such passageway. The cross-sectional area and/or cross-sectional shape of the one or more passageways can be constant or varied along the length of the one or more passageways in the processing apparatus. The walls of the one or more passageways can be generally smooth or not be smooth. Smooth wall surfaces are generally more conducive in promoting laminar flow through the passageway. Non-smooth wall surfaces generally are more conducive in promoting non-laminar flow through the passageway. As such, the wall profile of the one or more passageways can be selected to promote the desired type of flow through the one or more passageways. In addition or alternatively, the wall profile of the one or more passageways can be selected to achieve the desired about of surface area exposure of the walls of the one or more passageways to the materials that are flowing through the one or more passageways. The control of surface area exposure can be used to control reaction rates and/or other changes to the materials that pass through one or more passageways in the reactor. As can be appreciated, the configuration of one or more portions of one or more passageways in the processing apparatus can be designed so as to partially simulate an environment of one or more material flowing through a traditional bed or mesh, catalyst, etc. The design and complexity of the passageways in the processing apparatus are not limiting to the present invention. In other words, nearly any passageway design and configuration can be made by the method and process of manufacture of the processing apparatus in accordance with the present invention.

In yet another and/or alternative non-limiting aspect of the present invention, the top or front portion and bottom or back portion of the processing apparatus are generally made of a durable material; however, this is not required. The materials can be selected to be non-reactive with the materials passing through the micro-reactor; however, this is not required. The materials can also be selected to handle the temperatures and pressures of the materials passing through the processing apparatus, and/or assist in desired heat transfer rates in one or more portions of the processing apparatus however, this is not required. As can be appreciated, the top or front portion and bottom or back portion of the processing apparatus can be formed of the same or different materials. As can also be appreciated, the top or front portion and/or bottom or back portion of the processing apparatus can be formed of one material or formed of multiple materials. In one non-limiting embodiment of the invention, the materials that can be used to form the top and/or bottom portions include, but are not limited to, crystalline materials, ceramics, glasses, polymers, composite materials, and/or metals. In another and/or alternative non-limiting embodiment of the invention, the top or front portion and/or bottom or back portion of the processing apparatus can be made of one or more metals such as, but not limited to, stainless steel, copper, copper alloys, carbon steel, nickel, nickel alloys, titanium, titanium alloys, aluminum, and aluminum alloys. As can be appreciated, other or additional materials can be used. Although the processing apparatus has been described above to have three portions, namely a top, bottom and middle portions, it will be appreciated that the processing apparatus can be formed of only one or two portions, or be formed or more than three portions. As can also be appreciated, these various portions can include one or more of the materials and/or configurations discussed in this invention with regard to the top, bottom and/or middle portions of the processing apparatus.

In still another and/or alternative non-limiting aspect of the present invention, one or more portions of the processing apparatus can include one or more catalysts. In many chemical reactions, a catalyst is required to promote the reaction of one or more reactants. In systems that require a catalyst, the processing apparatus includes one or more catalysts. As can be appreciated, in systems that do not require a catalyst, the processing apparatus generally does not include one or more catalysts. Typically the catalyst, when used, is located in the middle portion of the processing apparatus; however, the catalyst can be located in other or additional locations in the processing apparatus. The one or more catalyst used in the processing apparatus can form part of the walls of the one or more passageways in the reactor and/or be inserted in one or more passageways of the processing apparatus. The inserted catalyst can take many different forms such as, but not limited to, traditionally shaped catalyst inserted in a portion of one or more passageways, a shell or tube of catalyst inserted in a portion of one or more passageways, etc. In one non-limiting embodiment of the invention, the processing apparatus includes a single catalyst in one or more portions of the processing apparatus. The catalyst can be formed on and/or as part of the processing apparatus (e.g., one or more materials used to form a portion of the processing apparatus also functions as a catalyst; the catalyst is coated, plated, anodized, etc. at least partially in one or more passageways in the processing apparatus, etc.) and/or inserted in one or more regions of the processing apparatus (e.g., mesh of catalyst positioned in one or more passageways in the processing apparatus, beads and/or particles of catalyst positioned in one or more passageways in the processing apparatus, etc.). In another and/or additional non-limiting embodiment of the invention, the processing apparatus can include a plurality of catalysts in one or more portions of the processing apparatus. When more than one catalyst is used, the catalyst can be located in the same and/or different regions in the processing apparatus. In one non-limiting aspect of this embodiment, the catalyst can be attached to and/or formed on the wall of one or more passageways in one or more portions of the processing apparatus. In one specific non-limiting example, at least a portion of the walls of one or more passageways include one or more catalysts. In another and/or alternative non-limiting aspect of this embodiment, two catalysts are attached to or formed on at least a portion of the wall of one or more passageways in one or more portions of the processing apparatus. In one specific non-limiting example, one portion of the walls of the passageways includes one catalyst and another portion of the walls of the passageways includes the other catalyst. As can be appreciated, many various configurations of catalyst in the processing apparatus can be used, and all of these various combinations are included in the present invention.

In yet another and/or alternative non-limiting aspect of the present invention, one or more portions of the processing apparatus can include one or more passageways that can be used to at least partially facilitate in the desired reaction of the chemical reactants, when a reaction of one or more reactants is to at least partially occur in the processing apparatus. Various parameters can be used to control a chemical reaction. Such parameters include, but are not limited to, temperature, pressure, flow rate, flow profile (e.g., turbulent flow, laminar flow, etc.), type of catalyst, time of exposure to catalyst, and/or surface area of catalyst exposure. The size of the passageways through the one or more portions of the processing apparatus can be selected to affect the flow rate, flow profile and/or pressure of the material as the materials pass through the one or portions of the processing apparatus. The length and/or configuration of the passageways can be selected to obtain the amount of time of catalyst exposure to the materials passing through the processing apparatus, especially when the passageways include the catalyst.

In still yet another and/or alternative non-limiting aspect of the present invention, the processing apparatus can include one or more materials and/or one or more passageways to obtain a desired temperature profile and/or heat exchange properties for the processing apparatus. One or more portions of the processing apparatus can include one or more materials and/or one or more passageways to facilitate in heat transfer between 1) one or more portions of the processing apparatus, 2) the processing apparatus and fluid and/or material positioned about and/or flowing about one or more portions of the processing apparatus, and/or 3) the processing apparatus and one or more other processing apparatuses and/or other devices adjacently positioned to the processing apparatus. The one or more materials used in the processing apparatus and/or the one or more passageways in the processing apparatus can be used to at least partially regulate the temperature of 1) one or more of the materials flowing at least partially though the processing apparatus, 2) one or more materials positioned about and/or flowing about the processing apparatus, and/or 3) one or more other processing apparatuses and/or other devices adjacently positioned to the processing apparatus. Alternatively or additionally, one or more heating elements (e.g., heating coil, etc.) can be incorporated in one or more of the portions of the processing apparatus to regulate the temperature of one or more of the materials in the processing apparatus. For example, when one or more reactions are to occur in the processing apparatus, the temperature of one or more reactants in the processing apparatus can be at least partially controlled and/or the heat of reaction can be at least partially controlled to achieve the desired reaction and/or rate of reaction in the processing apparatus.

In another non-limiting example, when the processing apparatus is used at least partially as a heat exchanger, the materials or the processing apparatus; the number and/or size of the passageways in the processing apparatus; and/or the proximity of one or more passageways to one another in the processing apparatus can be used to achieve the desired heat exchange properties of the processing apparatus with relation to materials flowing in the processing apparatus and/or about the processing apparatus. One or more temperature sensors can be incorporated in one or more of the portions of the processing apparatus to facilitate in the control of the temperature in the processing apparatus, and/or to monitor one or more portions of the processing apparatus; however, this is not required.

In a further and/or alternative non-limiting aspect of the present invention, when the processing apparatus has a modular design, one or more portions of the processing apparatus can be designed so that one or more portions can be connected together in a manner that allows for later disconnection. The separation of one or more portions of the processing apparatus is advantageous when one or more portions of an unused module can be used to form another processing apparatus. As such, one or more portions of the processing apparatus can be recycled and reused in other processing apparatus, thereby reducing waste and extending the life of one or more portions of the processing apparatus. The separation of the portions of the processing apparatus is also advantageous when the spent or partially spent catalyst in one or more portions of the processing apparatus is to be recovered, when one or more portions include a catalyst. When valuable or precious metals are used as the catalyst, the recovery of such metals is desirable. In the past, the full reactor that included the catalyst was melted down in order to recover the desired metal catalyst. The processing apparatus of the present invention can be designed such that one or more portions of the processing apparatus include the catalyst, the processing apparatus can be separated so as to facilitate in the recovery and/or replacement of the catalyst. As such, when the processing apparatus is taken out of service, the processing apparatus can be taken apart and the portion containing the catalyst can be removed for recovery of the catalyst. If the processing apparatus includes two or more different catalysts, the portions containing the different catalyst can be separated and then processed in separate recovery processes thereby minimizing contamination of the recovered catalyst. In prior micro-reactor designs, different catalysts were not placed in the same reactor since during recovery of the catalyst, which was typically accomplished by melting the catalyst, the inclusion of two or more catalysts would result in the contamination of the catalysts (e.g., alloying of the catalysts) and/or required added steps to separate out the different catalyst resulting in additional time, complexity and cost. The modular configuration of the processing apparatus of the present invention can be used to overcome this past deficiency of prior art reactors and allow the processing apparatus to be formed having a plurality of different catalysts, which processing apparatus can be later disassembled and one or more of the catalysts can be separated from the processing apparatus and/or from one or more other catalyst for separate recovery operations.

In still a further and or alternative non-limiting aspect of the present invention, two or more portions of the processing apparatus can be held together by an applied compressive force. When a compressive force is used (e.g., clamps, bolts, etc.), the contact surfaces of the portions of the processing apparatus are generally smooth so as to increase the seal between the contact surfaces; however, this is not required. In one non-limiting example, the roughness of the contact surfaces is less than about 1-20 micrometers, and substantially free of scratches. The pressure used to secure the plates together will vary depending on the pressure in the processing apparatus, among other factors. Sealing structures such as, but not limited to, O-rings and sealing rings can be used to further enhance the seal between contact surfaces.

In yet a further and/or alternative non-limiting aspect of the present invention, two or more portions of the processing apparatus can be connected together by brazing. The brazing metal will generally have a melting point that is less than the metal composition of the portions of the processing apparatus being connected together; however, this is not required. The brazing metal will also generally be substantially inert to materials passing through the processing apparatus; however, this is not required. The brazing metal will also generally be able to withstand the temperature and/or pressures in the processing apparatus. For instance, if the processing apparatus includes three components, namely a top portion, a bottom portion and a middle portion, and the contact surfaces of the top and bottom portion are made of stainless steel and the middle portion is primarily made of palladium, a brazing metal can be selected to have a melting point that is less than the melting point of palladium and stainless steel. Palladium has a melting point of about 1554° C. and stainless steel has a melting point of about 2500° C. As such, during a brazing process, the middle portion that is formed of palladium is most susceptible to damage. By selecting a brazing metal that is less than the melting point of palladium, the brazing operation for connecting the components together will not damage or minimize damage to any of the portions of the processing apparatus. Generally, the melting point of the brazing metal is at least about 50° C. less than the lowest melting temperature contact surface typically at least about 100° C. less than the lowest melting temperature contact surface, more typically at least about 200° C. less than the lowest melting temperature contact surface, and even more typically at least about 300° C. less than the lowest melting temperature contact surface. The same brazing metal can be used in the processing apparatus or two or more types of brazing metal can be used to connect two or more portions of the processing apparatus. Non-limiting examples of brazing metals that can be used include, but are not limited to, aluminum, copper, chromium, gold, iron, lead, manganese, molybdenum, nickel, niobium, platinum, rhenium, silver, tin, titanium, zinc, zirconium, vanadium, and/or various alloys thereof (e.g., nickel-silver alloys [e.g., BAg-3, BAg-4, BAg-7, BAg-13, BAg-22, etc.], nickel alloys [e.g., BNi-1, BNi-2, BNi-3, BNi-8, etc.], gold alloys [e.g., BAu-1, AAu-3, BAu-4, BAu-5, BAu-6, etc.], aluminum-silicon alloys [e.g., BAlSi-2, BAlSi-4, BAlSi-7(d), BAlSi-10(d), etc.], copper alloys [e.g., BCu-1, BCu-2, BCuP-1, etc.], iron alloys [e.g., stainless steel, carbon steel, etc.], 10PdAu, 95Ag-5Al, 9Pd-9Ga—Ag, 48Zr-48Ti-4Be, etc.). As can be appreciated, alloys of these metals and/or other metals can be used. As can be appreciated, some portions of the processing apparatus can be connected together by a brazing metal and other portions of the processing apparatus can be connected by other means (e.g., adhesive, bolts, clamps, rivets, cables, wires, traps, etc.). As can further be appreciated, the brazing metal in combination with another type of connector (e.g., bolt, clamp, etc.) can be used to connect together one or more portions of the processing apparatus. One non-limiting brazing metal than can be used to connect together palladium and stainless steel is a nickel-silver alloy, which typically has a melting point of less than about 1000° C. As can be appreciated, other metals can be used for the brazing metal. The brazing metal can be applied to the contact surfaces of the portions of the processing apparatus by plating, metal spraying, hot dipping, brushing, smearing, paste, or other type of operation. The heating of the brazing material can occur in an oven, by induction heating, by lasers, by a torch, by a welder, under high pressure, etc. When the portions of the processing apparatus are designed to be separated, the brazing metal can be reheated until it softens or becomes molten and one or more portions of the processing apparatus can then be separated from one another. The spent or partially spent catalyst in the one or more of the recovered and separated portions of the processing apparatus can then be processed and recovered. The one or more portions of the processing apparatus that did not include the catalyst can be discarded or cleaned and reused to form another processing apparatus.

In still yet a further and/or alternative non-limiting aspect of the present invention, an adhesive can be used to connect one or more portions of the processing apparatus. When the time has come to separate one or more portions of the processing apparatus and/or to recover the catalyst in one or more portions of the processing apparatus, a solvent can be used to dissolve the adhesive and enable separation of the portions of the processing apparatus. Many different types of adhesives can be used (e.g, polyurethane adhesives, etc.).

In still a further and/or alternative non-limiting aspect of the present invention, at least one portion of the processing apparatus is formed from a plurality of metal layers. The method of manufacturing the processing apparatus or one or more portions of the processing apparatus includes 1) forming sections of the processing apparatus or the one or more portions of the processing apparatus from a metal material, and 2) connecting a plurality of individual sections to form the processing apparatus or one or more portions of the processing apparatus. The thickness of the metal layers used in the processing apparatus can be the same or different. The composition of the metal layers used in the processing apparatus can be the same or different. The shape of one or more metal layers can be modified to form passageway and/or structures in the processing apparatus. The shape formation of one or more metal layers of the processing apparatus can be accomplished in a variety of ways. In one non-limiting manufacturing process for at least a portion of the processing apparatus, one or more metal layers can be stamped, bent, welded, cast, molded, extruded, die formed and/or die cut, and/or cut (e.g., laser cut, water jet cut, machine tool cut, etc.) from one or more sheets of metal. One or more of the stamped and/or cut metal layers can be connected together to another metal layer (which may or may not be shape formed) by use of an adhesive and/or a brazing metal so as to form one or more portions of the processing apparatus. As can be appreciated, all or a portion of the metal layers that are shape formed can be shape formed in the same or different manner. In another and/or alternative non-limiting manufacturing process for at least a portion of the processing apparatus, one or more metal layers of the processing apparatus can be shape-formed by 1) generating a mechanically drawn and/or computer image of the processing apparatus or one or more portions of the processing apparatus, 2) sectioning one or more portions of the mechanical drawn and/or computer-generated image so as to represent one or more metal layers to be used to at least partially form the processing apparatus, 3) forming one or more portions of the processing apparatus and/or one or more metal layers of the processing apparatus from one or more metal materials based on one or more of the sectioned drawings, and 4) connecting the formed one or more portions of the processing apparatus and/or formed one or more metal layers of the processing apparatus so as to form the processing apparatus or the one or more portions of the processing apparatus in a manner such that the formed processing apparatus or formed one or more portions of the processing apparatus substantially match the mechanically drawn and/or computer generated drawing of the processing apparatus or the one or more portions of the processing apparatus. By using this novel manufacturing process, the processing apparatus or the one or more portions of the processing apparatus can be designed to have very precise dimensions that can be manufactured to have very low error tolerances. The computer generated image and/or sections of the computer-generated image of the processing apparatus or the one or more portions of the processing apparatus can be generated by commercially available or proprietary software. One common commercial software package is AutoCAD. Many other or additional software packages can be used. The computer generated image and/or sections of the computer-generated image is generally at least a two-dimensional drawing, and typically a three-dimensional image of the processing apparatus or the one or more portions of the processing apparatus; however, this is not required. Once the computer-generated image matches the shape of the processing apparatus or the one or more portions of the processing apparatus, the computer-generated image can be then sectioned as desired to emulate one or more layers of the processing apparatus or the one or more portions of the processing apparatus; however, this is not required. Typically, the processing apparatus, when divided or sectioned, is at least partially divided or sectioned along the longitudinal axis or vertical axis of the processing apparatus or the one or more portions of the processing apparatus; however, the graphics of the processing apparatus or the one or more portions of the processing apparatus can be divided along other or additional axes of the processing apparatus or the one or more portions of the processing apparatus. The divided or sectioned layers can have the same thickness; however, this is not required. The computer generated images of the processing apparatus or the one or more portions of the processing apparatus can be saved, used in other processes (e.g., lithography process, etc.) or the like.

In still yet a further and/or alternative non-limiting aspect of the present invention, computer-generated images of the processing apparatus or the one or more portions of the processing apparatus can be used to form one or more metal layers to be used to form at least a portion of the processing apparatus. The divided or sectioned computer generated layers of the processing apparatus or the one or more portions of the processing apparatus can be used to shape form one or more metal layers that can be matched together with low error tolerances to form one or more portions of the processing apparatus; however, this is not required. Various techniques can be used to form metal layers that match one or more of the divided or sectioned computer generated layers of the processing apparatus or the one or more portions of the processing apparatus. In one non-limiting aspect of this embodiment, lithography is used to at least partially form one or more metal layers that match one or more of the divided or sectioned computer generated layers of the processing apparatus or the one or more portions of the processing apparatus. When using a lithography process, a photosensitive resistant material coating is generally applied to one or more of the surfaces (i.e., either of the relatively large planar "top" or "bottom" surfaces) of a blank of metal material (e.g., thin metal layers, etc.). After the blank has been provided with the photo-resist material coating, "mask tools" or "negatives" or "negative masks", containing a positive or negative image of the desired sectioned layer of the processing apparatus or the one or more portions of the processing apparatus are etched in the blank of metal material. The mask tools can be made from glass or other materials, which have a relatively low thermal expansion coefficient and transmit radiation such as ultraviolet light' however, this is not required. The blank can then be exposed to radiation, typically in the form of ultraviolet light, to expose the photo-resist coatings to the radiation. The masks are then removed and a developer solution is applied to the surfaces of the blank to develop the exposed (sensitized) photo-resist material. Once the photo-resist is developed, the blanks are etched or micro-machined. Once etching or machining is complete, the remaining unsensitized photo-resist material can be removed such as by, but not limited to, a chemical stripping solution. When using lithography as a basis for layer fabrication of one or more metal layers of the processing apparatus or one or more portions of the processing apparatus, many different shapes can be formed in the one or more metal layers. The shapes formed in two or more of the metal layers can be the same or different. As can be appreciated, the combinations of any number of shapes in one or more metal layers can result in non-redundant design arrays (i.e., patterns in which not all shapes, sizes, and/or spacings are identical). The lithography can be used to create very accurate feature tolerances in the one or more metal layers since those features can be derived from a potentially high-resolution photographic mask. The tolerance accuracy can include line-width resolution and/or positional accuracy of the plotted features over the desired area. Photographic masks can assist with achieving high accuracy when chemical or ion-etched, or deposition-processed layers are being used to form a processing apparatus or the one or more portions of the processing apparatus from the stack of sections. Because dimensional changes can occur during the final formation of the processing apparatus or the one or more portions of the processing apparatus, compensation factors can be engineered at the photo-mask stage, which can be transferred into the fabrication of the processing apparatus or the one or more portions of the processing apparatus. For instance, when the processing apparatus or the one or more portions of the processing apparatus needs to be angled for radial designs or some other design, the photo-mask typically needs to be applied to both sides of the metal layer with a slight offset to allow for the angle. This offset can be used to eliminate a stack-up look even though the steps will be very thin. When the brazing material, adhesive, etc. is coated on one or both sides of one or more metal layers, the etching solution typically performs a better job to form a better angled stack. In another and/or alternative non-limiting aspect of this embodiment, fabricating of one or more sections of the processing apparatus or the one or more portions of the processing apparatus can be formed by one or more micro-machining techniques (MEMS); however, this is not required. Some of the micro-machining techniques that can be used include, but are not limited to, photo-etching, laser machining, reactive ion etching, electroplating, vapor deposition, bulk micro-machining, surface micro-machining. As can be appreciated, one or more conventional machining techniques can be used to form one or more portions of the processing apparatus. Ion etching techniques can be used to form one or more metal layers of the processing apparatus or the one or more portions of the processing apparatus that have tolerances of less than about 1.25 microns. Photo-chemical-machining techniques can be used to etch one or more metal layers of the processing apparatus or the one or more portions of the processing apparatus to tolerances of less than about 2.5 microns. Laser micro-machining techniques can be used to form one or more metal layers of the processing apparatus or the one or more portions of the processing apparatus to a tolerance of less than about 0.3 micron. Electroforming techniques can be used to form one or more metal layers of the processing apparatus or the one or more portions of the processing apparatus to a tolerance of less than about 0.1 micron. When larger error tolerances are acceptable, various types of conventional metal machining techniques can be used (e.g., metal stamping, drilling, casting, ultrasonic cutting, water cutting, pressure forming, etching, laser cutting, bore cutting, etc.).

In a further and/or alternative non-limiting aspect of the present invention, one or more metal layers of the processing apparatus or the one or more portions of the processing apparatus can be connected together by a lamination process. Once a plurality of the metal layers are formed (generally by one or more of the processing techniques set forth above), at least two of the metal layers of the processing apparatus or the one or more portions of the processing apparatus are placed together and then laminated together to form the processing apparatus or one or more portions of the processing apparatus. The total number (and thickness) of the metal layers of the processing apparatus or the one or more portions of the processing apparatus define the overall height and aspect ratio of the processing apparatus or the one or more portions of the processing apparatus. In one non-limiting embodiment of the invention, a metal-to-metal brazing technique can be used to connect together one or more metal layers of the processing apparatus or the one or more portions of the processing apparatus. Prior to the assembly of the metal layers of the processing apparatus or the one or more portions of the processing apparatus, one or more of the metal layers can have one or both surfaces coated with a thin metal coating. Such metal coating can be applied by a variety of techniques such as, but not limited to, paste, thermal spraying and/or electroplating.

Generally the thickness of the metal coating is less than about 1000 microns, typically less than about 100 microns, more typically about 0.1-10 microns, and even more typically about 0.5-4 microns; however, other coating thicknesses can be used. Furthermore, when a metal paste is used, the thickness of the paste layer can be much greater than about 10-100 microns. The coated metal typically has a melting temperature that is less than the metal used to form the metal layers of the processing apparatus or the one or more portions of the processing apparatus. Generally, the coating metal has an average melting point that is at least about 10° C. less than the average melting point of the metal used to form the metal layers of the processing apparatus or the one or more portions of the processing apparatus; typically, the coating metal has an average melting point that is at least about 100° C. less than the average melting point of the metal used to form the metal layers of the processing apparatus or the one or more portions of the processing apparatus; and more typically is at least about 300° C. less than the average melting point of the metal used to form the metal layers of the processing apparatus or the one or more portions of the processing apparatus. Examples of coating metal materials include, but are not limited to, aluminum, copper, chromium, gold, iron, lead, manganese, molybdenum, nickel, niobium, platinum, rhenium, silver, tin, titanium, zinc, zirconium, vanadium, and/or various alloys thereof (e.g., nickel-silver alloys [e.g., BAg-3, BAg-4, BAg-7, BAg-13, BAg-22, etc.], nickel alloys [e.g., BNi-1, BNi-2, BNi-3, BNi-8, etc.], gold alloys [e.g., BAu-1, AAu-3, BAu-4, BAu-5, BAu-6, etc.], aluminum-silicon alloys [e.g., BAlSi-2, BAlSi-4, BAlSi-7(d), BAlSi-10(d), etc.], copper alloys [e.g., BCu-1, BCu-2, BCuP-1, etc.], iron alloys [e.g., stainless steel, carbon steel, etc.], 10PdAu, 95Ag-5Al, 9Pd-9Ga—Ag, 48Zr-48Ti-4Be, etc.). As can be appreciated, alloys of these metals and/or other metals can be used. During the lamination or brazing process, the metal layers and/or metal coatings are generally heated to an elevated temperature to cause the metal coating to soften and/or flow. The heating atmosphere can be an inert or low reacting atmosphere; however, this is not required. The heating of the brazing metal can be achieved by use of induction heating, radiant heating, lasers, furnaces, ovens, torches, electrical resistance, dipping procedures, etc. The atmosphere about the one or more metal layers during the lamination or brazing process can be under a vacuum to result in a vacuum brazing process; however, this is not required. Gas atmospheres that can be used during the brazing process can include, but are not limited to, nitrogen or noble gases, etc. The time of brazing is typically about 0.1-4 hours; however, other times can be used depending on the brazing temperature, type of brazing metal, composition of the metal layers, etc. The elevated temperature during brazing causes the brazing metal to soften and, or flow between the metal layers. Generally, the brazing temperature is at least about 5° C. higher than the melting point of the brazing metal, and typically is at least about 10° C. higher than the melting point of the brazing metal, and more typically is at least about 50° C. higher than the melting point of the brazing metal, and still more typically is at least about 100° C. higher than the melting point of the brazing metal. The brazing procedure is completed by cooling the heated metal layers. The atmosphere during cooling process is typically inert; however, this is not required. The cooling times are typically 0.1-5 hours; however, other cooling times can be used.

In still a further and/or alternative non-limiting aspect of the present invention, one or more alignment structures and one or more construction structures are used to at least partially orient two or more metal layers to at least partially form the processing apparatus. As temperatures are elevated during the brazing or lamination process, the metal layers of the processing apparatus or the one or more portions of the processing apparatus can expand. Various types of alignment structures (e.g., pins, etc.) can be used to maintain the metal layers of the processing apparatus or the one or more portions of the processing apparatus in the proper position relative to one another during the brazing or lamination process. Generally, one or more construction structures (e.g., holes, slots, ribs, etc.) are formed in one or more metal layers to facilitate in at least partially aligning together two or more metal layers. The construction structures can be sized, shaped and/or positioned on the one or more metal layers to account for expansion and/or contraction of the metal layers when exposed to heat during the brazing or lamination process. In one non-limiting aspect of this embodiment, a plurality of the metal layers include one or more construction structures to facilitate in the proper orientation of the metal layers when forming the processing apparatus or the one or more portions of the processing apparatus; however, this is not required. When one or more construction structures are included in one or more metal layers, one or more alignment structures (e.g., pins, etc.) are used to engage with and/or be at least partially inserted into the construction structures. For instance, when the construction structures are in the form of an opening or slot, the alignment structures can be in the form of a pin. These pins can be design so that the holes or slots in the metal layers are placed onto the pins thereby resulting in the proper orientation of a plurality of metal layers with respect to one another. When alignment structures are used, the alignment structures are generally made of the same material as the metal layers so that the alignment structures expand and contact at the same rate as the metal layers when exposed to heating and cooling; however, this is not required. Alternatively, the alignment structures can be formed of carbon material (e.g., graphite) or other type of material that has little or no expansion during heating and cooling. The metal layers can be clamped together or otherwise placed under pressure to limit movement of the metal layers during the connecting process (e.g., brazing process, etc.); however, this is not required. In addition to using alignment structures, positional errors and tolerances of a plurality of metal layers can be at least partially controlled by the photographic masks used to produce the metal layers. The geometric size and tolerance of the metal layers can be partially controlled by the metal layer thickness and/or micro-machining methods used to produce the metal layers; however, this is not required. When producing a laminated processing apparatus or laminated portion of the processing apparatus, numerous factors can be an influence on the overall tolerances of the metal layers. For example, when using a stacking fixture for the metal layers, the flatness of the laminating surface of the metal layers and/or the perpendicularity of the sides of the metal layers can be controlled to ensure improved stacking of the metal layers. In addition, the dimensional tolerance of the alignment features of the metal layers and/or the positional tolerance of the metal layers can be an influence to improve the stacking of the metal layers. In yet another and/or alternative non-limiting embodiment of the invention, one or more metal layers can be laminated together by use of an adhesive. Such adhesives can include, but are not limited to, thermo-cured epoxy, non-thermo-cured epoxy, silicone rubber products, urethanes, etc. When using lamination techniques other than brazing, the metal layers of the processing apparatus or the one or more portions of the processing apparatus are typically clamped together or otherwise placed under pressure until the adhesive has at least partially dried and/or cured.

In another and/or alternative non-limiting aspect of the invention, the metal layers used to form the processing apparatus or the one or more portions of the processing apparatus can be made from a wide variety of metals. The one or more metal layers can be made of a single metal or be at least partially formed from a metal alloy. The processing apparatus or the one or more portions of the processing apparatus can be formed of the same of different metals. In one non-limiting embodiment of the invention, at least a portion of the top or front portion and/or the bottom or back portion of the processing apparatus is formed one or more metal layers that are a durable metal. Such durable metals include, but are not limited to, stainless steel (e.g., 304, 316, etc.), nickel, nickel alloys (N02200, N02205, N02270, N04400, N06600, N08800, N10001, etc.) aluminum, aluminum alloys (1160, 1100, 1235, etc.), titanium, titanium alloys (Ti-0.3Mo-0.8Ni, Ti-6Al-4V, Ti-10V-2Fe-3Al, etc.), copper, copper alloys (e.g., brass, etc.). In still another and/or alternative non-limiting aspect of this embodiment, the middle portion or a segment of the middle portion of the processing apparatus can be at least partially formed from one or more metal layers that can function as catalyst metal; however, this is not required. Such metal layers that can function as a catalyst include, but are not limited to, aluminum, cobalt, copper, gold, iridium, lithium, molybdenum, nickel, platinum, palladium, rhodium, ruthenium and/or silver. As mentioned above, one or more metal layers can be made fully from a single metal or can be made of a plurality of metals. Alternatively or additionally, the processing apparatus or one or more portions of the processing apparatus can be made of one or more metal layers formed of the same or different metal. The thickness of the metal layers can vary depending on the size of the processing apparatus, the configuration of the processing apparatus, the metal composition of the processing apparatus in certain locations of the processing apparatus, etc. Generally the average thickness of the metal layers is at least about 10 µm, and more typically at least about 40 µm. The maximum average thickness of the metal layers is typically no greater than about 500,000 µm, typically no greater than about 250,000 µm, and even more typically no greater and about 25,400 µm; however, it can be appreciated that thickness of greater than about 500,000 µm can be used in some applications. As can be appreciated, other thicknesses can be used. When the processing apparatus is in the form of micro-reactor, the average thickness of a plurality of metal layers that form at least a portion of the micro-reactor is generally about 10-5,000 µm, typically about 20-2,000 µm, more typically about 30-1,000 µm, and even more typically about 30-800 µm. As can be appreciated, other thicknesses can be used. When the processing apparatus is in the form of micro-reactor and one or more metal layers are at least partially used as a catalyst in the form of a precious metal, the average thickness of the metal layers is generally at least about 1 µm, typically less than about 10,000 µm, more typically about 8-1,000 µm, even more typically about 10-500 µm, still more typically about 15-400 µm, and still even more typically about 40-150 µm. As can be appreciated, other thicknesses can be used. When thin thicknesses of the metal layers are used (i.e., no greater than about 1000 µm), such thin metal layers can be used to facilitate in the ease of processing the metal layers, such as, but not limited to, processing the metal layers by a lithography process. The increased ease of processing the metal layers can result in a higher quality processing apparatus. As defined in this invention, thin metal layers are metal layers having an average thickness of no greater than about 1000 µm.

In still another and/or alternative non-limiting aspect of the present invention, the one or more metal layers of processing apparatus or the one or more portions of the processing apparatus can be strategically positioned in the stack of metal layers to achieve the desired properties of the processing apparatus. For instance, one or more metal layers that can also function as a catalyst can be strategically positioned in the stack of metal layers so that one or more passageways in the processing apparatus are at least partially formed of the catalytic metal layers so as to achieve a desired reaction as reactants pass through the passageways of the processing apparatus. The manufacturing method of the present invention can thus enable the formation of a processing apparatus having a small but intricate and complex three-dimensional passageway system through the processing apparatus. Such intricate and complex three-dimensional passageway system can be used to achieve a high reaction surface area to strength ratio; and/or can be used for other or additional reasons. If desired, one or more portions of the processing apparatus can be at least partially encased in a durable structure and/or clamped together (e.g., toggle press or wedge clamp, etc.) to enable the one or more processes in the processing apparatus to safely occur at elevated pressures and/or temperatures beyond that of which can be achieved using the traditional cylindrical reactor vessels, plated ceramic catalyst beds and the ceramic honeycomb catalyst supports used in the chemical industry today; however, this is not required. The manufacturing process for the processing apparatus of the present invention also enables the materials passing through the processing apparatus to be exposed to multiple catalysts as the materials pass through the processing apparatus, if such a configuration is desired. As a result, the processing apparatus can be used to eliminate the need for multiple reactor vessels in a refinery. Increasing chemical production by use of the processing apparatus of the present invention merely requires adding additional processing apparatus to the system. As a result, the processing apparatus eliminates the need of installing large vessel reactors online to anticipate increased demand in the future (which large reactors result in underutilization of the reactor). In addition, chemical processing by use of the processing apparatus can be safer, cleaner, more accurate and efficient at the pressures and temperatures as compared to larger reactor vessels. Recovery of the catalyst, especially a precious metal catalyst, is much simpler in the processing apparatus of the present invention than melting the entire reactor down (when it becomes plugged or deficient) and separating the elements at their perspective melt and density points or using various highly toxic methods of reduction now in use at most of the catalyst producers (e.g., separating the precious metal from the ceramic supports). The method of recovery of the catalyst in the processing apparatus of the present invention, when a catalyst is used, can be not only simpler and less costly, it can also be much more environmentally friendly. Changeover of catalyst beds when using the processing apparatus of the present invention can be done unit by unit while still under processing conditions instead of shutting down whole reactor vessels to change out tons of catalyst.

In still another and/or alternative non-limiting aspect of the present invention, the processing apparatus can be used as a heat exchanger. The processing apparatus can be used to create a high efficiency heat exchanger; however, this is not required. In one non-limiting embodiment of the invention, the heat exchanger includes a plurality of metal layers that are laminated together. The lamination process is typically a metal brazing process. The heat exchanger includes one or more passageways to enable a fluid to flow through the passageway. In one non-limiting aspect of this embodiment, the heat exchanger is in the form of a furnace element that is designed to burn a gas (e.g., natural gas, hydrogen, methane, etc.) so as to generate heat that can be transferred to a fluid that flows at least partially through and/or about one or more portions of the heat exchanger. In one non-limiting specific example, the furnace element is designed to burn natural gas. This furnace element can be place in a conventional home heating unit; however, this is not required. In such non-limiting example, the furnace element is formed of a plurality of metal layers that are laminated together. Typically the lamination is by use of a brazing metal. The metal layers can be formed of the same or different material. Generally, at least one of the metal layers includes a high heat conductive metal to facilitate in the transfer of heat in the furnace element. Non-limiting examples of such materials includes aluminum, aluminum alloys, copper, copper alloys, stainless steel, etc. As can be appreciated, other or additional metals can be used. The metal layers can have the same or different thicknesses. Generally the thickness of the metal layers is less than about 4 inches (101,600 microns); however, this is not required. One or more of the metal layers include one or more channels and/or passageways so that when the metal layers are connected together, the furnace element includes one or more passageways. When a brazing metal is used to connect together two or more metal layers so as to at least partially form the furnace element, the brazing metal has a melting point that is generally at least 100° C. less than the metal point of the metal layers that the brazing metal is to be used to connect together. For example, if two copper metal layers are to be connected together, the brazing metal would generally have a melting point of less than about 983° C. Non-limiting examples of such metals include aluminum, lead, tin, zinc, and alloys thereof. The type of metal for the metal layers and the brazing metal is generally 50° C. greater than the highest anticipated operating temperature of the furnace element. For example, if the highest furnace element temperature is anticipated to be about 590-650° C., the melting point of the metal layers and the brazing material generally should be at least about 700° C. Non-limiting examples of such metals include brass, bronze, copper, carbon steel, stainless steel, etc. As such, if a copper layer and steel layer was used to form at least a portion of the furnace element, a brazing material such as brass and/or bronze can be used. As can be appreciated, many other types of metal layers and/or brazing metals can be used. As can also be appreciated, different portions of the furnace element may be exposed to different temperatures. For example, the portion of the furnace element wherein the natural gas is burned is generally the highest temperature portion of the furnace element. The portions of the furnace element that are downstream of the combustion or burning region for the natural gas are typically exposed to lower temperatures. As such, portions of the furnace element that are exposed to different temperatures can be formed of different metal layers and/or brazing materials; however, this is not required. When burning natural gas, oxygen is generally mixed with the natural gas to facilitate in the combustion of the natural gas. When the oxygen is added to the furnace element, the oxygen can be mixed with the natural gas prior to being fed into the furnace element and/or inserted into an oxygen port in the furnace element. In such an arrangement, natural gas is fed into a gas port and the mixes with the oxygen fed into the oxygen port. Typically oxygen is fed into the furnace element inserting air into the oxygen port; however, this is not required. The furnace element can include one or more valves to control the flow of natural gas and/or oxygen into the furnace element; however, this is not required. The furnace element can include one or more temperature monitoring devices to monitor the temperature in one or more regions of the furnace element; however, this is not required. The size, length, shape and/or number of passageways in the furnace element can be selected to control the rate of combustion of the natural gas and/or the amount of heat generation and/or heat transfer in one or more portions of the furnace element. A vacuum can be applied to one or more portions of the furnace element to facilitate in drawing oxygen, natural gas and/or by products of the combustion of the natural gas through one or more portions of the furnace element; however, this is not required. A sulfur removing arrangement (e.g., sulfur/sulfur compound scrubber, nitrogen compound scrubber, etc.) can be used to remove sulfur and/or sulfur compounds from the natural gas and/or combustion components from the combustion of the natural gas; however, this is not required. The furnace element can include one or more catalysts and/or compounds to facilitate in the combustion of the natural gas and/or formation and/or removal of combustion components from the combustion of the natural gas; however, this is not required.

In still yet another and/or alternative non-limiting aspect of the present invention, the processing apparatus can be used to form methanol from the reacting of carbon dioxide with water. One or more catalysts are typically used to facilitate in the reacting of carbon dioxide with water. Such catalysts can include, but are not limited to, chromium-aluminum, copper, copper-chromium, molybdenum, nickel, palladium, platinum, silver, vanadium, etc. As can be appreciated, other or additional metal catalysts can be used. The process for forming methanol is non-limiting. Two types of methanol reactions that can be formed by the processing apparatus of the present invention are illustrated and described in U.S. Pat. Nos. 3,959,094; 5,492,777 and 5,599,638, all of which are incorporated herein by reference.

One non-limiting object of the present invention is processing apparatus and a manufacturing process for the processing apparatus or one or more portions of the processing apparatus that involves the formation of at least a portion of the processing apparatus by a plurality of metal layers.

Another and/or alternative non-limiting object of the present invention is a manufacturing process for a processing apparatus or one or more portions of a processing apparatus that can be at least partially formed by the use of computer generated images and lithographic techniques.

Still another and/or alternative non-limiting object of the present invention is a manufacturing process for a processing apparatus or one or more portions of a processing apparatus that includes the connecting of metal layers to form the processing apparatus or one or more portions of the processing apparatus.

Yet another and/or alternative non-limiting object of the present invention is a manufacturing process for a processing apparatus or one or more portions of a processing apparatus that includes brazing to connect together one or more metal layers of a processing apparatus or one or more portions of a processing apparatus.

Still yet another and/or alternative non-limiting object of the present invention is a manufacturing process for a processing apparatus or one or more portions of a processing apparatus that includes a lithographic technique to form distinct shapes in one or more metal layers that are representative of one or more sections of the processing apparatus or one or more portions of the processing apparatus.

A further and/or alternative non-limiting object of the present invention is a manufacturing process for a processing apparatus or one or more portions of a processing apparatus that utilizes alignment structures and construction structures to properly align a plurality of metal layers to facilitate in the proper formation of the processing apparatus or one or more portions of the processing apparatus.

Still a further and/or alternative non-limiting object of the present invention is a manufacturing process for a processing apparatus or one or more portions of a processing apparatus that includes at least one metal coating on one or more sides of one or more metal layers for use in brazing one or more metal layers together to form the processing apparatus or one or more portions of the processing apparatus.

Yet a further and/or alternative non-limiting object of the present invention is a manufacturing process for a processing apparatus or one or more portions of the processing apparatus that can form the processing apparatus or one or more portions of the processing apparatus in many desired simple and/or complex shapes.

Still yet a further and/or alternative non-limiting object of the present invention is a processing apparatus that enables one or more portions and/or sections of the processing apparatus to be easily connected together and/or disconnected from one another.

Another and/or alternative non-limiting object of the present invention is a processing apparatus that enables simplified catalyst recovery from the processing apparatus.

Still another and/or alternative non-limiting object of the present invention is a processing apparatus that enables multiple catalysts to be used and enables the multiple catalysts to be easily separated for separate recovery processes.

Yet another and/or alternative non-limiting object of the present invention is a manufacturing process for a processing apparatus or one or more portions of a processing apparatus that allows for easier scalability of the processing apparatus from laboratory settings to industrial settings.

Still yet another and/or alternative non-limiting object of the present invention is a processing apparatus that can be designed withstand a large range of pressures and temperatures.

A further and/or alternative non-limiting object of the present invention is a processing apparatus that can have a modular design.

Still a further and/or alternative non-limiting object of the present invention is a processing apparatus has a modular design and has standardized components that can be used in forming a variety of different processing apparatus.

Yet a further and or alternative non-limiting object of the present invention is a processing apparatus that has a high surface area to strength ratio.

These and other objects and advantages will become apparent from the discussion of the distinction between the invention and the prior art and when considering the preferred non-limiting embodiment as shown in the accompanying drawings.

BRIEF DESCRIPTION OF THE DRAWINGS

The foregoing objects, and others, will in part be obvious and in part pointed out more fully hereinafter in conjunction with the written description of preferred non-limiting embodiments of the invention illustrated in the accompanying drawings in which:

FIG. 4B is another cross-sectional view of a middle portion of a processing apparatus of the present invention;

DETAILED DESCRIPTION OF NON-LIMITING EMBODIMENTS

Figure 1:
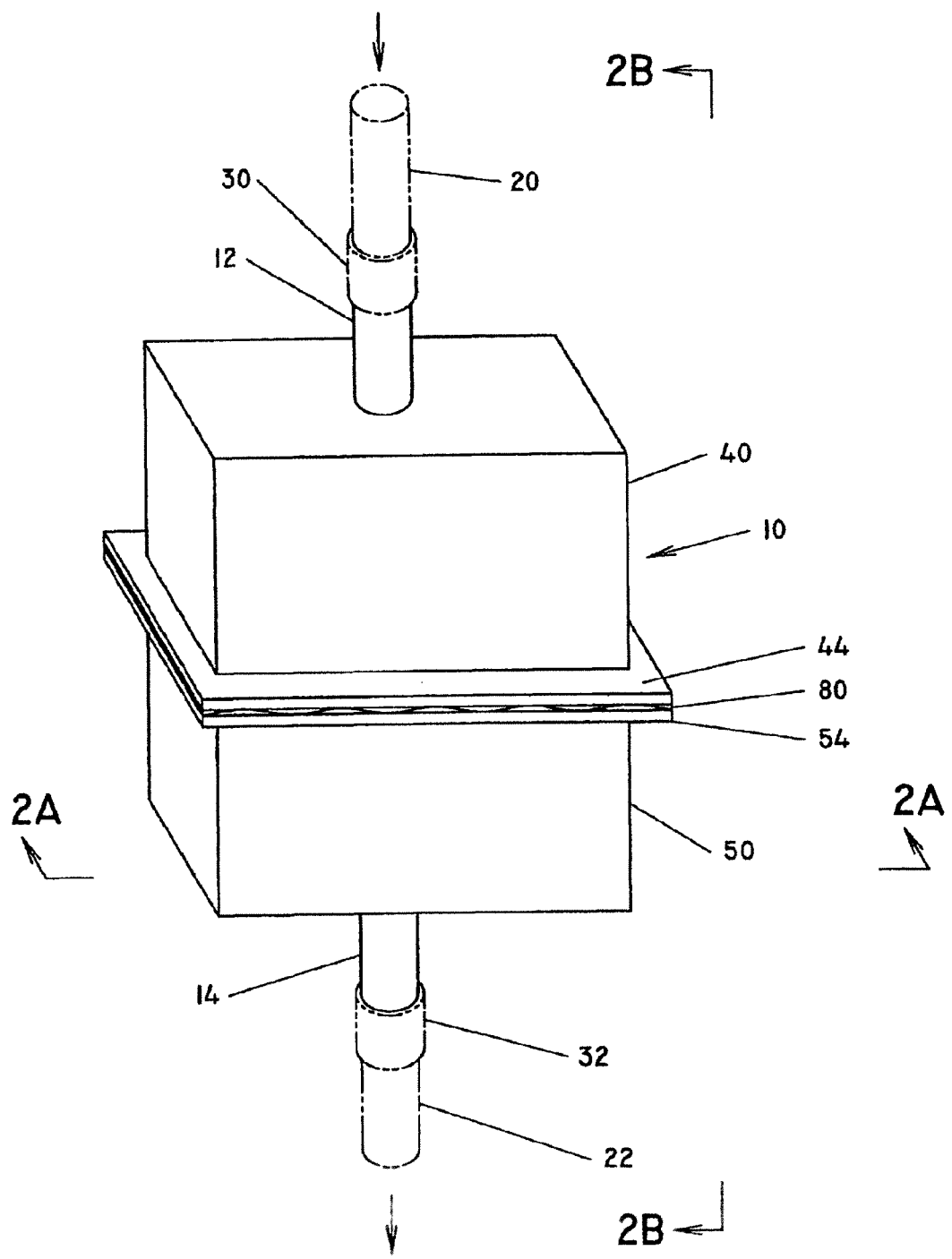
FIG. 1 is an elevation view of one non-limiting processing apparatus of the present invention connected between two pipes.

Referring now in greater detail to the drawings, wherein the showings are for the purpose of illustrating non-limiting embodiments of the invention only and not for the purpose of limiting the invention, FIG. 1 illustrates one non-limiting processing apparatus 10 in accordance with the present invention. The processing apparatus 10 is illustrated as being connected between two pipes 20, 22. As can be appreciated, more than two pipes can be connected to processing apparatus 10. The arrows illustrate that one or more materials enter the processing apparatus from pipe 20 and exit the processing apparatus by pipe 22. Processing apparatus 10 includes two connection extensions 12, 14 that are connected to pipes 20, 22 respectively by connectors 30, 32. Connectors 30, 32 can be any type of connector (e.g., connection sleeve, threaded pipe end, quick connector, etc.). As can be appreciated, pipe 20 and/or pipe 22 can be directly connected to the body of the processing apparatus.

The processing apparatus is illustrated as having a generally rectangular cross-sectional shape; however, the processing apparatus can have many of other shapes such as, but not limited to, square, oval, circular, etc. The processing apparatus is also illustrated as having a generally uniform cross-sectional shape; however, the cross-sectional shape can be non-uniform along the longitudinal and/or lateral length of the processing apparatus. When the processing apparatus is in the form of a micro-reactor, the micro-reactor has total volume that is generally less than about 1000 cubic inches, typically less than about 500 cubic inches, more typically less than about 200 cubic inches, and even more typically less than about 100 cubic inches; however, other sizes of the micro-reactor can be formed. When the processing apparatus is in the form of a furnace element, which is a subset of a reactor or micro-reactor of the present invention, for use in a residential furnace, the furnace element has total volume that is generally less than about 2000 cubic inches, typically less than about 1500 cubic inches, and more typically less than about 1000 cubic inches; however, other sizes of the furnace element can be formed.

When the processing apparatus is formed as a micro-reactor, the micro-reactor can be designed such that one or more reactants (e.g., gas, liquid, solid particles, etc.) that are to be processed are introduced or flowed into the inlet of the micro-rector. The reactants in the micro-reactor can be subjected to desired temperatures, pressures, flow rates and/or catalysts to achieve the desired chemical reaction. One or more channels or passageways through the micro-reactor can be formed to obtained the desired mixing rates, flow rates, heat exchange, and/or catalytic reactions of one or more of the reactants in the micro-reactor. After the reacted chemicals have passed through the micro-reactor, the reacted chemicals exit the outlet port of the micro-reactor and proceed to further processing or packaging. The micro-reactor is particularly directed to the specialty chemical industry which includes pharmaceuticals; however, the micro-reactor can be used to manufacture non-specialty chemicals. The processing apparatus of the present invention when in the form of a micro-reactor has the following advantages over prior art reactors, namely 1) ability to create intricate passageways in the micro-reactor, 2) has enhanced heat transfer capabilities, 3) ease of scale via adding additional micro-reactors on-line instead of past scale-up process, 4) ability to withstand high temperatures and/or pressures, is so desired, 5) ability to immobilize catalysts so as to minimize diffusional mass transfer resistances and/or pressure drop, 6) ease of manufacture, 7) ease of duplication, and/or 8) the ability to stack various modules or portions of the micro-reactor together. As can be appreciated, other advantages may exist by using the micro-reactor.

When the processing apparatus is formed as a heat exchanger, the heat exchanger can be designed such that one or more materials (e.g. gas, liquid, etc.) are flowed into the inlet of the heat exchanger. The materials in the heat exchanger can then be subjected to desired temperatures, pressures, and/or flow rates to achieved the desired about of heat exchange with the walls of the heat exchanger and/or one or more other materials flowing in and/or about the heat exchanger. One or more channels or passageways through the heat exchanger can be formed to obtained the desired mixing rates, flow rates, and/or heat exchange of one or more of the material in the heat exchanger. After the materials have passed through the heat exchanger, the materials exit the outlet port of the heat exchanger.

The processing apparatus can be formed such that the processing apparatus has functioned both as a reactor and a heat exchanger. For example, the processing apparatus can be a furnace element that is designed to burn a gas and then transfer the generated heat to air and/or liquid in and/or about the furnace element. As can be appreciated, the processing apparatus can be formed in many other types of devices.

Figure 2A:
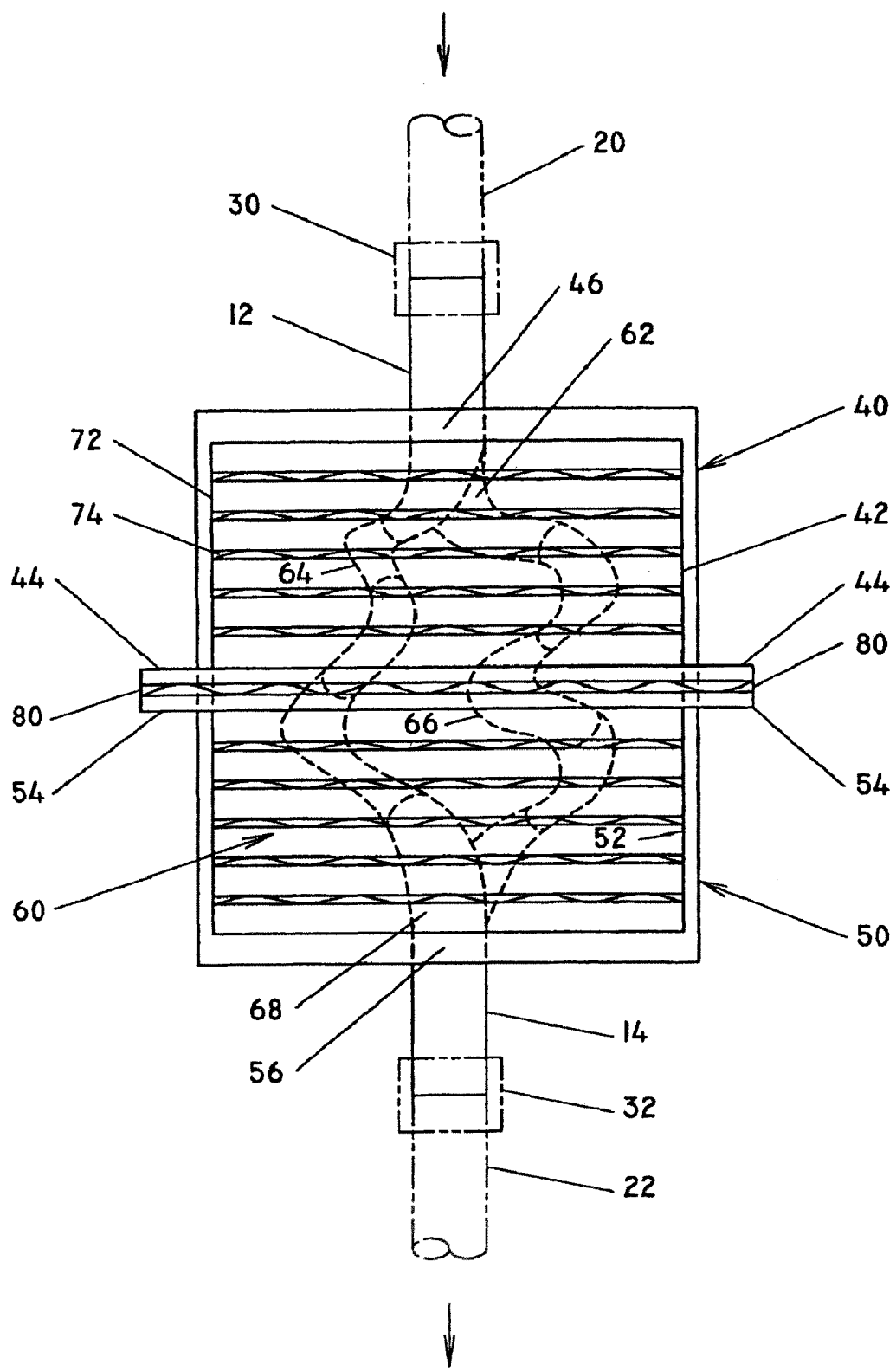
FIG. 2A is a cross-sectional view along lines 2A-2A of FIG. 1.
Figure 2B:
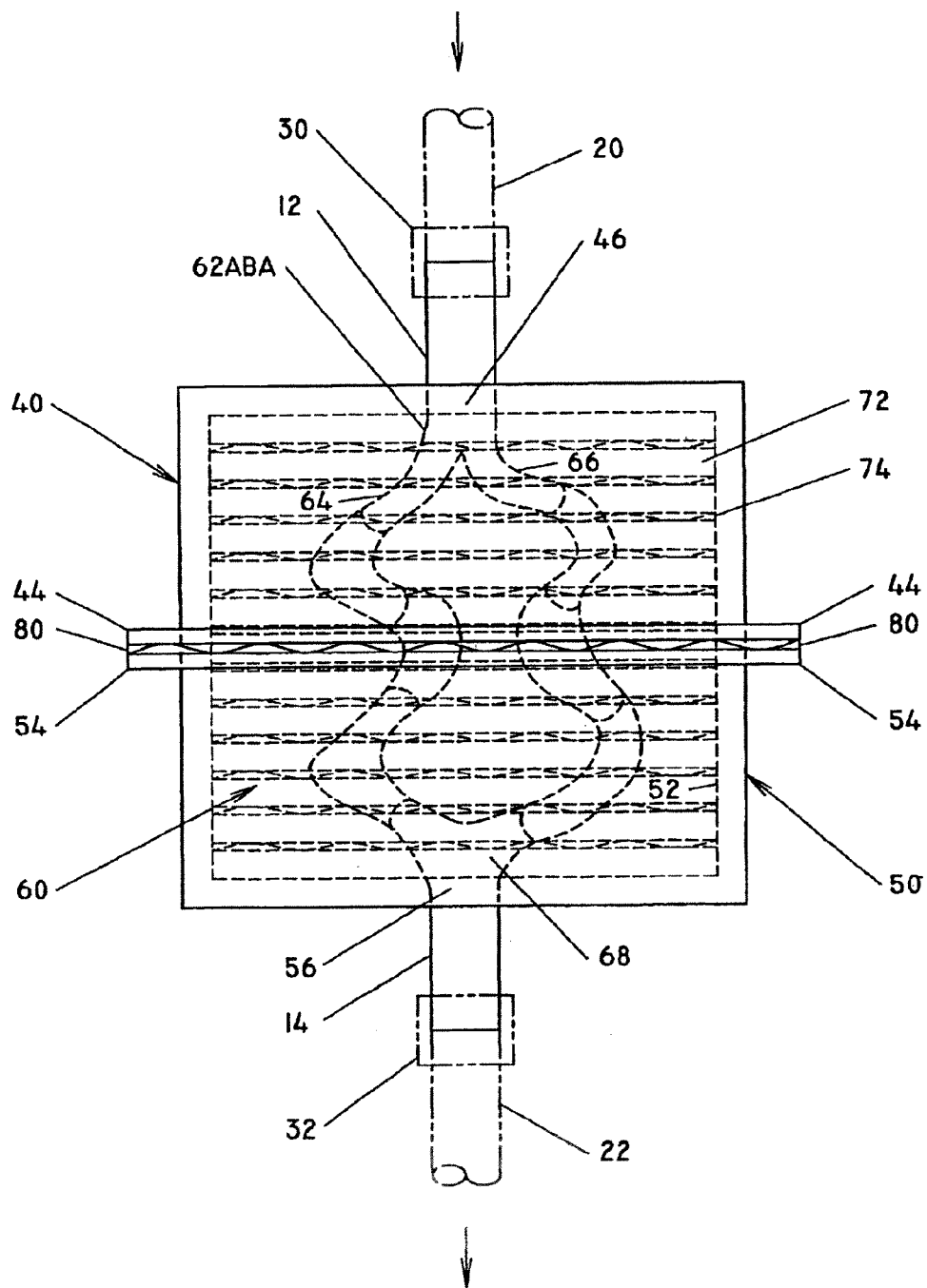
FIG. 2B is a cross-sectional view along lines 2B-2B of FIG. 1.

Referring again to FIG. 1, the top portion 40 of processing apparatus 10 is shown to include connection extension 12, and the bottom portion 50 is shown to include connection extension 14. When the processing apparatus is to be used in high pressure and/or high temperature applications, the top and bottom portions of the processing apparatus are typically made of a durable material. Non-limiting examples of such durable materials include, but are not limited to, ceramic, stainless steel, nickel alloy, titanium alloy, etc. The top and bottom portion of the processing apparatus are also typically made of the same material; however, this is not required. As illustrated in FIGS. 2A and 2B, the top portion and bottom portion include a cavity 42, 52 respectively which is designed and sized to receive and encapsulate a middle portion 60 when the top and bottom portions are positioned together. As can be appreciated, the top and/or bottom portions can be designed without a cavity. As can also be appreciated, the processing apparatus may only include the middle portion, or the middle portion and the top or bottom portion.

Figure 3:
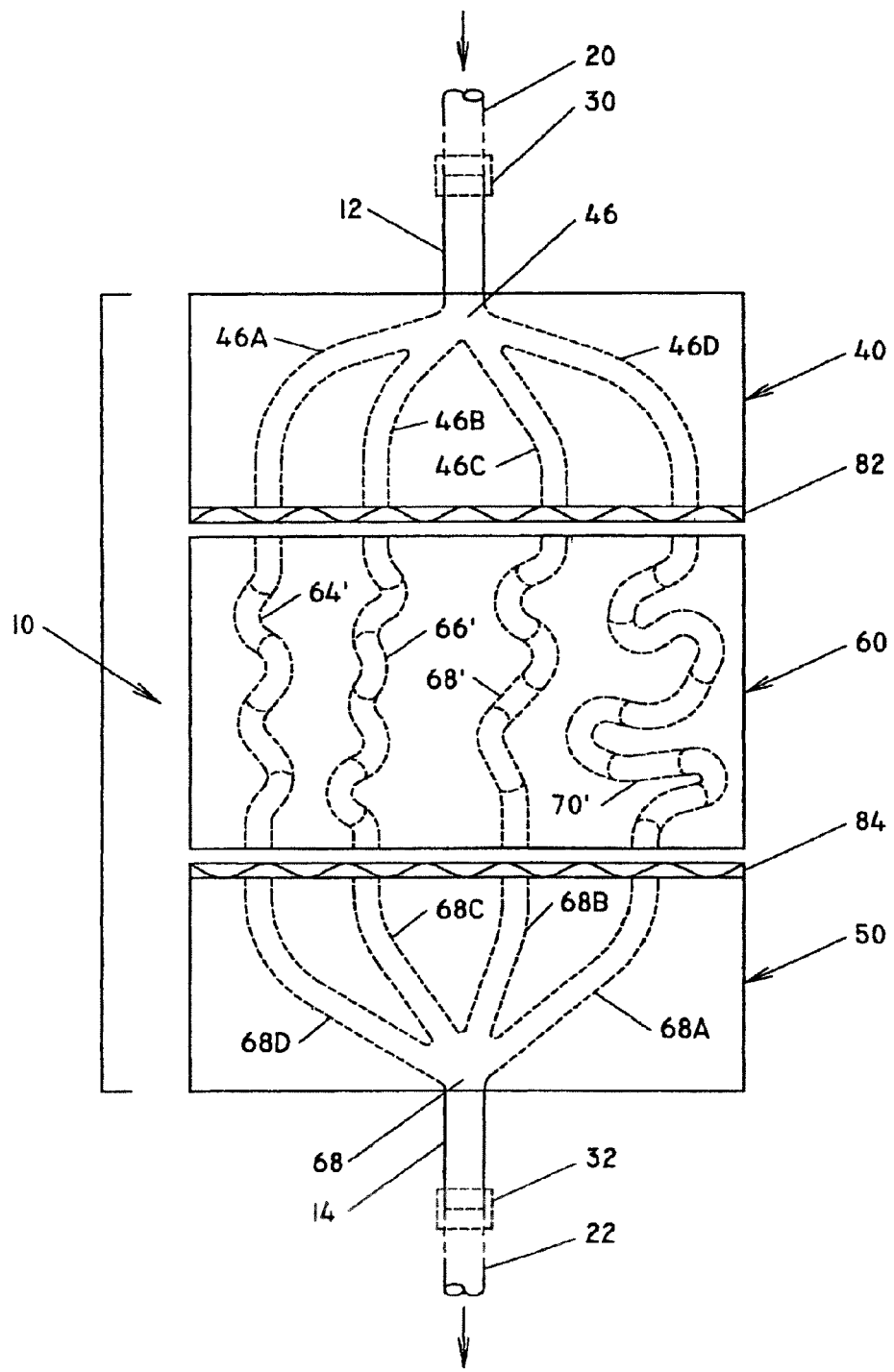
FIG. 3 is a cross-sectional view of another non-limiting configuration of a processing apparatus of the present invention.

Referring now to FIG. 3, another non-limiting configuration of the processing apparatus is shown. The top and bottom portions of the processing apparatus do not include a cavity? thus do not encapsulate the middle portion between the top and bottom portions. As can be appreciated, the top or bottom portion can be designed with a cavity that can be substantially fully receive the middle portion and the other portion is merely designed to cover the bottom of the cavity to encapsulate the middle portion between the top and bottom portion. As can further be appreciated, many other configurations for the top and bottom portions can be used to partially or fully encapsulate the middle portion of the processing apparatus.

Referring again to FIGS. 1, 2A and 2B, a securing flange 44, 54 is positioned at the base of each cavity of the top and bottom potions. As can be appreciated, the top and/or bottom portions of the processing apparatus can be designed without a flange. The securing flanges, when used, are used to help secure the top and bottom portions of the processing apparatus together. As can be appreciated, one or more clamps, bolting arrangements, locks, rivets, etc. can be used in conjunction with the flanges to secure the top and bottom portions of the processing apparatus together. The flanges can also and/or alternatively be connected together by welding, soldering or brazing metal. As shown in FIGS. 1, 2A and 2B, the flanges are connected together by a brazing metal 80 which will be discussed in more detail below.

As shown in FIGS. 1, 2A and 2B, the top and bottom portions of the processing apparatus are typically designed to at least partially encase the middle portion 60 to provide protection to the middle portion. This can be an especially advantageous arrangement when the middle portion is exposed to high temperatures, exposed to high pressures, contains and/or is at least partially formed of a catalyst material, and/or contains and/or is at least partially formed of a valuable catalyst material. For example, the middle portion may contain and/or be at least partially formed of a valuable catalyst material (i.e., a precious material) that needs to be secured. Such encapsulation by the top and bottom portions can be used to at least partially provide such secure environment. In another and/or alternative example, the middle portion may contain and/or be at least partially formed of a catalyst material that is adversely affected by atmospheric conditions (e.g., water, oxygen, nitrogen, carbon dioxide, etc.). The encasing provided by the top and bottom portions provides protection to the middle portion. If the middle portion need not be protected and/or supported by the top and/or bottom portions, the middle portion can be exposed as illustrated in FIG. 3.

As illustrated in FIGS. 2A, 2B and 3, the top and bottom portion can include one or more passageways to direct material into and/or receive materials from the middle portion. As illustrated in FIGS. 2A and 2B, the top portion 40 includes a single passageway 46 and the upper surface. The bottom portion 50 also includes a single passageway 56. Passageway 46 directs material into a passageway 62 in the middle portion which divides into two passageways 64, 66 and then reforms at the base of the middle portion into a single passageway 68. The materials are then directed into passageway 56 to direct the materials out of the processing apparatus. As illustrated in FIG. 3, the top and bottom portions can have a plurality of passageways; however, this is not required. Connection extension 12 is illustrated as feeding material into the single passageway 46 in top portion 40. Passageway 46 then splits into four passageways 46a, 46b, 46c and 46d. The four passageways then direct the material into four passageways 64', 66', 68', and 70' in middle portion 60. After the material has passed through the middle portion, the material flows into passageways 68a, 68b, 68c, and 68d in bottom portion 50 and then merges into single passageway 68 near the base of the bottom portion. As can be appreciated, many other passageway configurations can be utilized in the processing apparatus.

As illustrated in FIGS. 2A, 2B and 3, the passageways through the portions of the processing apparatus can take on many different shapes. The passageways can be tubular, but this is not required. In FIG. 3, the passageways have a generally uniform cross-sectional shape and size; however, this is not required. The length and route through the middle portion of each of the passageways is shown to be different; however, this is not required. In FIGS. 2A and 2B, the passageways do not maintain a uniform cross-section shape and size; however, this is not required. The route through the middle portion of each of the passageways is shown to be different; however, this is not required. As can be appreciated, one or more of the passageways can have the same shape, length and/or size. As can also be appreciated, the passageways can all have different shapes, lengths and/or sizes. The size, shape and/or length of one or more passageways in the top, bottom and/or middle portions of the processing apparatus can be selected to achieve certain flow rates, material resident times, pressure profiles, temperature profiles, catalyst exposure times, mixing profiles, heat exchange times, etc.

Figure 4:
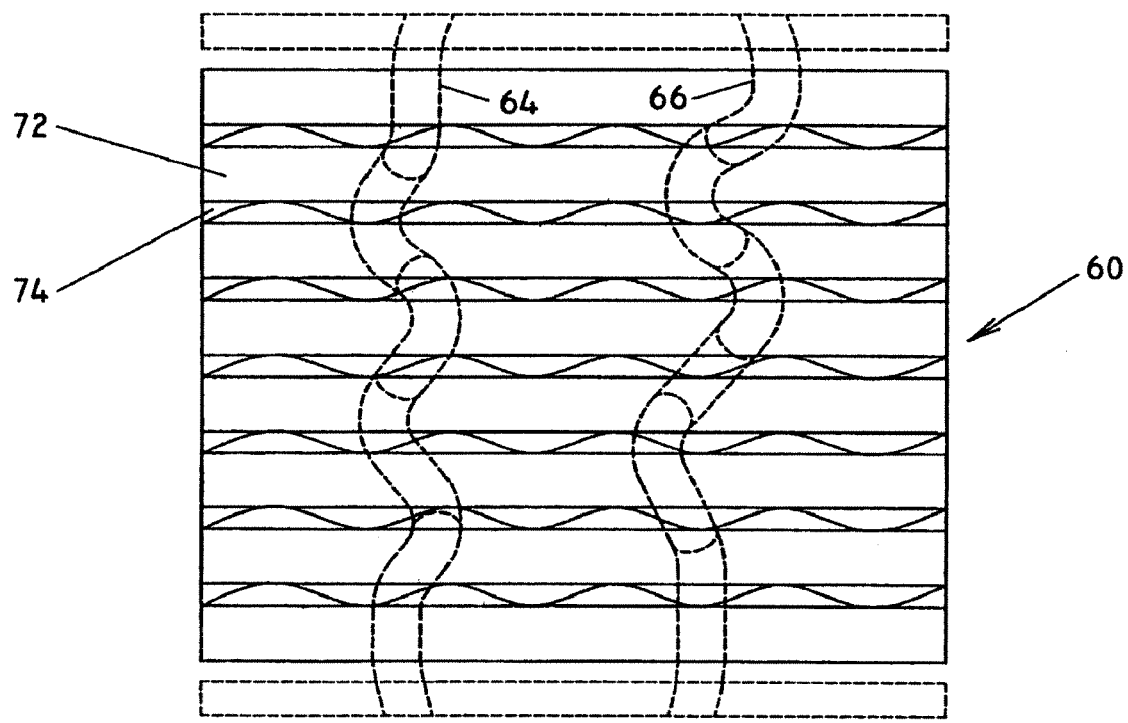
FIG. 4 is a cross-sectional view of a middle portion of a processing apparatus of the present invention.
Figure 4A:
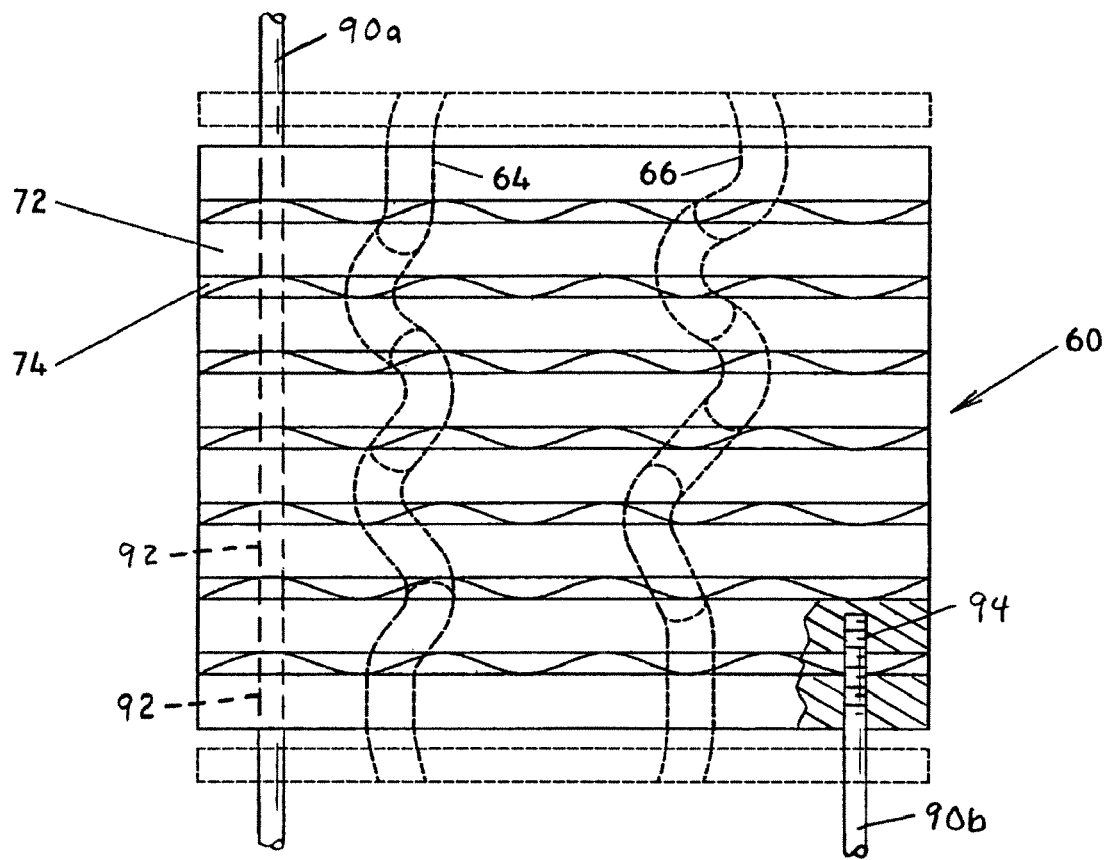
FIG. 4A is another cross-sectional view of a middle portion of a processing apparatus of the present invention showing the use of alignment structures and construction structures.
Figure 4C:
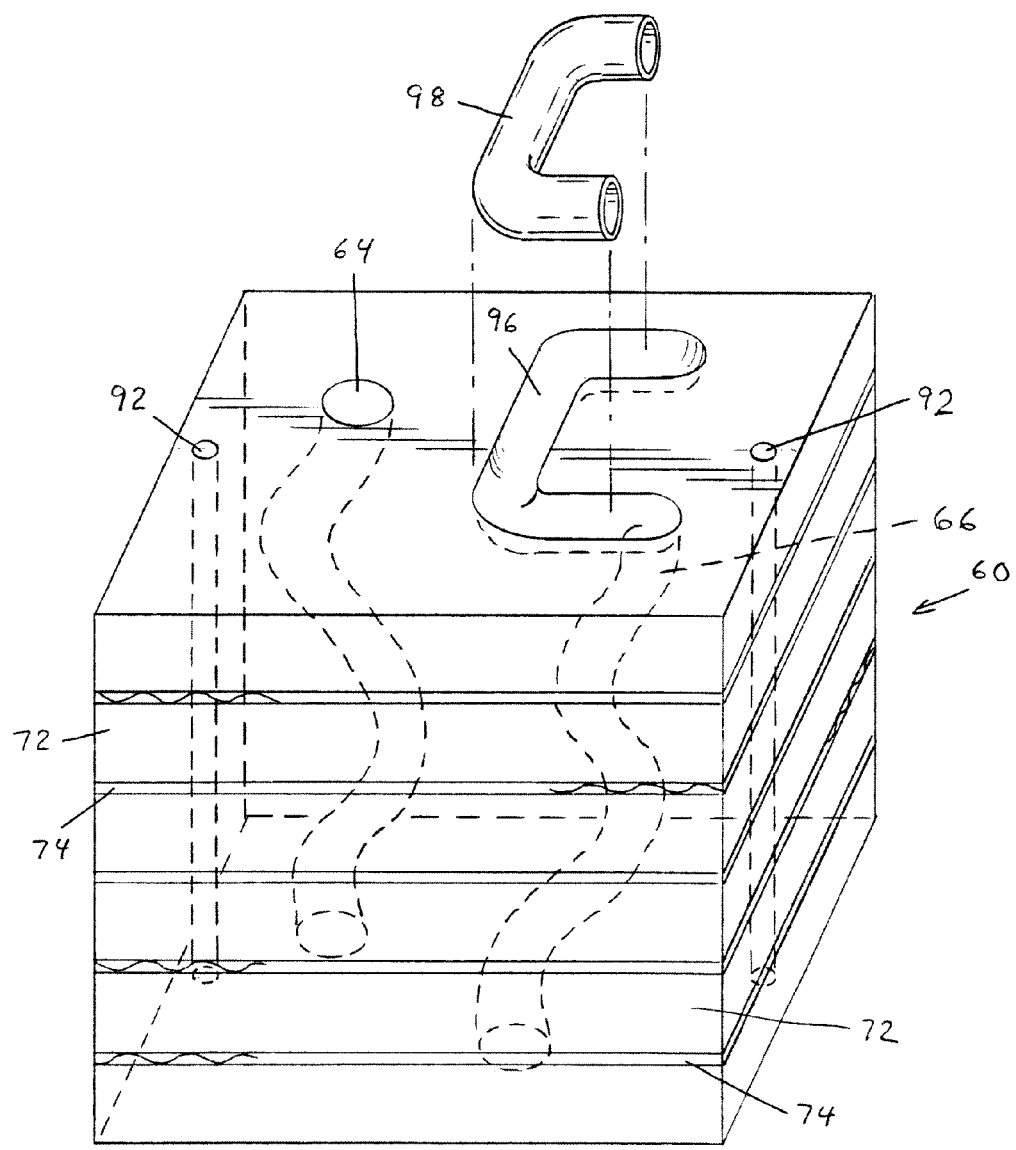
FIG. 4C is a sectional view of a middle portion of a processing apparatus of the present invention.
Figure 5:
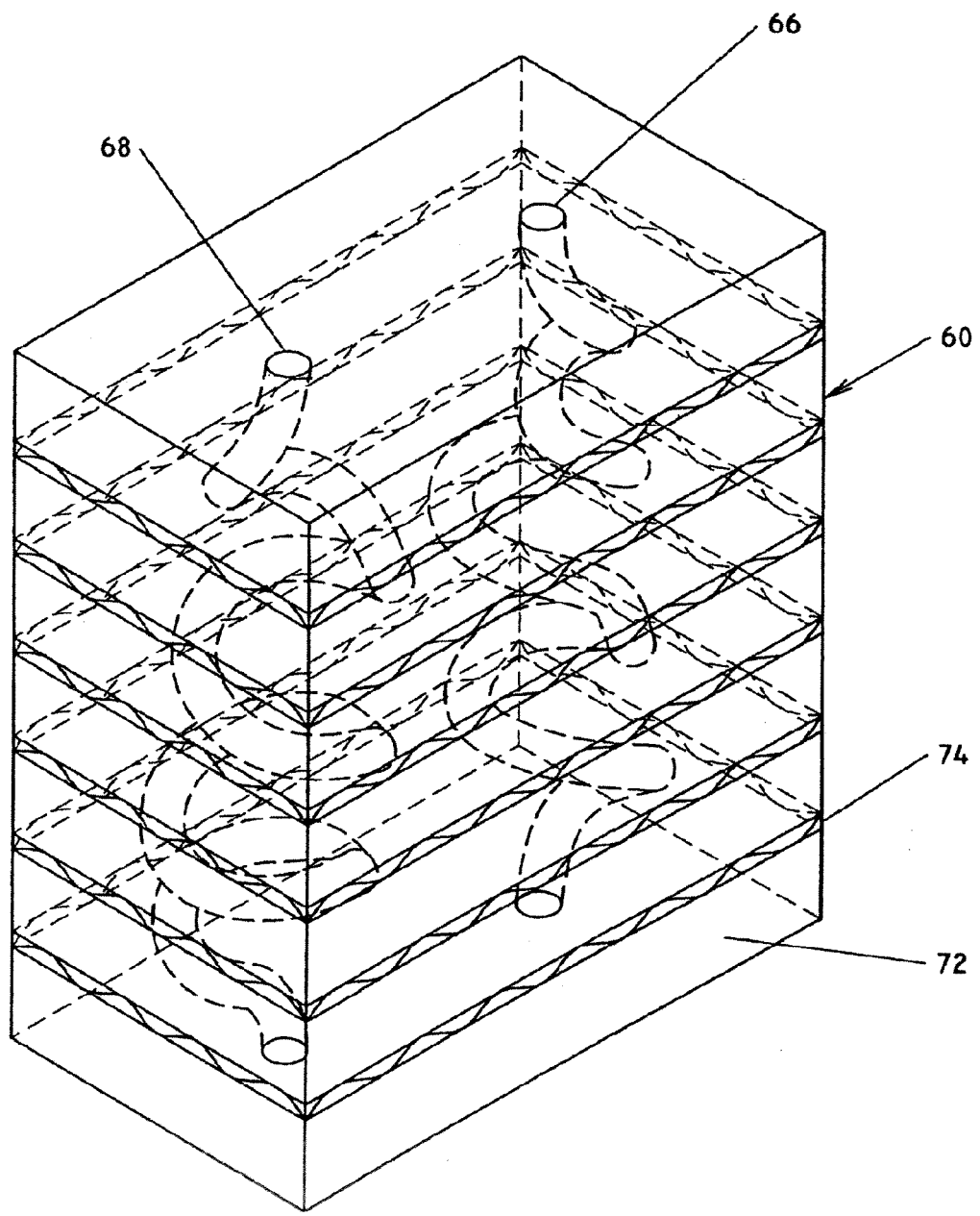
FIG. 5 is an elevation view of another non-limiting arrangement of a middle portion of a processing apparatus of the present invention.
Figure 5A:
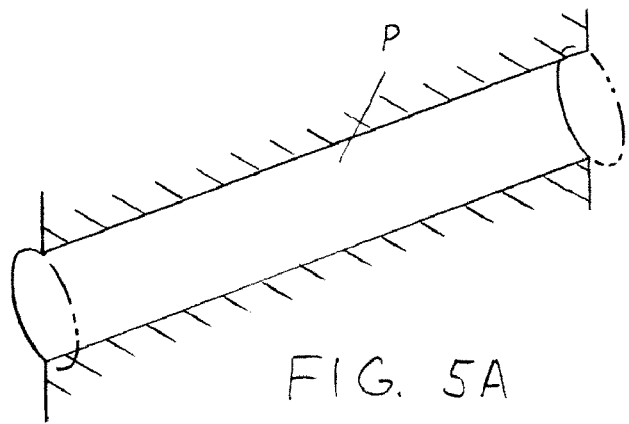
FIGS. 5A-C illustrate various non-limiting shapes of passageways that can be formed in a processing apparatus of the present invention.
Figure 5B:
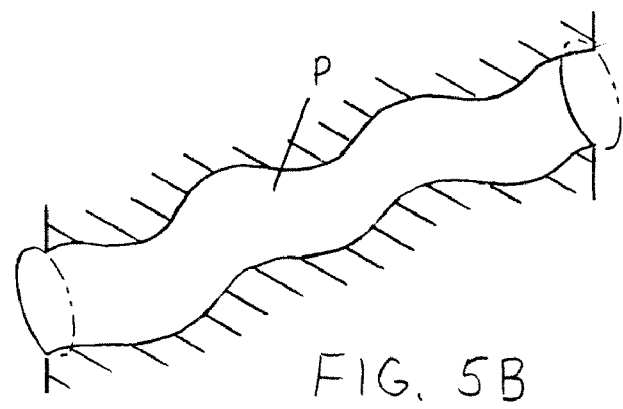
Figure 5C:
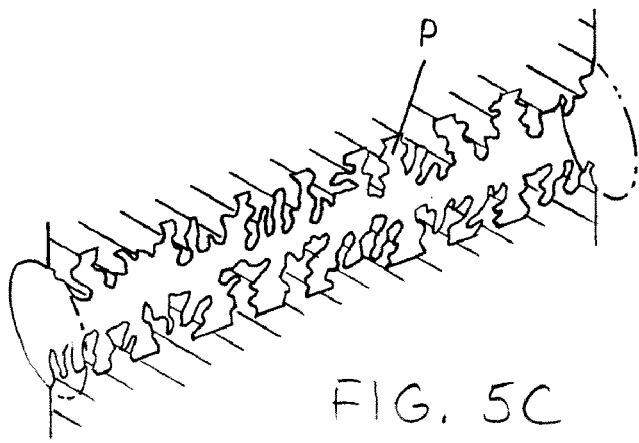
Figure 5D:
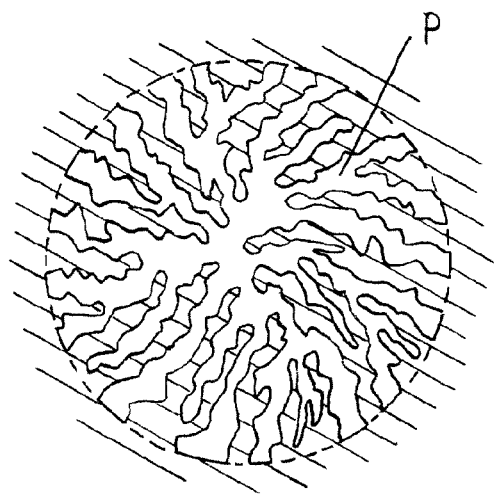
FIG. 5D is a cross-section of one non-limiting passageway that can be formed in a processing apparatus of the present invention.

Referring now to FIGS. 4, 4A, 4B, 4C and 55 the construction of a portion of the processing apparatus is illustrated. The portion illustrated is the middle portion; however, other portions of the processing apparatus can be formed in a similar manner; however, this is not required. For instance, one or more portions of the processing apparatus can be at least partially a molded, machined and/or cast component. As also can be appreciated, the middle portion can be formed only partially by the construction illustrated in FIGS. 4, 4A, 4B, 4C and 5. Referring now to FIGS. 4 and 5, the middle portion can be at least partially formed of a plurality of metal layers 72 that are connected together by a laminating agent 74 (e.g., brazing metal, adhesive, etc.). The metal layers are illustrated as being the same thickness; however, this is not required. The laminating agent is also illustrated as having the same thickness; however, this is not required. The metal layers are illustrated as having a generally rectangular shape; however, it can be appreciated that one or more metal layers can have a different shape and/or size from one another and/or have a shape that is different from a rectangular shape. The middle portion is illustrated as including two passageways 64, 66; however, it can be appreciated that only one passageway or more than two passageways can exist in the middle portion and/or other portions of the processing apparatus. For examples, FIG. 4B illustrates a processing apparatus that includes two middle portions 60a and 60b that include more than two passageways on the middle portions. The two passageways in the middle portions are illustrated in FIG. 4 as spiraling through the middle portion; however, it can be appreciated that one or more passageways can be straight or have any other desired shape. As illustrated in FIGS. 4B and 4C, one or more passageways have a different shape from the passageways in FIG. 4. The two passageways are illustrated in FIG. 4 as having a generally constant cross-section shape and size along the length of the passageways; however, it will be appreciated that the cross-section shape and size along the length of one or more passageways can vary. As illustrated in FIGS. 4B and 4C, the passageways have a different cross-section shape and size along the length of the passageways. As illustrated in FIGS. 5A-D, various non-limiting cross-sectional shapes of one or more passageways P are illustrated. FIG. 5A illustrates a passageway having a generally cylindrical shape. FIG. 5B illustrates a passageway having a generally wave-shape and also having a non-uniform cross-sectional area along the length of the passageway, FIGS. 5C and 5D illustrate a passageway having a very complex cross-sectional shape. For example, the passageway can have a complexity that mimics the size and/or distribution of pores of a porous material. As such, particles, catalysts of various shapes, porosity size and/or pore distribution of particles and/or catalyst can be at least partially mimicked by the complex passageway. The complexity of the passageway shape is non-limiting. It can be appreciated that passageway shapes can be formed to simulate material flowing through a catalyst; however, this is not required.

Figure 5E:
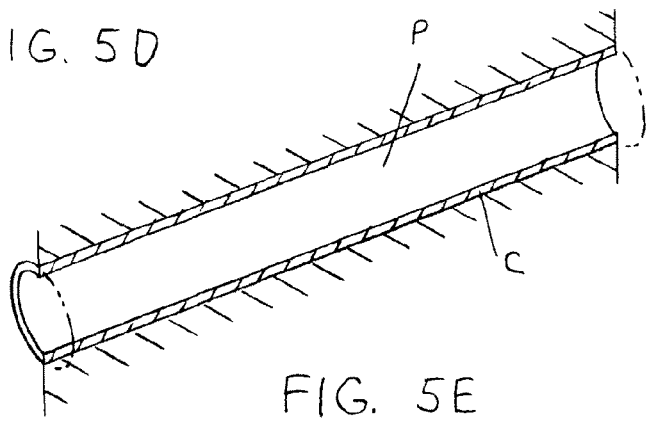
FIG. 5E is a sectional view of one non-limiting passageway that can be formed in a processing apparatus of the present invention that includes a catalyst secured to the inner wall of the passageway.
Figure 5F:
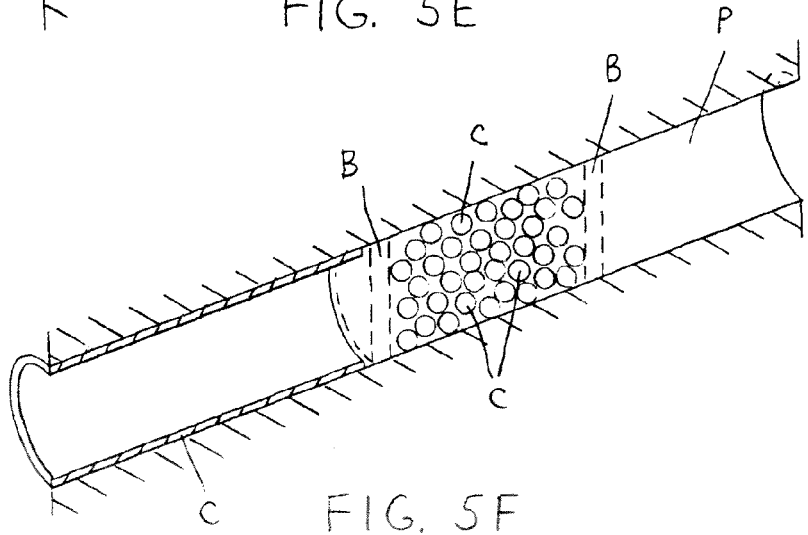
FIG. 5F is a sectional view of one non-limiting passageway that can be formed in a processing apparatus of the present invention that includes a catalyst positioned in a portion of the passageway.

Referring now to FIGS. 5E and 5F, a catalyst is illustrated as being positioned in passageway P. As previously mentioned, the one or more metal layers used to form the one or more passageways in the processing apparatus can be formed of a catalyst material; however, this is not required. When the one or more metal layers are used to form at least a portion of one or more passageways, the wall of the passageway can become a catalytic surface; however, this is not required. FIGS. 5E and 5F illustrate an alternative or additional arrangement to introduce catalyst in one or more portions of one or more passageways. FIG. 5E illustrates a passageway that includes a catalyst material C that is coated, plated and/or otherwise bonded to the inside surface of the passageway. The catalyst material can be a metal material; however, this is not required. The catalyst material can be formed of a single material or multiple materials. The passageway can have one type of catalyst material or multiple types of catalyst material along the length of the passageway. Referring now to FIG. 5F, the passageway includes a catalyst that is placed in one or more portions of the passageway. This catalyst can be a standard granular catalyst, particle catalyst, etc. The catalyst can be retained in a certain portion of the passageway by a barrier B (e.g., wire screen, slotted wall, mesh material, etc.); however, this is not required. As can be appreciated, both passageway arrangements as illustrated in FIGS. 5E and 5F can be used, and/or other and/or alternative arrangements can be used to place one or more catalyst in one or more portions of one or more passageways.

Referring now to FIGS. 4A-C, there are illustrated alignment structures 90 and construction structures 92. The alignment structures 90a, 90b as illustrated in FIG. 4A are in the form of a pin or bolt, respectively. The alignment structures are designed to be inserted in and/or through slots or openings in the metal layers. These slots or openings define the construction structures in the metal plates. As can be appreciated the alignment structure can be formed by structures other than a pin. In addition, the construction structures can take a form other than an opening or slot. The alignment structures 90 and construction structures 92 are used to orient one or more metal layers relative to one another in the middle portion and/or some other portion of the processing apparatus. As can be appreciated, one or more of the metal layers are not required to include construction structures. As can also be appreciated, one or more metal layers can include a different number of construction structures. Alignment structure 90a is in the form of a pin that traverses the complete thickness of the middle portion. As can be appreciated, the alignment structure need not traverse the complete thickness of the middle portion and/or any other portion of the processing apparatus. Alignment structure 90b is illustrated as including a threaded end 94. This threaded end can be used to secure one end of the alignment structure to a portion of the middle portion and/or any other portion of the processing apparatus, and/or to secure together one or more metal layers of the middle portion and/or any other portion of the processing apparatus; however, this is not required. The alignment structure 90b can also or alternatively be used to at least partially secure together one or more portions of the processing apparatus; however, this is not required. As can be appreciated, the threaded end of the alignment structure 90b can take on other or additional configurations to enable the end to be at least partially secured to and/or connect together one or more metal layers. The alignment structures 90 and construction structures 92 are illustrated as being positioned on the side regions of the metal layers; however, this is not required. The alignment structures 90 and construction structures 92 can be positioned in any region of the metal layers.

Referring now to FIG. 4C, one or more portions of the processing apparatus can include a cavity that is designed to receive one or more components; however, this is not required. For example, middle portion 60 includes a cavity 96 that is formed in one or more metal layers. Cavity 96 is designed to receive a tube portion 98. The tube portion is inserted into the cavity during the assembly of the processing apparatus. The tube can be formed of a special material, have a special configuration, include one or more catalysts, have a special interior configuration, etc.; however, this is not required. As can be appreciated, the cavity, when used, can have many configurations to at least partially accept many other types of components.

Referring again to FIG. 4C, the processing apparatus includes two middle portions 60a and 60b. As can be appreciated, the processing apparatus can include more than two middle portions or only one middle portion. The multiple middle portions can be formed of the same or different materials. For instance, one middle portion can include one type of catalyst and another middle portion may not include a catalyst or include a different catalyst. The multiple middle portions can have the same or different number of metal layers. The multiple middle layers can have the same or different size and/or shape.

Figure 6:
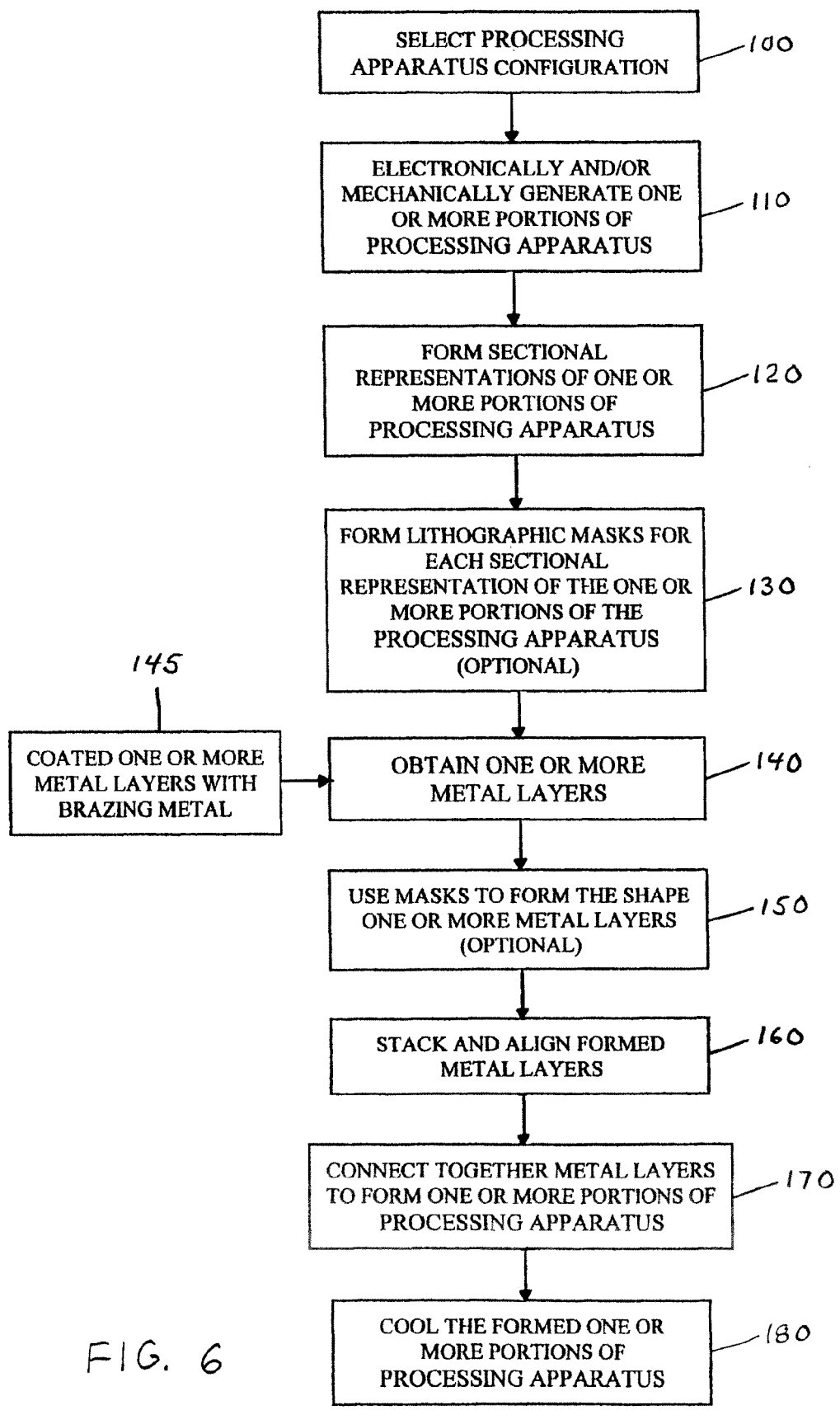
FIG. 6 is a flow chart illustrating a non-limiting method of forming one or more portions of a processing apparatus of the present invention.

Referring now to FIG. 6, one non-limiting process for manufacturing the middle portion and/or other portion of the processing apparatus is illustrated. As can be appreciated, many other manufacturing processes can be used to form one or more portions of the processing apparatus. As shown in FIG. 6, the first step of the manufacturing process 100 is to determine the desired shape of the processing apparatus or one or more portions of the processing apparatus. The drawing of the processing apparatus or one or more portions of the processing apparatus may be a mechanically drawn device and/or may be an electronically generated device.

Once the desired shape of the processing apparatus or one or more portions of the processing apparatus is determined, the shape of the processing apparatus or one or more portions of the processing apparatus is electronically entered 110, if not already, so as to form a three-dimensional computer-generated image of the processing apparatus or one or more portions of the processing apparatus. As can be appreciated, the complete processing apparatus can be electronically entered, or only the portions of the processing apparatus that are to be formed by the process can be electronically entered. For purposes of the following description, the top, bottom and middle portion of the processing apparatus are to be formed by this process. One software package that can be used to generate the three-dimensional computer generated processing apparatus is AutoCAD. Many other CAD software programs or other types of drawing programs can be used.

After the processing apparatus or one or more portions of the processing apparatus are electronically entered, the drawing is electronically sectioned or sliced into a plurality of cross-sections 120. The sections or slices of the processing apparatus or one or more portions of the processing apparatus are generally taken along a single axis (e.g., longitudinal, vertical, horizontal, etc.); however, this is not required. The thickness of each section or slice of the processing apparatus or one or more portions of the processing apparatus is representative of the thickness of the metal layer to be used to form the processing apparatus or one or more portions of the processing apparatus. The thickness of the metal layer can be a thin metal layer (i.e., metal foil layer) or be a thick layer. When the metal layer is very thin, many sections or slices of the processing apparatus or one or more portions of the processing apparatus need to be electronically generated. Each of the sections can include one or more holes or slots that will be used to orient the formed metal layers and also be used to maintain the position of the formed metal layers during heating and cooling of the metal layers; however, this is not required. Typically these holes or slots are positioned about the periphery of each section or slice of the processing apparatus or one or more portions of the processing apparatus; however, the holes or slots can be positioned in other locations. As can be appreciated, it is critical to the invention of the order of the above steps. For instance, one or more of the sections can be first formed and then one or more section can be formed together to create a three dimensional portion of the apparatus. It will also be appreciated that the one or more sections can be formed in 2 and/or 3 dimensional sections. The important step of the process thus described is that multiple sections are formed, either electronically or by accurate mechanical drawings to represent one or more sections of the apparatus.

Once the sections or slices of the processing apparatus or one or more portions of the processing apparatus are generated, a lithographic mask can be produced 130 for each metal layer to be used to form the processing apparatus or one or more portions of the processing apparatus. Each lithographic mask defines the features of each unique metal layer of the processing apparatus or one or more portions of the processing apparatus. The process for producing lithographic masks are well known in the art, thus will not be further described herein.

After the lithographic masks are produced for each metal layer of the processing apparatus or one or more portions of the processing apparatus, the metal layers are obtained 140 and one or more sides of one or more metal layers are coated 145 with a brazing metal; however, this is not required. As can be appreciated, another type of laminate can be used (e.g., adhesive, etc.). If one or more of the metal layers are to be connected together by an arrangement other than a lamination process (e.g., weld, solder mechanical connector, etc.), a laminate may not be applied to one or more of the metal layers. As can also be appreciated, the laminate coating on one or more metal layers can be applied to one or more metal layers prior to be at least partially processed by use of the lithographic masks; however, this is not required. The plurality of metal layers that are used to form the processing apparatus or one or more portions of the processing apparatus can be any type of metal. When forming the top and bottom portions of the processing apparatus, the metal layers, when used to form such portions, are typically made of a durable metal such as, but not limited to, stainless steel, nickel alloy, titanium alloy, etc.; however, this is not required. When forming one or more middle portions of the processing apparatus, a special metal may be used, such as a metal that catalyzes and/or facilitates in catalyzing a chemical reaction; however, this is not required. Many types of these special metals can be used such as, but not limited to, aluminum, cobalt, copper, gold, iridium, lithium, molybdenum, nickel, platinum, palladium, rhodium, ruthenium and/or silver, etc. As can be appreciated, the middle portion can be formed of the same type of metal layer or be formed of two or more different metal layers. For instance, half of the metal layers can be formed from gold and half of the metal layers can be formed from platinum. Many other or additional combinations can be used to enable materials passing through the processing apparatus to be exposed to one or more metals that catalyze and/or facilitate in catalyzing a chemical reaction as the materials pass through the processing apparatus or one or more portions of the processing apparatus. As can be appreciated, when the processing apparatus is not to be used as a reactor, none of the metal layers have to be formed of special metals; however, this is not required. As can also be appreciated, the top and/or bottom portion of the processing apparatus can be made of the same or similar materials as the one or more middle portions; however, this is not required. As can further be appreciated, the top and/or bottom portion of the processing apparatus can be formed of a single metal layer or a plurality of the same or different metal layers. As previously mentioned, the thickness of the metal layers used in the present invention can vary. When thin metal layers are used, the thickness is generally about 40-150 microns. As can be appreciated, other metal layer thicknesses can be used. The metal layer can be coated on one or both sides by a brazing metal or other type of laminate; however, this is not required. The coating of the brazing metal on the one or more metal layers when used, is typically by an electroplating process; however, other coating processes can be used. The coating thickness of the brazing metal is generally about 0.1-10 microns, and typically about 0.2-1.5 microns; however, other thicknesses can be used. The brazing metal can be any type of brazing material that can be used to successfully secure two adjacent positioned metal layers together and provide the desired connection strength. The brazing material for all the metal layers can be the same or can be different.

Once the coated metal layer is obtained, the metal layer can be subjected to lithographic micro-machining techniques and/or micro-machining techniques 150 to produce patterned metal layers that are ultimately used to form the processing apparatus or one or more portions of the processing apparatus. Some of the micro-machining techniques that can be used include photo-etching and reactive ion etching. This step is optional when one or more metal layers are formed by techniques other than lithographic techniques.

When thin metal layers are not used to form the apparatus, or one or more portions of the apparatus are not formed by thin metal layers, one or more other techniques can be used to form one or more of the metal layers; however, this is not required. Such other techniques include, but are not limited to, metal stamping, drilling, casting, ultrasonic cutting, water cutting, pressure forming, etching, laser cutting, bore cutting, etc. After the one or more metal layers are formed by this one or more other processes, a brazing metal, as described above, can be applied to such one or more metal layers; however, this is not required.

After the metal layers have been formed, the metal layers are aligned and stacked 160 to form the desired three-dimensional shape of the processing apparatus or one or more portions of the processing apparatus. The metal layers should be stacked so that a brazing metal and/or other type of laminate exist between each metal layer that is to be connected together by a laminate. This arrangement can be achieved in a number of different ways. One non-limiting way is to have one side of each of the metal layers to be coated with the brazing metal. The alignment of the metal layers can also be accomplished in a variety of ways. Typically, alignment pins or other fixed structures are used to align the multiple layers of metal layers; however, this is not required. The holes or slots in the metal layers are inserted onto the alignment pins thereby properly orienting the metal layers with respect to one another.

The aligned and stacked metal layers are then connected together as shown in step 170. Many processes can be used to secure two or metal layers together (e.g., lamination process, mechanical connections, welding, soldering, etc.). When a brazing process is used, a plurality of metal layers are subjected to heat so as to braze together the metal layers. Additionally or alternatively, pressure can be applied to a plurality of metal layers when securing together the plurality of metal layers by a lamination process and/or some other process. When using a brazing process, the heating of the coated metal layers at a proper elevated temperature for a sufficient time will result in the metal coating to soften and/or melt and flow between the metal layers. Typically, the brazing process is conducted under a vacuum; however, this is not required. The heating of the metal layers during a brazing process typically occurs in an inert atmosphere; however, this is not required. During the heating process, the metal layers expand. The alignment holes or slots can be used to maintain the metal layers in alignment during this heating process. Typically the alignment holes or slots in the metal layers can be sized and shaped to account for the expansion of the metal layers during heating; however, this is not require. In such an arrangement, when the metal layers are heated at or near their maximum temperature, wherein the brazing material is partially or fully liquified, the holes or slots line up relative to the alignment pins so as to form the desired shaped of the processing apparatus or one or more portions of the processing apparatus.

Once the metal layers are heated for a sufficient time, the formed processing apparatus or one or more portions of the processing apparatus can be cool as illustrated in step 180. This step can be skipped when there is no heating of the metal layers. When the metal layers are heated and then cooled during a brazing process, the brazing material solidifies thereby locking the metal layers in position relative to one another. The alignment holes or slots in the metal layers, when used, can be sized and shaped so as to allow the locked together metal layers to contract during cooling; however, this is not required. Typically, the cooling occurs in an inert atmosphere; however, this is not required. The use of the above method to manufacture a processing apparatus or one or more portions of the processing apparatus can result in a cost-effective process to manufacture a processing apparatus or one or more portions of the processing apparatus that has a specific design for use in a particular process.

As previous described, FIGS. 4 and 5 illustrate a section of a middle portion of a processing apparatus that can be formed by the process described in FIG. 6. Middle portion 60 includes a plurality of metal layers 72 that are connected together by a laminate 74 such as a brazing metal or adhesive.

The following example illustrates the manufacture of the middle portion of a processing apparatus or one or more portions of the processing apparatus that is formed of platinum in accordance with the present invention. The manufacturing process of the present invention can provide methods for fabricating a processing apparatus or one or more portions of the processing apparatus having three-dimensional passageway configurations that are difficult, if not impossible to make by conventional manufacturing processes.

The first part of the manufacturing process involves the generation of a three-dimensional computer model of the middle portion of the processing apparatus. The computer-generated model of the middle portion is divided into a plurality of sections that are cut parallel to the longitudinal axis of the middle portion. The thickness of the sections is substantially uniform and reflects the thickness of the metal layer to be used to make the middle portion. Guide holes or slots are also inserted for each section. The number, size and shape of the guide holes or slots are selected to achieve the proper orientation of the metal layers during the heating and cooling of the metal layers.

In one non-limiting example, the metal layers used to form the middle portion include thin metal platinum layers having a thickness of about 30-150 microns. These thin metal layers are coated on at least one side with a thin metal electroplated layer of a brazing metal having a thickness of about 0.1-10 microns. Non-limiting examples of brazing metals for the metal coating include nickel-silver alloys. A specific example of a coated metal layer for use in manufacturing the middle portion of the processing apparatus is a platinum metal layer coated on one side with an electroplated nickel-silver alloy coating wherein the thickness of the platinum metal layer is about 77 microns, the thickness of the nickel-silver alloy coating is about 1 micron and the total thickness of the coated thin metal layer is about 78 microns. In this example, the sliced sections of the computer generated middle portion of the processing apparatus would represent sections having a thickness of about 78 microns. The middle portion would thus be formed from about 100-3000 coated thin metal layers.

Each of the coated thin metal layers can be then chemically etched to match a specific section of a computer generated section of the middle portion. Photo-masks can be produced for etching each of the metal layers. Each metal layer can be processed using standard photo-etching techniques and can be etched in such a way that the cross-sectional shape of the etched walls for each metal layer is perpendicular to the top and bottom surfaces of the metal layer (commonly referred to as straight sidewalls).

Once all the metal layers are etched, the metal layers can be stacked together in order to form the complete middle portion or a portion of the middle portion. The guide holes or slots in the tin metal layers can be used to orient the thin metal layers on guide pins, such as, but not limited to, graphite pins. The thin metal layers can be coated such that a nickel-silver brazing metal coating existed between each metal layer. The stacked thin metal layers can then be bonded together by a vacuum brazing process; however, this is not required. During the brazing process, the layered assembly can be heated in an inert and/or oxygen-free atmosphere to a temperature of 100-1300° C. for about 20-75 minutes, which can cause the coated nickel-silver alloy coating to flow thereby wetting the surfaces of the platinum thin metal layers. The temperature and time of heating should be selected to allow the nickel-silver brazing metal to generally uniformly flow and connect the thin metal layers of platinum together at substantially all the contact points. The brazed layers of platinum thin metal layers can be then cooled in an inert atmosphere for about 1-3 hours and then removed. The formed middle portion can then be removed from the guide pins and then inspected for quality control purposes to determine if the formed middle portion has been properly formed in accordance with the desired specifications.

Figure 7:
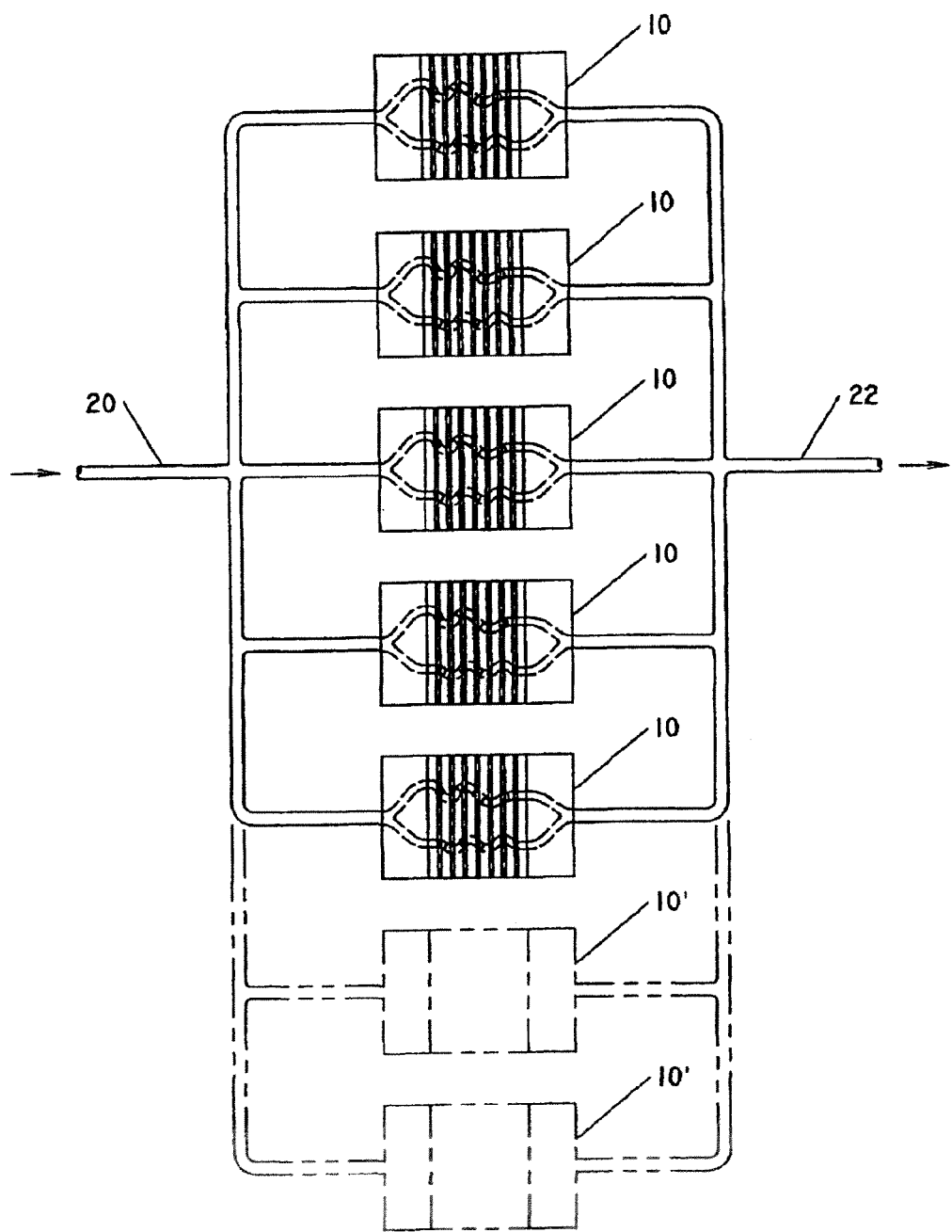
FIG. 7 is a graphical illustration of a plurality of processing apparatuses of the present invention positioned in series in a chemical process.

Referring now to FIG. 7, there is illustrated a plurality of processing apparatuses 10 connected between pipes 20 and 22. FIG. 7 illustrates that the number of processing apparatuses used in a process can be easily increased or decreased depending on the desired conditions. For instance, when the processing apparatus is in the form of micro-reactors, the number of micro-reactors used in a particular chemical process can be easily increased or decreased depending on present production rates of a chemical compound. In addition one or more of the micro-reactors can be taken out of service without having to shut down the chemical process. For example if a line to one of the micro-reactors becomes clogged or the catalyst in one micro-reactor becomes fouled or spent, the pipeline feeding the particular micro-reactor could be shut off and the micro-reactor could then be replaced or pipes feeding the micro-reactor could be serviced without having to shut down the complete chemical process. As such, one of the micro-reactors can be taken out of service, and/or one or more of micro-reactors 10' can be placed in service so that little or no interruption of the chemical process occurs. In prior reactor systems, wherein a single large reactor was used, the chemical process was typically terminated so that the reactor could be serviced (e.g., cleaned, replace catalyst, etc.). The use of the micro-reactors of the present invention can be used to enable a chemical process to continue without having to shut down one or more micro-reactors when in need of service. As can be appreciated, this same concept can be used for a processing apparatus in a form other than a micro-reactor.

Figure 8:
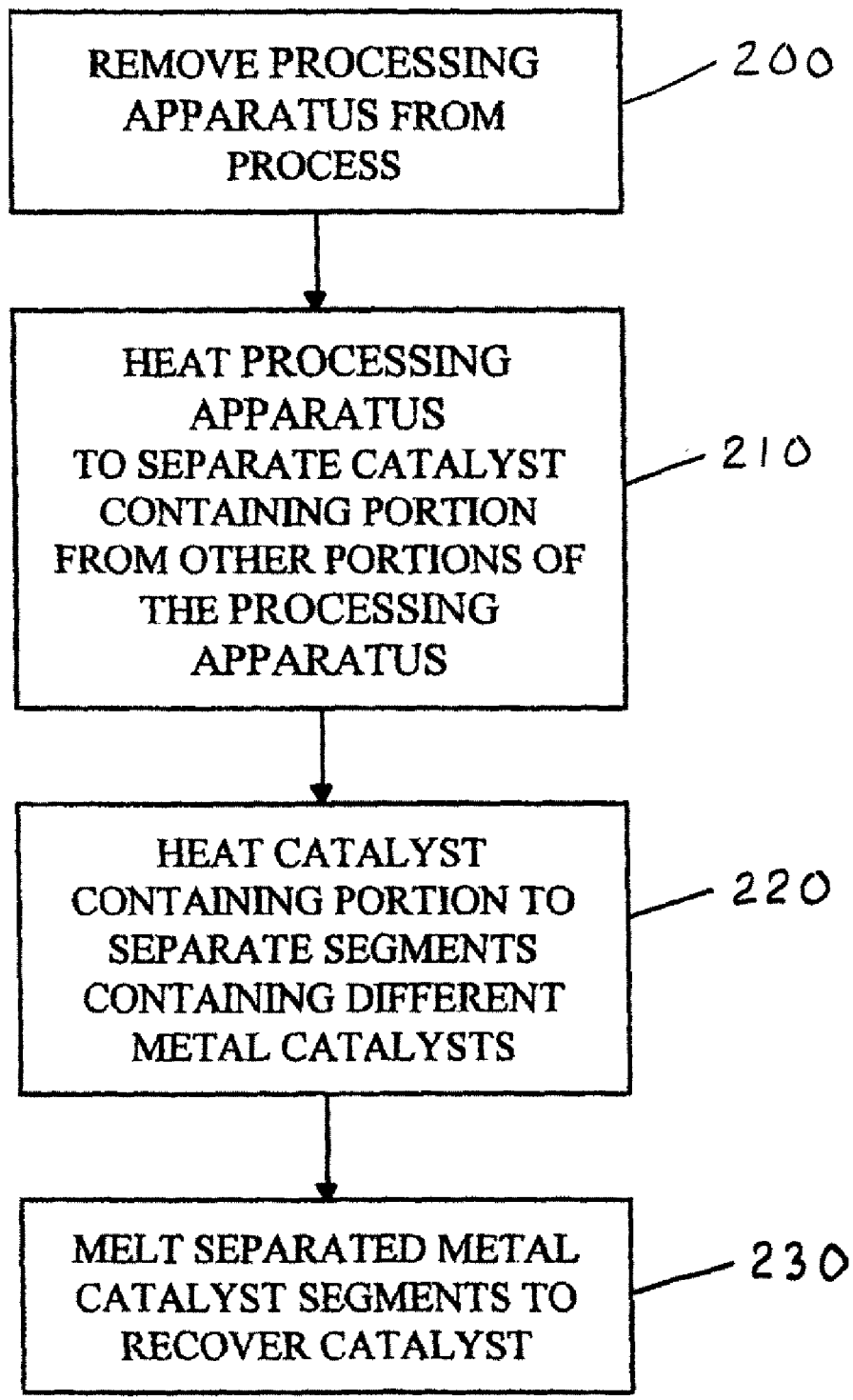
FIG. 8 is a flow chart illustrating a non-limiting method of recovering metal catalyst from the middle portion of a processing apparatus of the present invention.

Referring now to FIG. 8, there is illustrated a flow chart for one non-limiting process of recovering a catalyst in one or more portions of the processing apparatus, when a catalyst is used in the processing apparatus. When the processing apparatus is formed of a top portion, a bottom portion and one or more middle portions, the one or more middle portions can include a catalyst. In many types of chemical reactions, the catalyst may be a precious metal that is highly desirable to recover. Consequently, once the catalyst is spent or fouled, past reactors that included the valuable catalyst were generally sent to a recovery facility to recover the precious metal of the catalyst. Typically, the whole prior art reactor was melted down and the precious metal was then separated by expensive and time consuming techniques. Other prior art recovery techniques included exposing the prior art reactor to high energy plasma to melt the prior art reactor and/or catalyst support to thereby recover the catalyst. This process is also time consuming and expensive. The processing apparatus of the present invention can be designed to overcome the past difficulties and the high costs associated with valuable catalyst recovery. Referring now to FIG. 8, the first step 200 is to remove the processing apparatus from a chemical process line. Once the processing apparatus is removed from the process line, the processing apparatus is disassembled. As illustrated in FIGS. 1, 2A and 2B, the top and bottom portions of the processing apparatus can be secured together at flanges 44, 54 by a brazing metal 80 and/or by other or additional arrangement. In practice, when a brazing metal is used, the melting point of the brazing metal is less than the melting point of the brazing metal that secures together the metal layers of the middle portion, and the top portion and bottom portions if one or both of these portions are formed from metal layers. By selecting a brazing metal having this lower melting temperature, the processing apparatus can be heated to or slightly above the melting point of brazing metal 80 to enable the top and bottom portions to be separated from one another without causing any of the metal layers of the middle portion, top portion and/or bottom portion to separate. This is step 210 as shown in FIG. 8. If the top and bottom portions of the processing apparatus are mechanically connected together, this heating step can be ignored.

As shown in FIG. 3, the middle portion of the processing apparatus is connected to the top portion by a laminate 82, such as a brazing metal, and to the bottom portion by laminate 84, such as a brazing metal. The middle portion can be connected to the top and/or bottom portion by a laminate such as brazing metal; however, this is not required. For instance, the middle portion can be encapsulated between the top and bottom portion as shown in FIGS. 1, 2A and 2B without having to be connected to the top and/or bottom portions. When the middle portion is connected to the top and/or bottom portion as illustrated ion FIG. 3, the melting point of brazing metal 82 and 84, when used, is less than the melting point of the brazing metal that secures together the metal layers of the middle portion, and the top portion and bottom portions. The lower melting temperature of the brazing metal layers 82 and 84 allow the processing apparatus to be heated to or slightly above the melting point of brazing metal 82 and 84 to enable the top and bottom portions to be separated from one another without causing any of the metal layers of the middle portion, top portion or bottom portion to be separated. This step is again illustrated as step 210 of FIG. 8.

Once the middle portion of the processing apparatus is separated from the top and bottom portions of the processing apparatus, the metal in the one or more separated portions can be simply recovered by melting the individual portions as represented in step 230.

When the middle portion of one or more of the other portions of the micro-reactor are formed from thin metal layers of different metals, the different thin metal layers can be separated prior to the melting and recovery step 230; however, this is not required. This separation step is illustrated as step 220 of FIG. 8. For example if the middle portion is formed of two catalyst metals such as gold and platinum, the gold and platinum layers can be separated from one another prior to melting the metal layers. This separation can be accomplished by selecting a brazing metal that melts at a certain temperature. If, for example, the middle portion was formed of 1000 metal layers and metal layers 1-400 were formed of gold and metal layers 410-1000 were made of platinum, the brazing metal between layers 400 and 401 could be selected to have a lower melting point than the brazing metal used to connect together layers 1-400 and layers 401-1000. As such, the middle portion could be heated to the melting point or slightly above the melting point of the brazing metal between metal layers 400 and 401 so as to soften or melt this brazing metal without causing the brazing metal between metal layers 1-400 and 401-1000 to melt. Consequently, metal layers 1-400 and 401-1000 could be then separated from one another and then subsequently melted in separated facilities in accordance with step 230. As can be appreciated, the brazing metals selected to connect one or more portions of the processing apparatus together, and/or one or more metal layers together can be used to control the separation of various sections of the processing apparatus in an orderly manner to form and/or disassemble the processing apparatus as desired.

Figure 9:
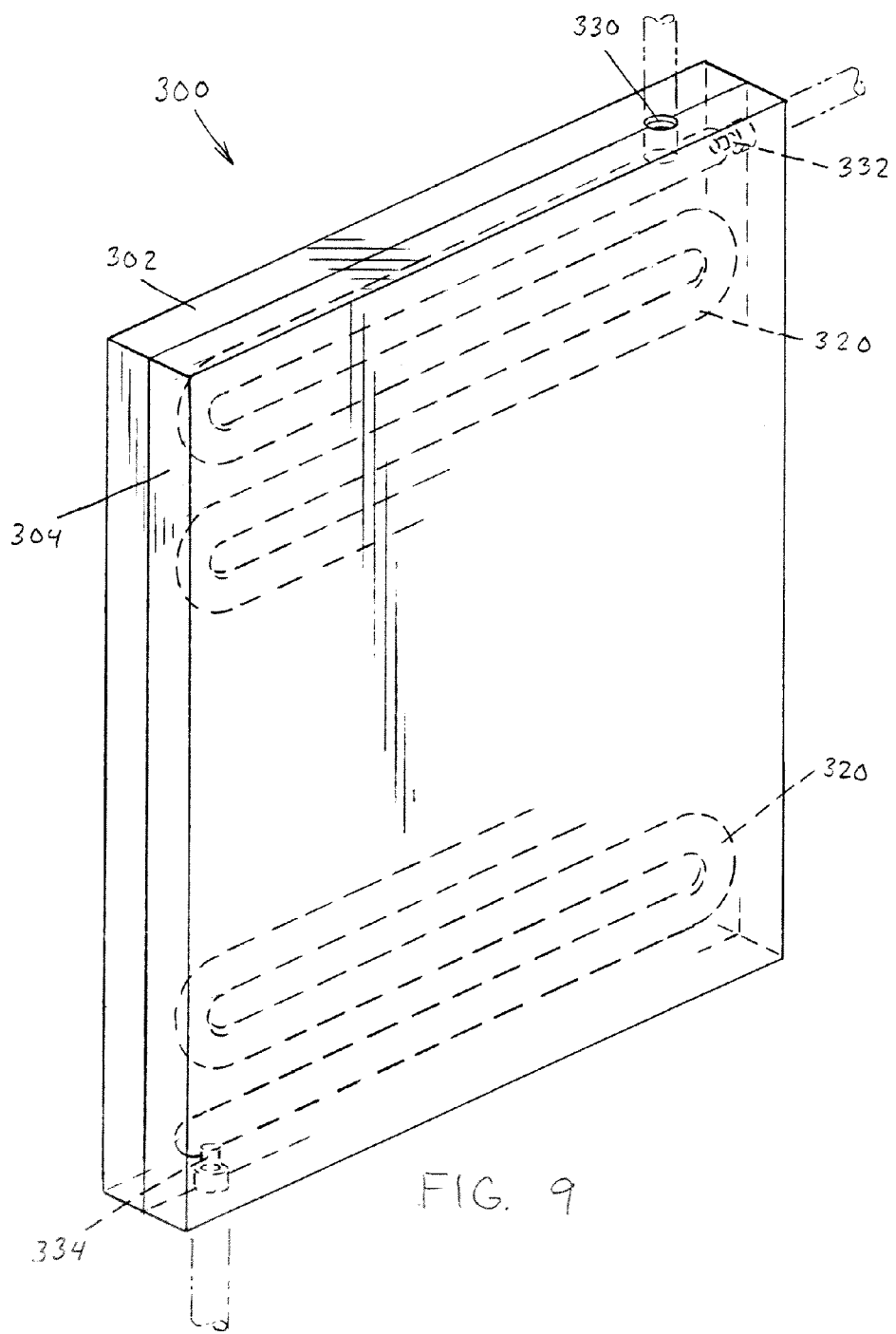
FIG. 9 is an elevation view of a non-limiting processing apparatus of the present invention in the form of a furnace element.
Figure 10:
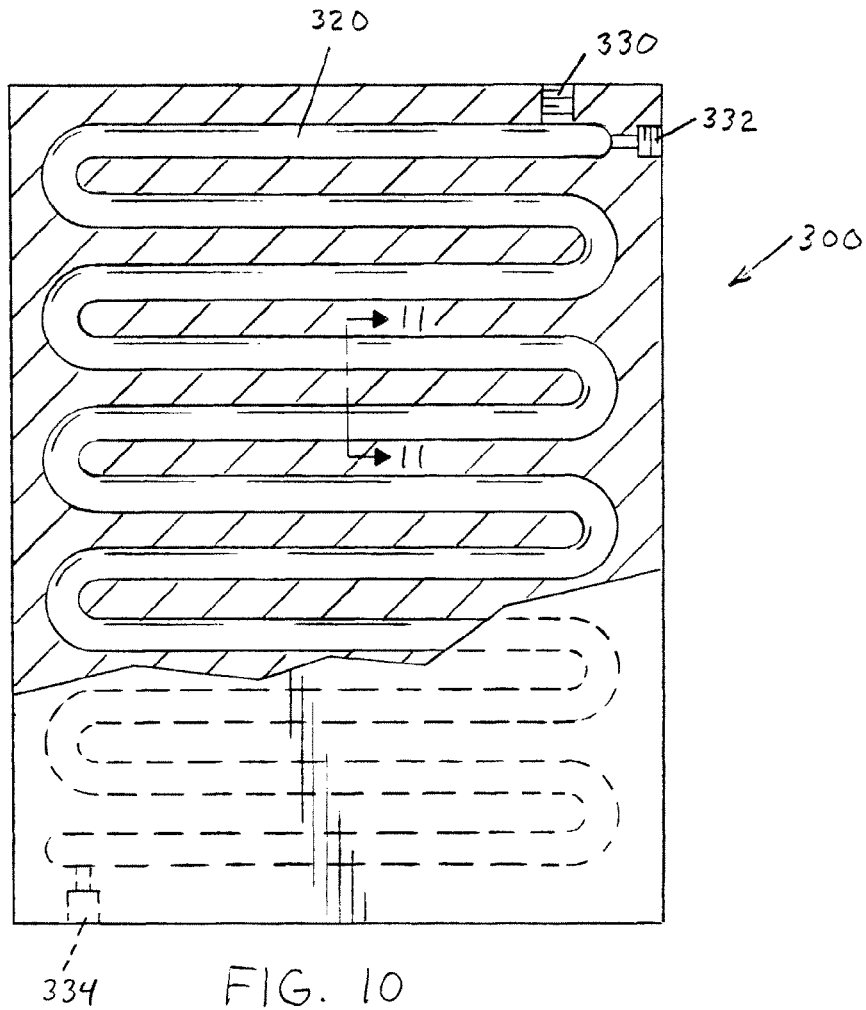
FIG. 10 is a cross-sectional view of the processing apparatus illustrated in FIG. 9.
Figure 11:
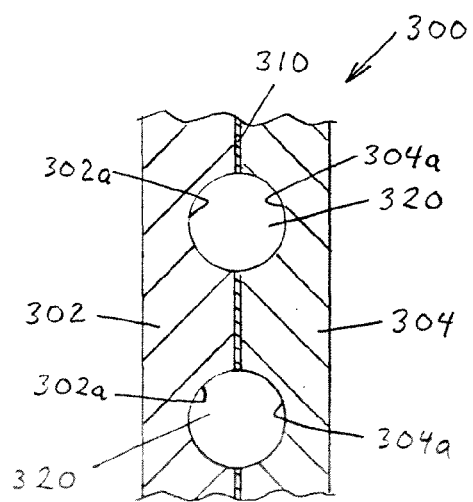
FIG. 11 is a cross-sectional view along line 11-11 of FIG. 10.

Referring now to FIGS. 9-22, there is illustrated another non-limiting embodiment of the processing apparatus in the form of a furnace element 300. As can be appreciated, the processing apparatus illustrated in FIGS. 9-22 can be used for other purposes. As illustrated in FIGS. 9-11, furnace element 300 is formed of two metal layers 302, 304 that are laminated together by a laminate 310. The lamination can be in the form of a high temperature adhesive (RTU silicon adhesive, ceramic adhesives, epoxy adhesives, polyimide adhesives, etc.). As used herein, high temperature means a temperature of at least about 100° C. As such, a high temperature adhesive is an adhesive that can maintain a bond at temperatures at least as high as about 100° C. As can be appreciated, when the processing apparatus is used in applications that do not involve high temperatures, other types of adhesives can be used. The lamination can also or alternatively be in the form of a brazing metal. The type of brazing metal used generally depends on the composition of metal layers 302, 304 and the temperature of operation of the furnace element. Non-limiting examples of brazing metals include, but not limited to, silver, silver-brass, silver-tin, silver-nickel lead-tin, nickel-brass, or nickel. The metal layers can be formed of the same or different material. For furnace applications, materials such as aluminum and copper have a high heat transfer rate, thus are ideal metals for such applications; however, such metals can be costly, thus not commercially viable in various applications. As such, less costly metals such as carbon steel or stainless steel can be used. As can be appreciated, other metals can also be used for one or more of the metal layers. The thickness of the metal layers can depend in part on 1) the number of metal layers used to form the furnace element and 2) the size and design of the furnace element. As illustrated in FIGS. 9-11, the furnace element is formed of two metal layers 302, 304. For the furnace element illustrated in FIGS. 9-11, the furnace element is for home use and has a volume of less than about 1200 cubic inches. As can be appreciated, larger or smaller furnace elements can be used. As also can be appreciated, the furnace element can be other sizes for non-home use (e.g., commercial use, etc.). For the furnace element for home use that has a volume of less than about 1200 cubic inches, the average thickness of the furnace element is about 0.2-5 inches (5080-127,000 microns), and generally about 0.4-2 inches (10,160-50,800 microns); however, other average thicknesses can be used. The metal layers are illustrated as having generally the same thickness; however, this is not required. The average thickness of metal layers 302, 304 is about 0.1-3 inches (2540-76,200 microns), typically about 0.2-1.5 inches (5080-38,100 microns), and even more typically about 0.25-0.75 inch (6350-19,050 microns). As can be appreciated, many other thickness can be used for metal layers 302 and/or 304. As can be appreciated, if the furnace element is formed from thin metal layers, then the average thickness of the metal layers will typically be less and the number of metal layers used to form the furnace element will typically be greater. In addition, if thin metal layers are used, metal layers 304 and/or 302 may be formed of a plurality of thin metal layers that have been laminated together; however, this is not required. The metal layers are illustrated as having a shape of a generally rectangular prism; however, it can be appreciated that one or both of the metal layers can have other shapes.

As best shown in FIG. 10, a single passageway 320 serpentines through the middle of the furnace element. As can be appreciated, more than one passageway can exist in the furnace element. As also can be appreciated, passageway paths other than or in addition to a serpentine passageway can be used. If the furnace element includes two or more passageways, the passageways can have the same or different shaped pathways. Passageway 320 is illustrated as having a generally circular cross-sectional shape as illustrated in FIG. 11; however, it can be appreciated that other or additional cross-sectional shapes (e.g., polygonal, oval, etc.) can be used in one or more portions of the passageway. Passageway 320 is illustrated as having a generally constant cross-sectional size and shape along the length of the passageway; however, this is not required. For example, when one or more materials passing through the passageway increase or decrease in volume and/or pressure, the cross-sectional area of the passageway one or more regions of the passageway can be adjusted to accommodate for such volume change. In one specific example, natural gas and air can be directed into passageway 320 and be combusted to create heat. The combustion of the gasses in the passageway in combination with the increase in gas temperature causes pressure increases in the combustion region. If the cross-sectional area of the passageway is too small, a gas back-flow in the passageway may occur, thereby resulting in the improper operation of the furnace element. In addition or alternatively, it the cross-sectional area in the passageway is too small or to large, the proper and/or most efficient combustion of the gasses may not occur. As the gas temperature decreases downstream from the combustion region, the gas pressure may drop due to the decrease in the volume of the gas at a lower temperature. As such, the furnace element can be designed such that the cross-sectional area of the one or more passageways in the combustion region is larger than other portions of the one or more passageways; however, this is not required.

As illustrated in FIGS. 9 and 10, the furnace element 300 includes three ports 330, 332, 334 that are in fluid communication with passageway 320. Gas port 330 can be used to connect to a natural gas source and gas port 332 can be designed to connect to an air or oxygen source, or vice versa. Gas port 334 can be used to connect to an exhaust pipe to convey the combusted gasses from the furnace element. One or more of the ports can include connection arrangements to facilitate in connecting a pipe, tube, etc. to one or more of the ports; however, this is not required. As can also be appreciated, the furnace element can include a greater or lesser number of gas ports. For example, the natural gas and air and/or oxygen can be combined upstream from the furnace element, thus one port would be required to introduce gasses into the furnace element, in another example, one or more ports can be positioned downstream from the combustion region to introduce one or more fluids into the passageway. As can be appreciated, many number of different arrangements for ports and port locations on the furnace element can be used. One or more mixing elements can be included in one or more of the ports and/or in passageway 320 to facilitate in the mixing of the gasses in the furnace element; however, this is not required.

Referring again to FIG. 11, metal layers 302 and 304 include a groove or channel portion 302*a*, 304*a*. When the two metal layers are connected together, these two channels form passageway 320. As illustrated in FIG. 11, each of the two channels has generally the same shape and size; however, this is not required. For example, one metal layer could have a larger groove and/or different shaped groove from the other metal layer. In another example, one metal layer can include a groove and the other metal layer not include any type of groove. As can be appreciated, many other or additional arrangements can be used in the furnace element.

As can be appreciated, although the processing apparatus illustrated in FIGS. 9-11 was described as a furnace element, the processing apparatus could have other uses such as, but not limited to a reactor or micro-reactor, heat exchanger, etc. As can also be appreciated, materials other than or in addition to gasses can be flowed through the processing apparatus (e.g., liquids, liquid and solid mixtures, gas and liquid mixtures, etc.).

Figure 12:
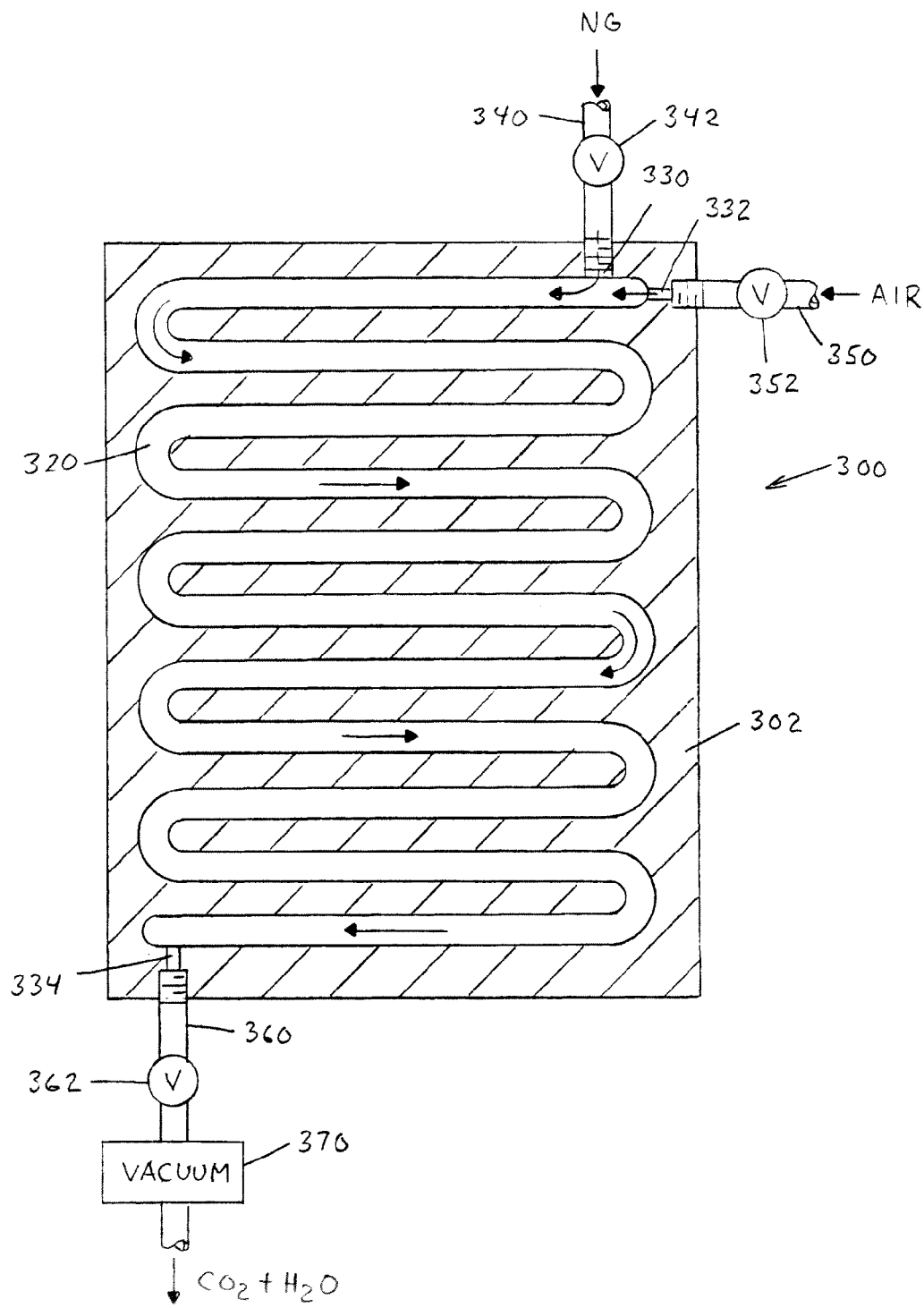
FIG. 12 is a cross-sectional view of another non-limiting processing apparatus of the present invention in the form of a furnace element.

Referring now to FIG. 12, a modification to the furnace element illustrated in FIGS. 9-11 is set forth. As shown in FIG. 12, a natural gas pipe 340 is connected to port 330 and an air pipe 350 is connected to port 332. Pipe 340 includes a valve 342 to control the flow rate of natural gas NG into passageway 320. Pipe 350 also includes a valve 352 to control the flowrate of air into passageway 320. As can be appreciated, the inclusion or use of valve 342 and/or valve 352 is not required. The arrows included in passageway 320 indicate the flow of gasses through the passageway. During the combustion of the natural gas in passageway 320, carbon dioxide and water are formed. An exhaust pipe 360 is connected to port 334. A valve 362 is connected to pipe 360 to control the flowrate of gasses exiting the furnace element. As can be appreciated, valve 362 is not required. A vacuum pump 370 or other type of device is illustrated as being in fluid connection with pipe 360 so as to pull a vacuum on pipe 360. The vacuum on pipe 360 can be used to increase the pressure drop through the passageway 320 of the furnace element so as to facilitate in the flow of gasses through the passageway. The amount of vacuum applied to pipe 360 can be controlled and/or set to at least partially adjust the flowrate of gasses though the passageway 320 of furnace element 300.

Figure 13:
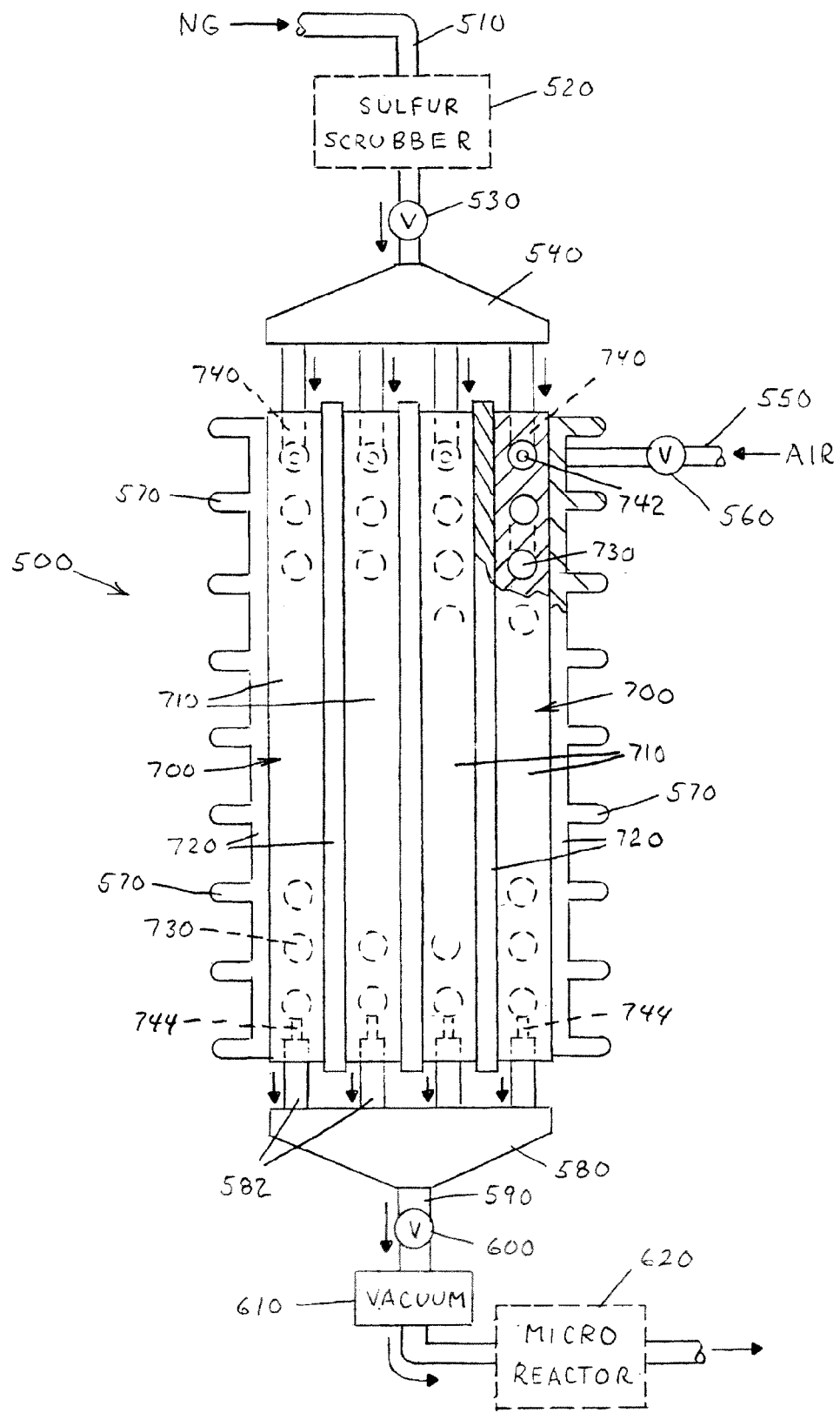
FIG. 13 is a cross-sectional view of still another non-limiting processing apparatus of the present invention in the form of a furnace element.

Referring now to FIG. 13, there is illustrated a furnace burner 500 that includes four (4) furnace elements connected together. This arrangement can be used to increase the BTU output. For example, if each furnace element was designed to generate about 10000 BTUs, and the furnace burner needed to generate about 50000 BTUs, five (5) furnace elements could be connected together as illustrated in FIG. 13 to generate the needed BTU output of the furnace burner. As can be appreciated, many other furnace element combinations can be used to generate the required BTU output. The furnace elements illustrated in FIG. 13 are generally about the same size and shape and are designed to generally output the same amount of BTUs, however, this is not required. For instance, different shaped or sized furnace elements can be connected together. The arrangement for forming each furnace element can be the same or similar or different to the arrangements used to form the furnace elements illustrated in FIGS. 9-11, 17-20 and 22. The particular arrangement of the furnace elements in FIG. 13 will be described in more detail below.

Referring again to FIG. 13, natural gas NG from a natural gas source flows through a pipe 510 to furnace burner 500. Prior to the natural gas reaching the furnace burner, one or more impurities (e.g., butane, carbon dioxide, ethane, hydrogen sulfide, nitrogen, pentane, propane, various alkanes, etc.) in the natural gas can be removed; however, this is not required. As illustrated in FIG. 13, a sulfur scrubber 520 is optionally connected between the natural gas supply and the furnace burner to remove some or all of the sulfur and/or sulfur compounds in the natural gas; however, this is not required. These types of scrubbers are commonly available such as scrubbers offered by Advanced Instruments Inc. The scrubber can be replaceable; however, this is not required. As can be appreciated, more than one scrubber can be used to remove impurities from the natural gas.

FIG. 13 illustrates the natural gas passing through a valve 530 that can be used to control the flow of natural gas into the furnace burner. As can be appreciated, the use of a valve is not required. A gas distributor 540 is illustrated as dividing the source of natural gas into one or more of the furnace elements. The gas distributor, when used, can include one or more mechanical and/or electrical devices (e.g., valves, orifices, screens, pipe sizes, etc.) to control the amount of natural gas that flows into each furnace element. As can be appreciated, the gas distributor can be designed to automatically control and/or be used to automatically control the flow of natural gas into one or more furnace elements; however, this is not required. Also or alternatively, the gas distributor can be designed to allow manual control of the flow of natural gas into one or more furnace elements; however, this is not required.

FIG. 13 illustrates air passing through an air pipe 550 and through valve 560 that can be used to control the flow of air into the furnace burner. As can be appreciated, the use of a valve is not required. An air distributor, not shown, can be used to divide the source of air into one or more of the furnace elements. The air distributor, when used, can include one or more mechanical and/or electrical devices (e.g., valves, orifices, screens, pipe sizes, etc.) to control the amount of air that flows into each furnace element. As can be appreciated, the air distributor can be designed to automatically control and/or be used to automatically control the flow of air into one or more furnace elements; however, this is not required. Also or alternatively, the air distributor can be designed to allow manual control of the flow of air into one or more furnace elements; however, this is not required. As can also be appreciated, one or more scrubbers can be used to remove impurities from the air and/or oxygen source; however, this is not required.

FIG. 13 illustrates that at least one of the furnace elements include one or more heat transfer structures in the form of a fin 570. As can be appreciated, only one of the furnace elements may include one or more heat transfer structures, one or more of the furnace elements may include one or more a heat transfer structures, or all of the furnace elements include one or more heat transfer structures. As can be appreciated, none of the furnace elements may include heat transfer structures. The one or more heat transfer structures can take on forms other than or in addition to a fin. The heat transfer structures are used to facilitate in transferring heat from one or more of the furnace elements to one or more materials (e.g., gas, liquid, and/or solid) flowing and/or positioned about the furnace burner. As such, the heat transfer structures are generally used to increase surface area for heat transfer. The heat transfer structures can be formed of the same or different material from the furnace elements. The heat transfer structures can have the same or different shape and/or size.

FIG. 13 illustrates an exhaust accumulator 580 that combines the exhaust gasses from the plurality of furnace elements into one exhaust pipe 590. The exhaust accumulator, when used, can include one or more mechanical and/or electrical devices (e.g., valves, orifices, screens, pipe sizes, etc.) to control the amount of exhaust gas that is received from each furnace element; however, this is not required. As can be appreciated, the exhaust accumulator can be designed to automatically control and/or be used to automatically control the flow of exhaust from one or more furnace elements; however, this is not required. Also or alternatively, the exhaust accumulator can be designed to allow manual control of the flow of exhaust from one or more furnace elements; however, this is not required. A valve 600 can also or alternatively be used to control of the flow of exhaust from one or more furnace elements and/or from the exhaust accumulator, when used; however, this is not required.

FIG. 13 illustrates a vacuum pump 610 or other type of device as being in fluid connection with pipe 590 so as to pull a vacuum on pipe 590. The vacuum on pipe 590 can be used to increase the pressure drop through valve 600, when used, through exhaust accumulator 580, when used, and/or through one or more of the furnace elements so as to facilitate in the flow of gasses through valve 600, exhaust accumulator 580, and/or one or more of the furnace elements. The amount of vacuum applied to pipe 590 can be controlled and/or set to at least partially adjust the flowrate of gasses though valve 600, exhaust accumulator 580, and/or one or more of the furnace elements.

FIG. 13 illustrates a micro-reactor 620 connected to pipe 590. The use of a micro-reactor is optional. The micro-reactor can be used to convert water and carbon dioxide, both by-products of the combustion of natural gas, into methanol and/or some other fuel. As can be appreciated, the one or more micro-reactors connected to pipe 590, when used, can be used to form other or additional compounds. For instance, if materials other than or in addition to natural gas and air are passed through, combusted and/or reacted in the processing apparatus, other or additional compounds may be formed by the one or more micro-reactors. As can be appreciated, the micro-reactor can be at least partially formed by processes similar to the processes for forming the processing apparatus that are disclosed in the present invention. As such, the micro-reactor, when used, can be formed of two or more metal layers that have been laminated together; however, this is not required. Many different processes can be used for form methanol from carbon dioxide and water. Non-limiting examples are disclosed in U.S. Pat. Nos. 3,959,094; 4,894,394; 5,037,619; 5,063,250; 5,310,506; 5,312,843; 5,342,702; 5,344,848; 5,416,245; 5,472,986; 5,496,859; 5,690,482; 5,767,165; 5,770,630; 5,980,782; 5,998,489; 6,005,011; 6,117,916; 6,156,234; 6,171,574; 6,191,174; 6,214,314; 6,218,439; 6,353,133; 6,736,955; all of which are incorporated herein by reference. The micro-reactor can be at least partially formed of or include one or more oxidation catalysts (e.g., chromium-aluminum alloy, copper, copper-chromium alloy, molybdenum, nickel, palladium, platinum, rhodium, ruthenium, silver, vanadium, vanadium-phosphate, etc.). When the micro-reactor includes one or more catalysts, the one or more catalysts can be supported on gamma and/or alpha alumina, and/or silica; however, this is not required.

Referring now to the four (4) furnace elements 700 in furnace burner 500, each furnace element includes a metal layer 710 and two metal layers 720. As illustrated in FIG. 13, one metal layer 720 is laminated to each side of metal layer 710. As also illustrated in FIG. 13, two metal layers 710 can share one metal layer 720; however, this is not required. The lamination can be the form of a high temperature adhesive (RTU silicon adhesive, ceramic adhesives, epoxy adhesives, polyimide adhesives, etc.). The lamination can also or alternatively be in the form of a brazing metal. The type of brazing metal when used generally depends on the composition of metal layers 710, 720 and the temperature of operation of the furnace element. Non-limiting examples of brazing metals include, but not limited to, silver, silver-brass, silver-tin, silver-nickel, lead-tin, nickel-brass, or nickel. The metal layers 710, 720 can be formed of the same or different material. Non-limiting examples for the metal used in the metal layers includes, but is not limited to, aluminum, aluminum alloys, copper, copper alloys, carbon steel and/or stainless steel; however, it will be appreciated that other metals can also be used. The thickness of the metal layers can depend in part on 1) the number of metal layers used to form the furnace element and 2) the size and design of the furnace element. As illustrated in FIG. 13, the furnace element is for home use and each furnace element has a volume of less than about 1200 cubic inches. As can be appreciated, larger or smaller furnace elements can be used. As also can be appreciated, the furnace element can be other sizes for non-home use (e.g., commercial use, etc.). For furnace elements for home use that has a volume of less than about 1200 cubic inches, the average thickness of the furnace element is about 0.2-5 inches (5080-127,000 microns), and generally about 0.4-2 inches (10,160-50,800 microns); however, other average thicknesses can be used. The metal layers are illustrated as having different thickness; however, the thicknesses can be the same. Generally the thickness of metal layer 710 is at least about 25% greater than the thickness of metal layer 720. In one non-limiting arrangement, the average thickness of metal layer 710 is about 0.1-3 inches (2540-76,200 microns), typically about 0.2-1.5 inches (5080-38,100 microns), and even more typically about 0.25-0.75 inch (6350-15,050 microns). In another non-limiting arrangement, the average thickness of metal layer 720 is about 0.05-2 inches (1270-50800 microns), typically about 0.075-1 inch (1905-25400 microns), and more typically about 0.08-0.5 inch (2032-12,700 microns). As can be appreciated, many other thickness can be used for metal layers 710 and/or 720. As can be appreciated, if furnace element is formed from thin metal layers, then the average thickness of the metal layers will typically be less and the number of metal layers used to form the furnace element will typically be greater. In addition, if thin metal layers are used, metal layers 710 and/or 720 may be formed of a plurality of thin metal layers that have been laminated together; however, this is not required. The metal layers as illustrated as having a shape of a generally rectangular prism; however, it can be appreciated that one or both of the metal layers can have other shapes.

A single passageway 730 serpentines through the middle of each furnace element 700. As can be appreciated, more than one passageway can exist in one or more furnace elements. As also can be appreciated, passageway paths other than or in addition to a serpentine passageway can be used in one or more furnace elements. If one or more furnace element includes two or more passageways, the passageways can have the same or different shaped pathways. Passageway 730 can have a generally circular cross-sectional shape; however, it can be appreciated that other or additional cross-sectional shapes (e.g., polygonal, oval, etc.) can be used in one or more portions of the passageway of one or more of the passageways. Passageway 730 is illustrated as having a generally constant cross-sectional size and shape along the length of the passageway in each furnace element; however, this is not required. For example, when one or more materials passing through the passageway of one or more furnace elements increase or decrease in volume and/or pressure, the cross-sectional area of one or more passageways one or more regions of the one or more passageways can be adjusted to accommodate for such volume change. For example, when natural gas NG and air are directed into passageways 730 and are combusted to create heat, the combustion of the gasses in the passageways in combination with the increase in gas temperature causes the pressure to increase in the combustion region of each of the passageways. If the cross-sectional area of one or more of the passageways is too small, a gas backflow in one or more passageways may occur, thereby resulting in the improper operation of one or more of the furnace elements. In addition or alternatively, it the cross-sectional area in one or more passageways is too small or to large, the proper and/or most efficient combustion of the gasses may not occur in one or more of the furnace elements. As the gas temperature decreases downstream from the combustion region, the gas pressure may drop due to the decrease in the volume of the gas at a lower temperature. As such, one or more of the furnace elements can be designed such that the cross-sectional area of the one or more passageways in the combustion region is larger than other portions of the one or more passageways; however, this is not required.

As illustrated in FIG. 13, each furnace element 700 includes three ports 740, 742, 744 that are in fluid communication with passageway 730. Gas port 740 can be used to connect to gas pipe 542 from gas distributor 540. Gas port 742 can be designed to connect to pipe 550 that provides air and/or oxygen to the furnace elements. Gas port 744 can be used to connect to an exhaust pipe 582 to convey the combusted gasses from each furnace element to exhaust gas accumulator 580. One or more of the ports can include connection arrangements to facilitate in connecting a pipe, tube, etc. to one or more of the ports; however, this is not required. As can also be appreciated, each furnace element can include a greater or lesser number of gas ports. For example, the natural gas and air and/or oxygen can be combined upstream from one or more of the furnace elements, thus one port would be required to introduce gasses into one or more of the furnace elements. In another example, one or more ports can be positioned downstream from the combustion region to introduce one or more fluids into one or more of the passageways 730 of one or more of the furnace elements and/or to remove combusted gasses from one or more of the passageways 730. As can be appreciated, many number of different arrangements for ports and port locations on one or more of the furnace elements can be used. One or more mixing elements can be included in one or more of the ports and/or in passageway 730 of one or more of the furnace elements to facilitate in the mixing of gasses in one or more of the furnace elements; however, this is not required.

As illustrated in FIG. 13, metal layer 710 includes a groove or channel portion that traverses the complete thickness of metal layer 710. Metal layers 720 are illustrated as not including channels or grooves. When metal layers 720 are connected to each side of metal layer 710, passageway 730 is formed. As can be appreciated, many other or additional arrangements can be used to form one or more portions of the passageway 730 in one or more of the furnace elements. For example, metal layer 720 can include a channel or groove that is less than the thickness of the metal layer. In another example, metal layer 720 can include a slot or groove that is used to at least partially form passageway 730.

In operation, the processing apparatus illustrated in FIG. 13 can be used to generate heat in a furnace and also produce a fuel such as methanol from the exhaust gasses from the combustion of the natural gas. The basic furnace burner 500 includes the natural gas source, the air source, the gas distributor 540, the plurality of furnace elements 700, and the exhaust gas accumulator 580. The plurality of fins 570 can be used to increase heat transfer between the one or more furnace elements and the air moving over the surface of the furnace elements; however, this is not required. The vacuum pump 610 can be used to facilitate in drawing gasses through one or more passageways 730 in one or more of the furnace elements; however, this is not required. When one or more of the exhaust gasses are to be processed in one or more micro-reactor 620, a sulfur scrubber 520 can be used; however, this is not required.

Figure 20:
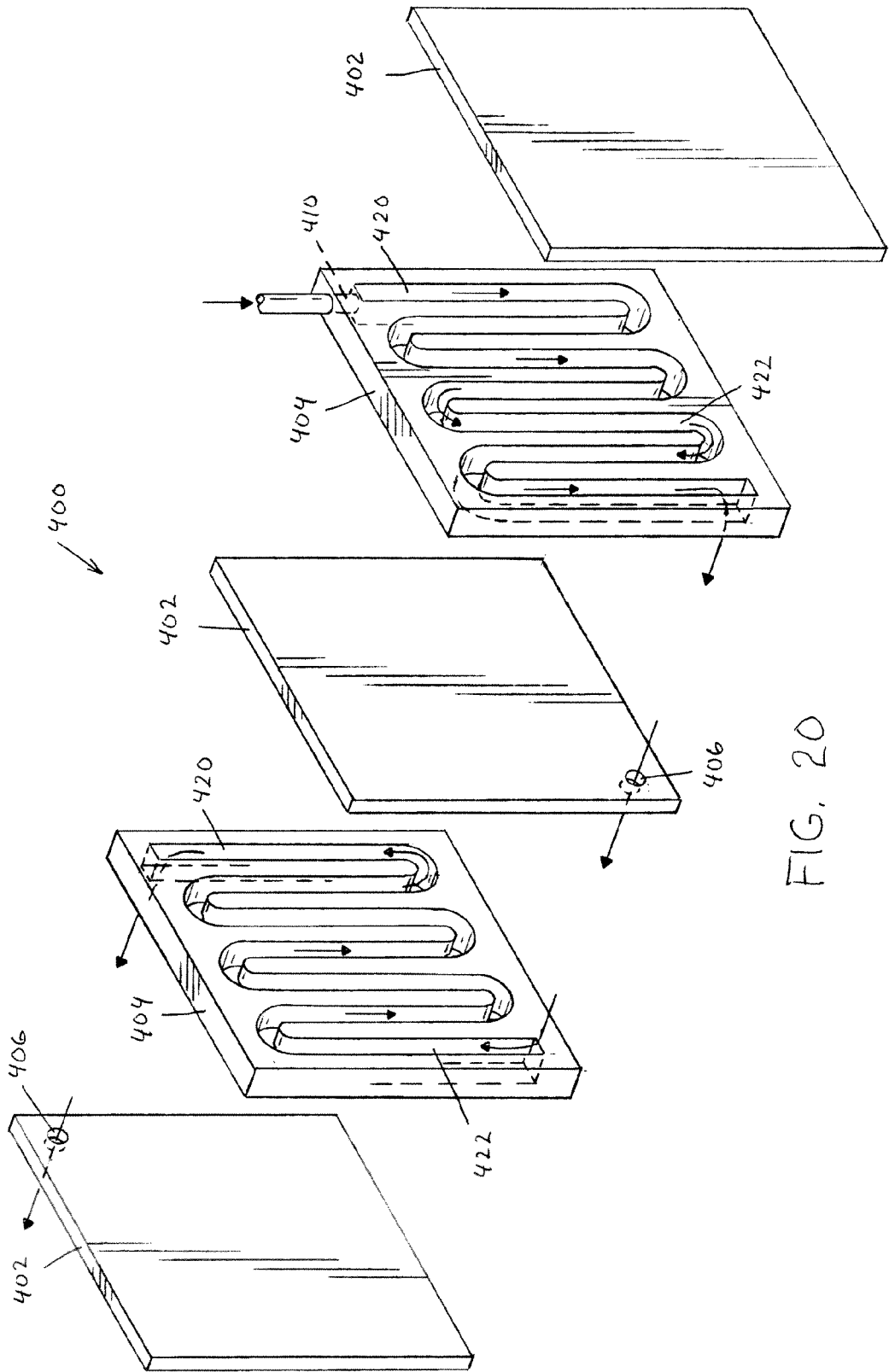
FIG. 20 is an exploded view of a portion of the processing apparatus as illustrated in FIG. 17.
Figure 21:
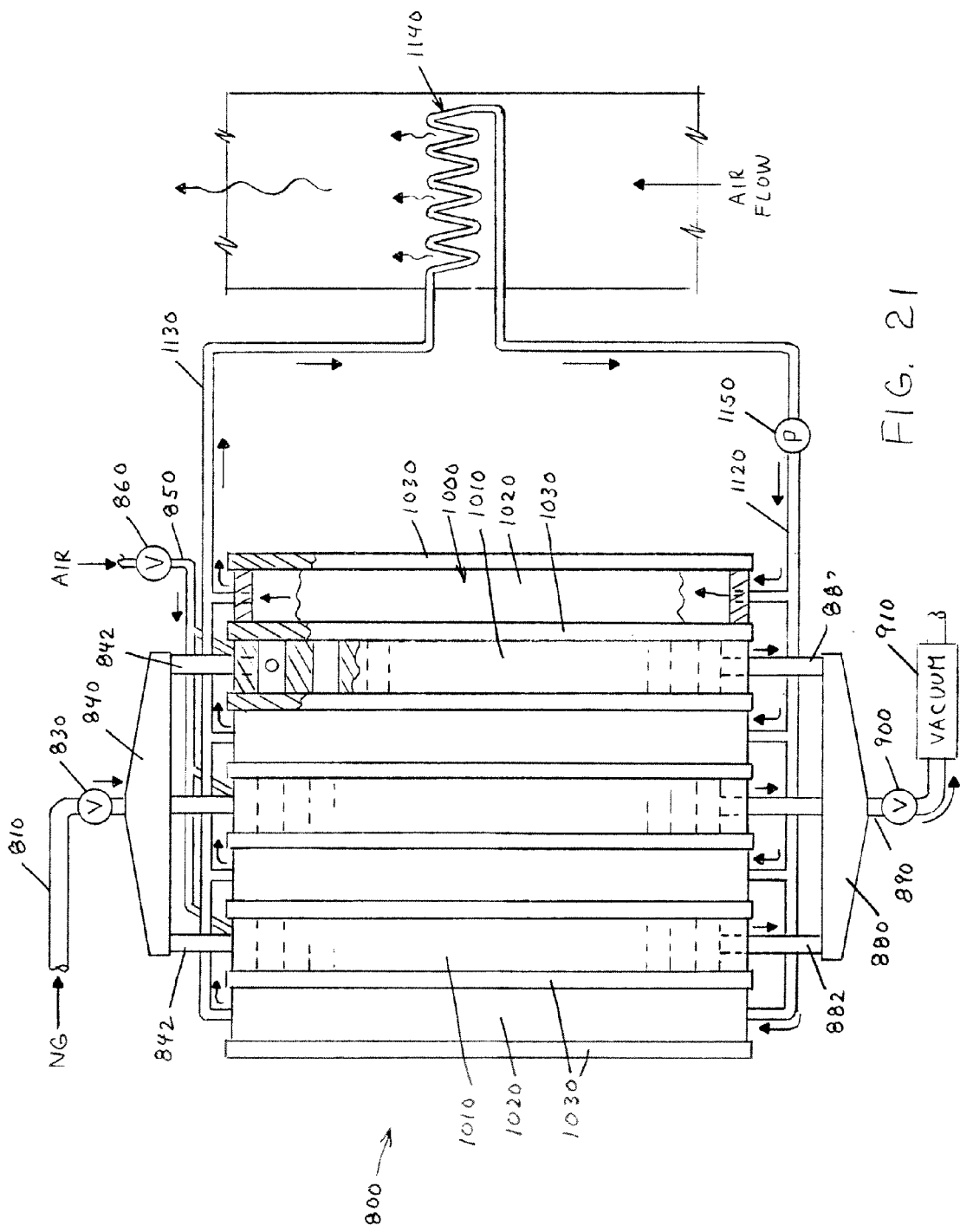
FIG. 21 is a cross-sectional view of still another non-limiting processing apparatus of the present invention in the form of a furnace element.
Figure 22:
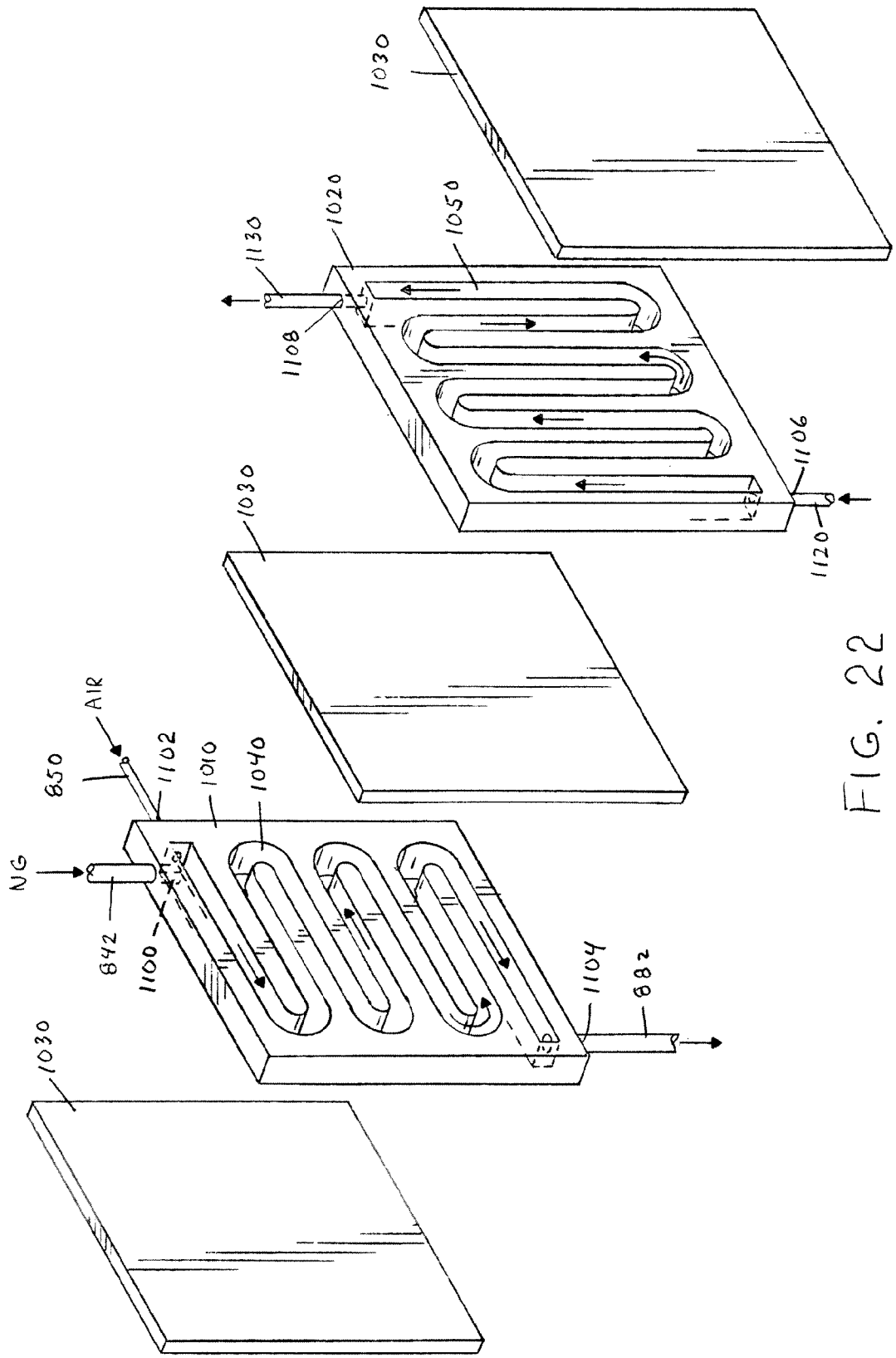
FIG. 22 is an exploded view of a portion of the processing apparatus as illustrated in FIG. 21; and, FIGS. 23-25 are elevation view of three non-limiting fluid mixing elements.

Referring now to FIGS. 21 and 22, there is illustrated another non-limiting furnace burner 800 that includes three (3) furnace elements connected together. This arrangement can be used to increase the BTU output. For example, if each furnace element was designed to generate about 15000 BTUs, and the furnace burner needed to generate about 60000 BTUs, four (4) furnace elements could be connected together as illustrated in FIG. 21 to generate the needed BTU output of the furnace burner. As can be appreciated, many other furnace element combinations can be used to generate the required BTU output. The furnace elements illustrated in FIG. 21 are generally about the same size and shape and are designed to generally output the same amount of BTUs, however, this is not required. For instance, different shaped or sized furnace elements can be connected together. The arrangement for forming each furnace element can be the same or similar or different to the arrangements used to form the furnace elements illustrated in FIGS. 9-11, 13, 17-20 and 22. The particular arrangement of the furnace elements in FIG. 21 will be described in more detail below.

Referring again to FIG. 21, natural gas NG from a natural gas source flows through a pipe 810 to furnace burner 800. Prior to the natural gas reaching the furnace burner, one or more impurities in the natural gas can be removed; however, this is not required. One or more sulfur scrubbers, not shown, can be optionally connected between the natural gas supply and the furnace burner to remove some or all of the sulfur and/or sulfur compounds in the natural gas; however, this is not required.

FIG. 21 illustrates the natural gas passing through a valve 830 that can be used to control the flow of natural gas into the furnace burner. As can be appreciated, the use of a valve is not required. A gas distributor 840 is illustrated as dividing the source of natural gas into one or more of the furnace elements. The gas distributor, when used, can include one or more mechanical and/or electrical devices to control the amount of natural gas that flows into each furnace element. As can be appreciated, the gas distributor can be designed to automatically control and/or be used to automatically control the flow of natural gas into one or more furnace elements; however, this is not required. Also or alternatively, the gas distributor can be designed to allow manual control of the flow of natural gas into one or more furnace elements; however, this is not required.

FIG. 21 illustrates air passing through an air pipe 850 and through valve 860 that can be used to control the flow of air into the furnace burner. As can be appreciated, the use of a valve is not required. An air distributor, not shown, can be used to divide the source of air into one or more of the furnace elements. The air distributor, when used, can include one or more mechanical and/or electrical devices to control the amount of air that flows into each furnace element. As can be appreciated, the air distributor can be designed to automatically control and/or be used to automatically control the flow of air into one or more furnace elements; however, this is not required. Also or alternatively, the air distributor can be designed to allow manual control of the flow of air into one or more furnace elements; however, this is not required. As can also be appreciated, one or more scrubbers can be used to remove impurities from the air and/or oxygen source; however, this is not required.

One or more of the furnace elements can include one or more heat transfer structures to facilitate in transferring heat from one or more of the furnace elements to one or more materials flowing and/or positioned about the furnace burner; however, this is not required. The heat transfer structures are generally used to increase surface area for heat transfer. The heat transfer structures can be formed of the same or different material from the furnace elements. The heat transfer structures can have the same or different shape and/or size.

FIG. 21 illustrates an exhaust accumulator 880 that combines the exhaust gasses from the plurality of furnace elements into one exhaust pipe 890. The exhaust accumulator, when used, can include one or more mechanical and/or electrical devices to control the amount of exhaust gas that is received from each furnace element; however, this is not required. As can be appreciated, the exhaust accumulator can be designed to automatically control and/or be used to automatically control the flow of exhaust from one or more furnace elements; however, this is not required. Also or alternatively, the exhaust accumulator can be designed to allow manual control of the flow of exhaust from one or more furnace elements; however, this is not required. A valve 900 can also or alternatively be used to control the flow of exhaust from one or more furnace elements and/or from the exhaust accumulator, when used; however, this is not required.

FIG. 21 illustrates a vacuum pump 910 or other type of device as being in fluid connection with pipe 890 so as to pull a vacuum on pipe 890. The vacuum on pipe 890 can be used to increase the pressure drop through valve 900, when used, through exhaust accumulator 880, when used, and/or through one or more of the furnace elements so as to facilitate in the flow of gasses through valve 900, exhaust accumulator 880, and/or one or more of the furnace elements. The amount of vacuum applied to pipe 890 can be controlled and/or set to at least partially adjust the flowrate of gasses though valve 900, exhaust accumulator 880, and/or one or more of the furnace elements.

A micro-reactor, not shown, can be connected to pipe 890. The use of a micro-reactor is optional. The micro-reactor can be used to convert water and carbon dioxide, both by-products of the combustion of natural gas, into methanol and/or some other fuel. As can be appreciated, the one or more micro-reactors connected to pipe 890, when used, can be used to form other or additional compounds.

Referring again to FIG. 21, there are three (3) furnace elements 1000 in furnace burner 800, each furnace element includes a metal layer 1010, a metal layer 1020, and three metal layers 1030. As illustrated in FIG. 21, one metal layer 1030 is laminated to each side of metal layers 1100 and 1020. As also illustrated in FIG. 21, metal layers 1010 and 1020 can share one metal layer 1030; however, this is not required. The lamination can be in the form of a high temperature adhesive. The lamination can also or alternatively be in the form of a brazing metal. The type of brazing metal, when used, generally depends on the composition of metal layers 1010, 1020, 1030 and the temperature of operation of the furnace element. The metal layers 1010, 1020, 1030 can be formed of the same or different material. The thickness of the metal layers can depend in part on 1) the number of metal layers used to form the furnace element and 2) the size and design of the furnace element. As illustrated in FIG. 21, the furnace element is for home use and each furnace element has a volume of less than about 1200 cubic inches. As can be appreciated, larger or smaller furnace elements can be used. As also can be appreciated, the furnace element can be other sizes for non-home use (e.g., commercial use, etc.). For furnace elements for home use that has a volume of less than about 1200 cubic inches, the average thickness of the furnace element is about 0.2-5 inches (5080-127,000 microns), and generally about 0.4-2 inches (10,160-50,800 microns); however, other average thicknesses can be used. The metal layers are illustrated as having different thickness; however, the thicknesses can be the same. Generally the thickness of metal layers 1010 and/or 1020 are at least about 25% greater than the thickness of metal layer 1030. In one non-limiting arrangement, the average thickness of metal layers 1010 and/1020 is about 0.1-3 inches (2540-76,200 microns), typically about 0.2-1.5 inches (5080-38,100 microns), and even more typically about 0.25-0.75 inch (6350-15,050 microns). In another non-limiting arrangement, the average thickness of metal layer 1030 is about 0.05-2 inches (1270-50800 microns), typically about 0.075-1 inch (1905-25400 microns), and more typically about 0.08-0.5 inch (2032-12,700 microns). As can be appreciated, many other thicknesses can be used for metal layers 1010, 1020 and/or 1030. As can be appreciated, if furnace element is formed from thin metal layers, then the average thickness of the metal layers will typically be less and the number of metal layers used to form the furnace element will typically be greater. In addition, if thin metal layers are used, metal layers 1010, 1020 and/or 1030 may be formed of a plurality of thin metal layers that have been laminated together; however, this is not required. The metal layers as illustrated as having a shape of a generally rectangular prism; however, it can be appreciated that one or both of the metal layers can have other shapes.

Referring now to FIG. 22, two passageways 1040, 1050 serpentine through the middle of each furnace element 1000. As can be appreciated, more than two passageways can exist in one or more furnace elements. As also can be appreciated, passageway paths other than or in addition to a serpentine passageway can be used in one or more furnace elements. The two or more passageways in each furnace element can have the same or different shaped pathways. Passageways 1040, 1050 can have a generally circular cross-sectional shape; however, it can be appreciated that other or additional cross-sectional shapes can be used in one or more portions of the passageway of one or more of the passageways. Passageways 1040, 1050 are illustrated has having a generally constant cross-sectional size and shape along the length of the passageway in each furnace element; however, this is not required. For example, when one or more materials passing through the passageway of one or more furnace elements increase or decrease in volume and/or pressure, the cross-sectional area of one or more passageways one or more regions of the one or more passageways can be adjusted to accommodate for such volume change. For example, when natural gas NG and air are directed into passageway 1040 of each furnace element and are combusted to create heat, the combustion of the gasses in the passageways in combination with the increase in gas temperature causes the pressure to increase in the combustion region of each of the passageways. If the cross-sectional area of one or more of the passageways is too small, a gas back-flow in one or more passageways may occur, thereby resulting in the improper operation of one or more of the furnace elements. In addition or alternative, it the cross-sectional area in one or more passageways is too small or to large, the proper and/or most efficient combustion of the gasses may not occur in one or more of the furnace elements. As the gas temperature decreases downstream from the combustion region, the gas pressure may drop due to the decrease in the volume of the gas at a lower temperature. As such, one or more of the furnace elements can be designed such that the cross-sectional area of the one or more passageways in the combustion region is larger than other portions of the one or more passageways; however, this is not required. Passageways 1040 and 1050 are illustrated as not being mirror images of one another; however, this is not required. As can be appreciated, any flow pattern for passageways 1040 and 1050 can be designed in one or more of the furnace elements.

As also illustrated in FIG. 22, passageway 1050 in metal layer 1020 is designed to convey a fluid that is used to absorb heat generated in passageway 1040. The fluid that flows through passageway 1040 can be a gas and/or liquid. Non-limiting examples of liquids and gasses include, but are not limited to, water, steam, oil, glycol, water-glycol mixtures, alcohol, water-alcohol mixtures, etc. As can be appreciated, a liquid flowing through passageway 1040 can be at least partially converted to a gas; however, this is not required.

As illustrated in FIG. 22, each furnace element 1000 includes five ports 1100, 1102, 1104, 1106, 1108. Ports 1100, 1102 and 1104 are in fluid communication with passageway 1040. Ports 1106 and 1108 are in fluid communication with passageway 1050. Gas port 1100 can be used to connect to gas pipe 842 from gas distributor 840. Gas port 1102 can be designed to connect to pipe 850 that provides air and/or oxygen to the furnace elements. Gas port 1104 can be used to connect to an exhaust pipe 882 to convey the combusted gasses from each furnace element to exhaust gas accumulator 880. One or more of the ports can include connection arrangements to facilitate in connecting a pipe, tube, etc. to one or more of the ports; however, this is not required. As can also be appreciated, each furnace element can include a greater or lesser number of gas ports. For example, the natural gas and air and or oxygen can be combined upstream from one or more of the furnace elements, thus one port would be required to introduce gasses into one or more of the furnace elements. In another example, one or more ports can be positioned downstream from the combustion region to introduce one or more fluids into one or more of the passageways 1040 of one or more of the furnace elements and/or to remove combusted gasses from one or more of the passageways 1040. One or more of the ports can include connection arrangements to facilitate in connecting a pipe, tube, etc. to one or more of the ports; however, this is not required. As can also be appreciated, each furnace element can include a greater or lesser number of gas ports. For example, the natural gas and air and/or oxygen can be combined upstream from one or more of the furnace elements, thus one port would be required to introduce gasses into one or more of the furnace elements. As can be appreciated, many number of different arrangements for ports and port locations on one or more of the furnace elements can be used. One or more mixing elements can be included in one or more of the ports and/or in passageway 1040 of one or more of the furnace elements to facilitate in the mixing of gasses in one or more of the furnace elements; however, this is not required. As can be appreciated, many number of different arrangements for ports and port locations on one or more of the furnace elements can be used. One or more mixing elements can be included in one or more of the ports and/or in passageway 1040 of one or more of the furnace elements to facilitate in the mixing of gasses in one or more of the furnace elements; however, this is not required. Port 1106 can be used to connect to a fluid pipe 1120 to enable a cooling fluid to flow into passageway 1050. Port 1108 can be used to connect to a fluid pipe 1130 to enable cooling fluid that is flowing in passageway 1050 to exit the fluid passageway. One or more of the ports can include connection arrangements to facilitate in connecting a pipe, tube, etc. to one or more of the ports; however, this is not required. As can also be appreciated, each furnace element can include a greater or lesser number of cooling fluid ports. In another example, one or more cooling fluid ports can be positioned downstream from the entrance to passageway 1050 to introduce one or more cooling fluids into one or more of the passageways 1050 of one or more of the furnace elements and/or to remove heated cooling fluid from one or more of the passageways 1050. As can be appreciated, many number of different arrangements for ports and port locations on one or more of the furnace elements can be used.

As illustrated in FIG. 22, metal layers 1010 and 1020 include a groove or channel portion that traverses the complete thickness of metal layers 1010 and 1020. Metal layers 1030 are illustrated as not including channels or grooves. When metal layers 1030 are connected to each side of metal layers 1010, 1020, passageway 1040, 1050, respectively, are formed. As can be appreciated, many other or additional arrangements can be used to form one or more portions of the passageways 1040 and/or 1050 in one or more of the furnace elements. For example, metal layer 1030 can include a channel or groove that is less than the thickness of the metal layer. In another example, metal layer 1030 can include a slot or groove that is used to at least partially form passageway 1040 and/or 1050.

Referring again to FIG. 21, furnace burner 800 includes a radiator arrangement 1140 and a pump 1150. Radiator arrangement can be any design that enables a fluid such as air to flow into and/or about at least a portion of the radiator so that heat can be transferred between the flowing fluid and the radiator arrangement. One non-limiting radiator arrangement is one that is similar to a radiator of a vehicle; however, this is not required. Pump 1150 is designed to pump and circulate fluid through fluid pipes 1120 and 1130 and radiator arrangement 1140. As can be appreciated, more than one pump can be used. Although not shown, fluid pipe 1120 and/or 1130 can include one or more valves to control the flow of fluid into and/or out of one to more furnace elements; however, this is not required.

In operation, the processing apparatus illustrated in FIG. 21 can be used to generate heat in a furnace. The processing apparatus could also be used to produce a fuel such as methanol from the exhaust gasses from the combustion of the natural gas; however, this is not required. The basic furnace burner 800 includes the natural gas source, the air source, the gas distributor 840, the plurality of furnace elements 1000, the exhaust gas accumulator 880, radiator 1140 and pump 1150. The vacuum pump 910 can be used to facilitate in drawing gasses through one or more passageways 1040 in one or more of the furnace elements 1000; however, this is not required. The furnace elements can be located in a location remote from the radiator arrangement, however, this is not required. For example, the furnace elements could be located outside a house or building and the radiator arrangement could be located inside a blower unit that is used to blow air over the radiator arrangement and convey the heated air through vents and/or registers throughout the home or building; however, this is not required.

Figure 14:
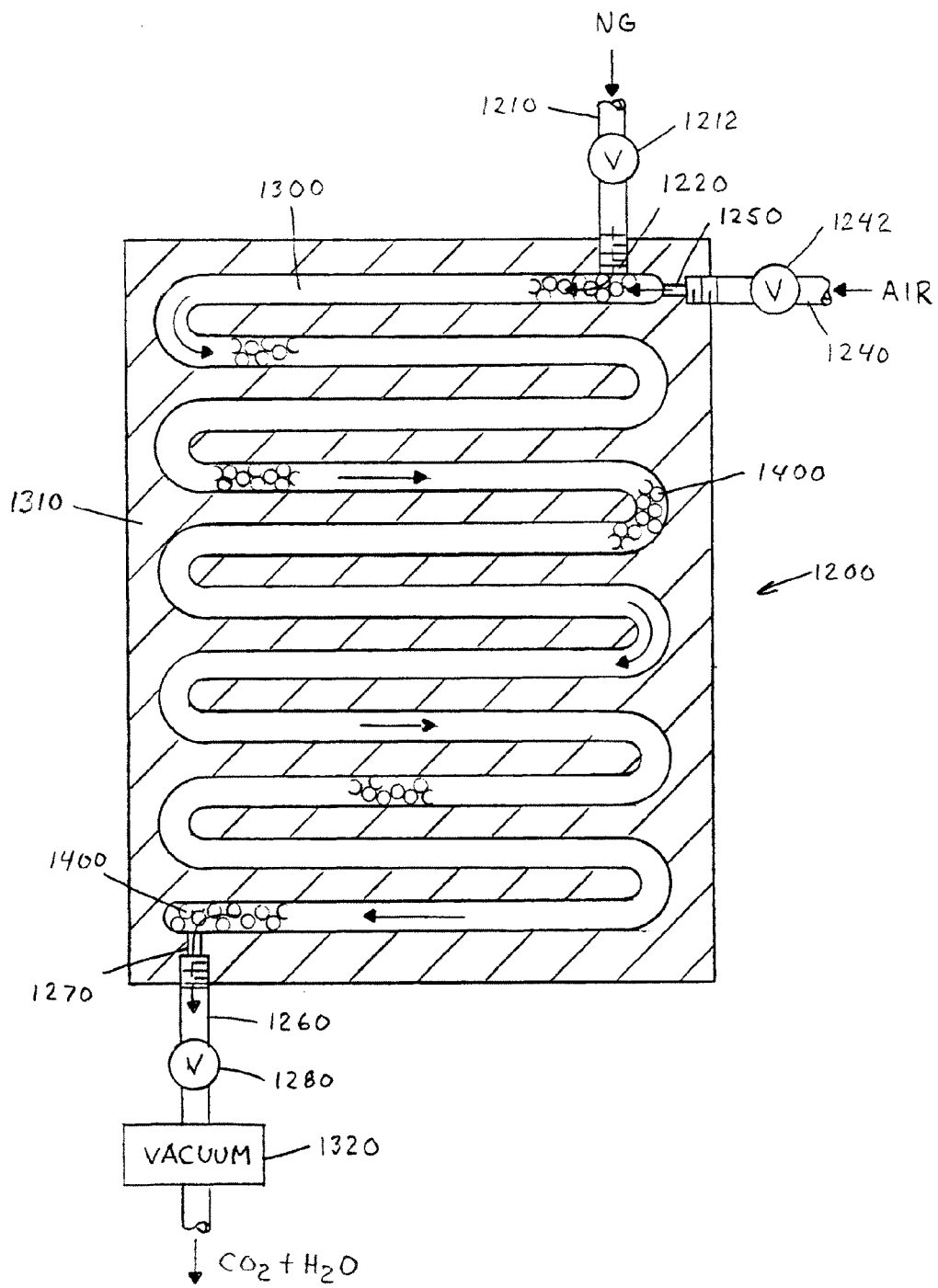
FIG. 14 is a cross-sectional view of yet another non-limiting processing apparatus of the present invention in the form of a furnace element.
Figure 15:
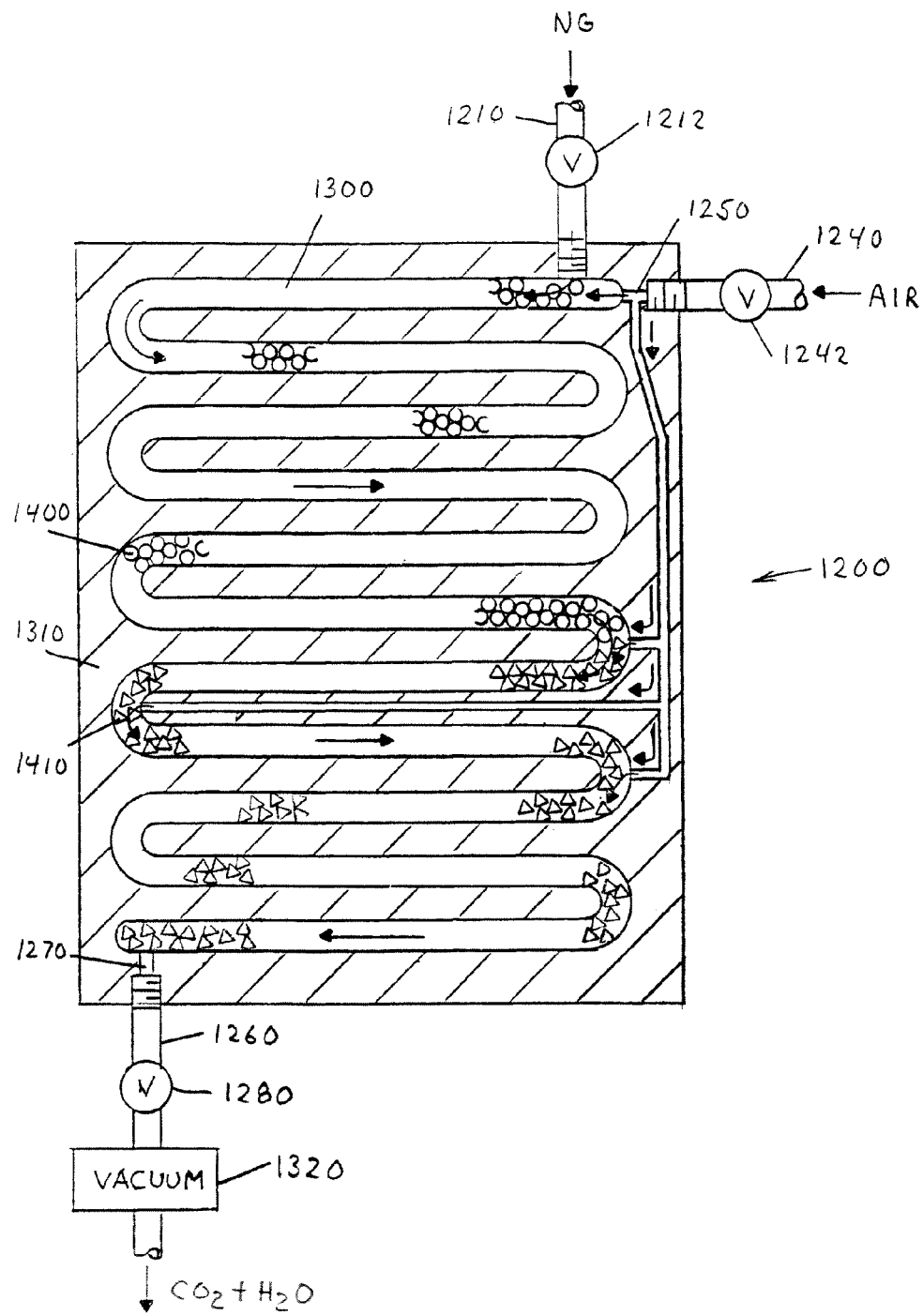
FIG. 15 is a cross-sectional view of another non-limiting processing apparatus of the present invention in the form of a furnace element.
Figure 16:
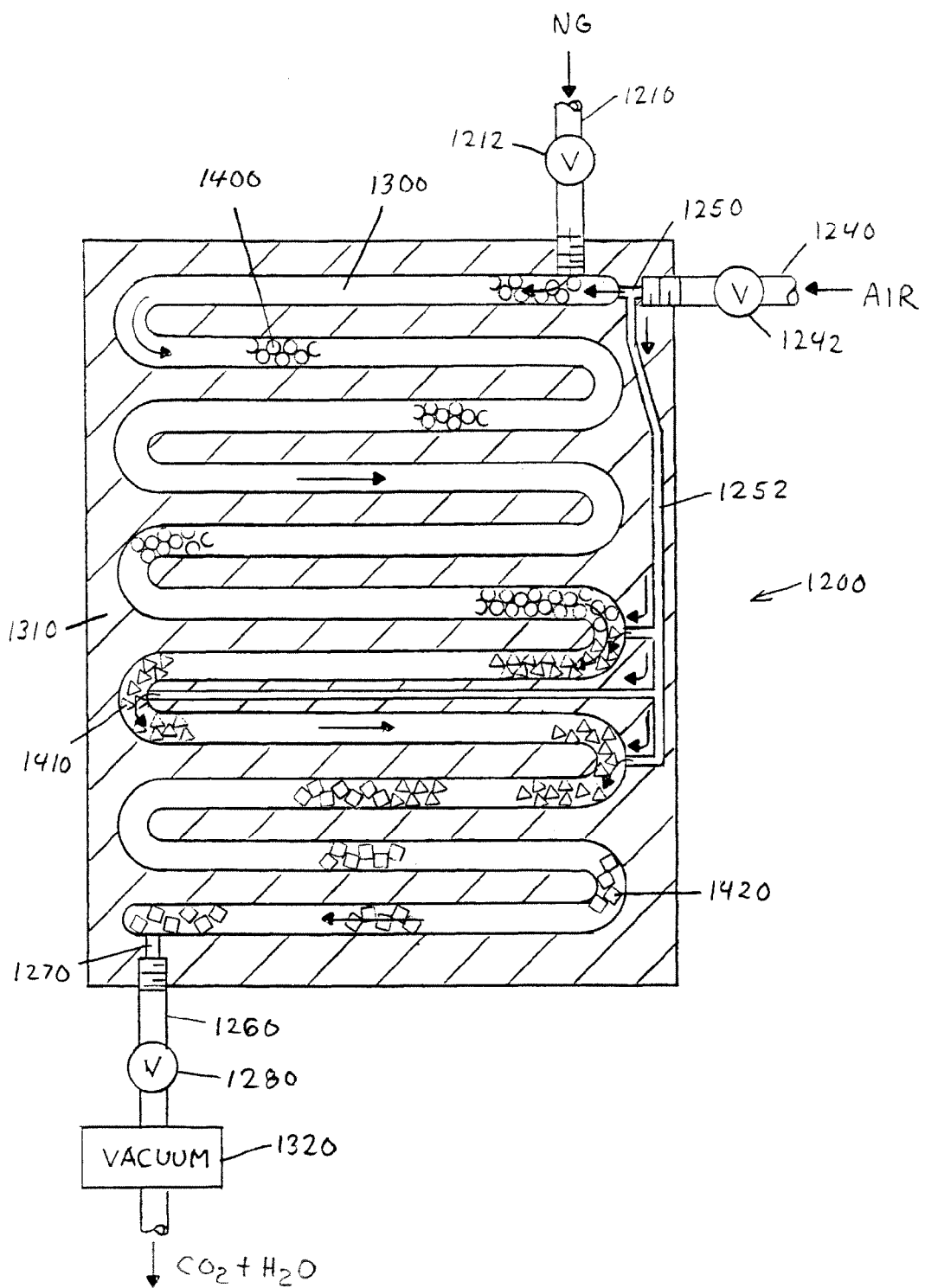
FIG. 16 is a cross-sectional view of still another non-limiting processing apparatus of the present invention in the form of a furnace element.

Referring now to FIGS. 14-16, one or more materials and/or catalysts can be inserted into one or more portions of the passageway of one or more furnace elements to 1) facilitate in the combustion of the natural gas in the one or more passageways of one or more furnace elements, 2) to at least partially control the rate of combustion of the natural gas in the one or more passageways of one or more furnace elements, 3) to convert one or more by-products of the combustion of the natural gas in one or more other compounds and/or elements in one or more passageways of one or more furnace elements, 4) at least partially improve the heat transfer into or out of one or more passageways of one or more furnace elements, and/or 5) to remove one or more impurities in the exhaust gas in one or more passageways of one or more furnace elements. The use of one or more catalysts in one or more passageways of one or more furnace elements can be used in the furnace elements described above with regard to FIGS. 9-13 and 21-22 and/or below with regard to FIGS. 17-20.

Referring now to FIG. 14, there is illustrated a cross-section of a portion of a furnace element 1200. As shown in FIG. 14, a natural gas pipe 1210 is connected to port 1220 and an air pipe 1240 is connected to port 1250. Pipe 1210 includes a valve 1212 to control the flow rate of natural gas NG into passageway 1300. Pipe 1240 also includes a valve 1242 to control the flowrate of air into passageway 1300. As can be appreciated, the inclusion or use of valve 1212 and/or valve 1242 is not required. The arrows included in passageway 1300 indicate the flow of gasses through passageway 1300. Passageway 1300 is at least partially formed in metal layer 1310. During the combustion of the natural gas in passageway 1300, carbon dioxide and water are formed. An exhaust pipe 1260 is connected to port 1270. A valve 1280 is connected to pipe 1260 to control the flowrate of gasses exiting the furnace element. As can be appreciated, valve 1280 is not required. A vacuum pump 1320 or other type of device is illustrated as being in fluid connection with pipe 1260 so as to pull a vacuum on pipe 1260. The vacuum on pipe 1260 can be used to increase the pressure drop through the passageway 1300 of the furnace element so as to facilitate in the flow of gasses through the passageway. The amount of vacuum applied to pipe 1260 can be controlled and/or set to at least partially adjust the flowrate of gasses though the passageway 1300 of furnace element 1200; however, this is not required.

Although not shown, metal layer 1310 can be laminated to one or more other metal layers; however, this is not required. When a laminate is used, the laminate can be an adhesive and/or a brazing metal; however, this is not required. The laminate, when used, generally depends on the composition of metal layers that form the furnace element and the temperature of operation of the furnace element. The metal layers can be formed of the same or different material. The types of metal for the metal layers, the type of adhesive, and/or the type of brazing metal can be the same or different from the materials discussed above with regard to furnace element 300 of FIGS. 9-13. The thickness of the metal layers in furnace element 1200 can depend in part on 1) the number of metal layers used to form the furnace element and 2) the size and design of the furnace element. Non-limiting examples of brazing metals that can be used include, but not limited to, silver, silver-brass, silver-tin, silver-nickel, lead-tin, nickel-brass, or nickel. Non-limiting examples for the metal used in the metal layers includes, but is not limited to, aluminum, aluminum alloys, copper, copper alloys, carbon steel and/or stainless steel; however, it will be appreciated that other metals can also be used. As can also be appreciated, many of thickness can be used for metal layers that are used to for the furnace element. As can be appreciated, if furnace element is formed from thin metal layers, then the average thickness of the metal layers will typically be less and the number of metal layers used to form the furnace element will typically be greater. In addition, if thin metal layers are used, one or more of the metal layers can be formed of a plurality of thin metal layers that have been laminated together; however, this is not required. Metal layer 1200 is illustrated as having a shape of a generally rectangular prism; however, it can be appreciated that one or more of the metal layers used to form the furnace element can have other shapes.

As shown in FIG. 14, a single passageway 1300 serpentines through the furnace element 1200. As can be appreciated, more than one passageway can exist in the furnace element. As also can be appreciated, passageway paths other than or in addition to a serpentine passageway can be used. If the furnace element includes two or more passageways, the passageways can have the same or different shaped pathways. Passageway 1300 is illustrated as having a generally circular cross-sectional shape; however, it can be appreciated that other or additional cross-sectional shapes (e.g., polygonal, oval etc.) can be used in one or more portions of the passageway. Passageway 1300 is illustrated has having a generally constant cross-sectional size and shape along the length of the passageway; however, this is not required.

As illustrated in FIG. 14, a catalyst 1400 or other type of material is located in one or more portions of passageway 1300. As shown in FIG. 13, catalyst 1400 is positioned throughout passageway 1300; however, it can be appreciated that less than about 90%, less than about 80%, less than about 70%, less than about 60%, less than about 50%, less than about 40%, less than about 30%, less than about 20% and/or less than about 10% of the passageway may include catalyst 1400. The catalyst in one or more portions of the passageway can have the same or different size and/or shape. In one non-limiting embodiment, the catalyst is designed to 1) improve and/or control the rate of combustion in one or more portions of the passageway, 2) at least partially convert carbon monoxide into carbon dioxide, and/or 3) remove nitrogen and/or sulfur compounds from the exhaust gas. As can be appreciated, the catalyst can have other or additional uses. One non-limiting catalyst or material that can be used to improve and/or control the rate of combustion in one or more portions of the passageway is a calcined alumina material. One non-limiting catalyst that can be used to at least partially convert carbon monoxide into carbon dioxide is a platinum-alumina based catalyst.

Referring now to FIGS. 15 and 16, the furnace element is shown to include more than one type of catalyst in passageway 1300. As illustrated in FIG. 15, two catalysts 1400 and 1410 are included in one or more portions of passageway 1300. Catalyst 1410 is positioned down stream from catalyst 1400. In one non-limiting arrangement, catalyst 1400 is designed to improve and/or control the rate of combustion in one or more portions of the passageway, and catalyst 1410 is designed to at least partially convert carbon monoxide into carbon dioxide, and/or remove nitrogen and/or sulfur compounds from the exhaust gas. In another non-limiting arrangement, catalyst 1400 is designed to improve and/or control the rate of combustion in one or more portions of the passageway and/or at least partially convert carbon monoxide into carbon dioxide, and catalyst 1410 is designed to remove nitrogen and/or sulfur compounds from the exhaust gas. As illustrated in FIG. 16, three catalysts 1400, 1410 and 1420 are included in one or more portions of passageway 1300. Catalyst 1410 is positioned down stream from catalyst 1400, and catalyst 1420 is positioned downstream from catalyst 1410. In one non-limiting arrangement, catalyst 1400 is designed to improve and/or control the rate of combustion in one or more portions of the passageway, catalyst 1410 is designed to at least partially convert carbon monoxide into carbon dioxide, and catalyst 1420 is designed to remove nitrogen and/or sulfur compounds from the exhaust gas. Although one, two or three catalysts are disclosed in passageway 1300, it can be appreciated that more than three catalysts can be included in passageway 1300. As also can be appreciated, one, two, three, four and five specific functions of the catalysts were disclosed; however, it can be appreciated that more than five functions of the catalyst can occur in the passageway.

Referring again to FIGS. 15 and 16, additional air passageways 1252 are illustrated. For example, when at least partially converting carbon monoxide into carbon dioxide, and/or removing nitrogen and/or sulfur compounds from the exhaust gas, and additional oxygen and/or nitrogen source may be required. Passageways 1252 can be used to provide air and/or other types of fluids to one or more regions of the passageway.

Referring now to FIGS. 17-20, there is illustrated another non-limiting arrangement of a processing apparatus in accordance with the present invention. This processing apparatus will also be described as a furnace element 400; however, it will be appreciated that the processing apparatus can be used as a reactor, micro-reactor, heat exchanger, etc. Although furnace element 400 has a different configuration from furnace element 300 illustrated in FIGS. 9-16 and 21-22, it will be appreciated that furnace element 400 can be designed to include valves, additional ports, port connection arrangements, port mixers, scrubbers, vacuum devices, catalysts, heat fins and/or micro-reactors; however, this is not required. As also can be appreciated, furnace element 400 can be connected to a plurality of furnace elements 400, and/or other furnace elements as described above with regard to FIGS. 13 and 21; however, this is not required. Furthermore, it can be appreciated that furnace element 400 can be used in combination with a fluid cooling arrangement as described above with regard to FIGS. 21 and 22; however, this is not required.

As illustrated in FIGS. 17-20, furnace element 400 is formed of a plurality of metal layers 402, 404 that are laminated together by a laminate 410. The lamination can be the form of a high temperature adhesive a brazing metal, etc. The laminate used generally depends on the composition of metal layers 402, 404 and the temperature of operation of the furnace element. The metal layers can be formed of the same or different material. The types of metal for the metal layers, the type of adhesive, and/or the type of brazing metal can be the same or different from the materials discussed above with regard to furnace element 300 of FIGS. 9-11. The thickness of the metal layers in furnace element 400 can depend in part on 1) the number of metal layers used to form the furnace element and 2) the size and design of the furnace element. As illustrated in FIGS. 17-20, the furnace element is formed of nine (9) layers; however, it can be appreciated that a larger or smaller number of metal layers can be used to form the furnace element. For the furnace element illustrated in FIGS. 17-20, the furnace element is for home use and has a volume of less than about 1200 cubic inches. As can be appreciated, larger or smaller furnace elements can be used. As also can be appreciated, the furnace element can be other sizes for non-home use (e.g., commercial use, etc.). For the furnace element for home use that has a volume of less than about 1200 cubic inches, the average thickness of the furnace element is about 0.2-5 inches (5080-127,000 microns), and generally about 0.4-2 inches (10160-50800 microns); however, other average thicknesses can be used. The metal layers 402, 404 are illustrated as having different thickness; however, this is not required. Generally the thickness of metal layer 404 is at least about 25% greater than the thickness of metal layer 402. In one non-limiting arrangement, the average thickness of metal layer 404 is about 0.1-3 inches (2540-76,200 microns), typically about 0.2-1.5 inches (5080-38,100 microns), and even more typically about 0.25-0.75 inch (6350-15,050 microns). In another non-limiting arrangement, the average thickness of metal layer 404 is about 0.05-2 inches (1270-50800 microns), typically about 0.075-1 inch (1905-25400 microns), and more typically about 0.08-0.5 inch (2032-12,700 microns). As can be appreciated, many other thicknesses can be used for metal layers 402 and/or 404. As can be appreciated, if furnace element is formed from thin metal layers, then the average thickness of the metal layers will typically be less and the number of metal layers used to form the furnace element will typically be greater. In addition, if thin metal layers are used, metal layers 404 and/or 402 may be formed of a plurality of thin metal layers that have been laminated together; however, this is not required. The metal layers are illustrated as having a shape of a generally rectangular prism; however, it can be appreciated that one or both of the metal layers can have other shapes.

Figure 17:
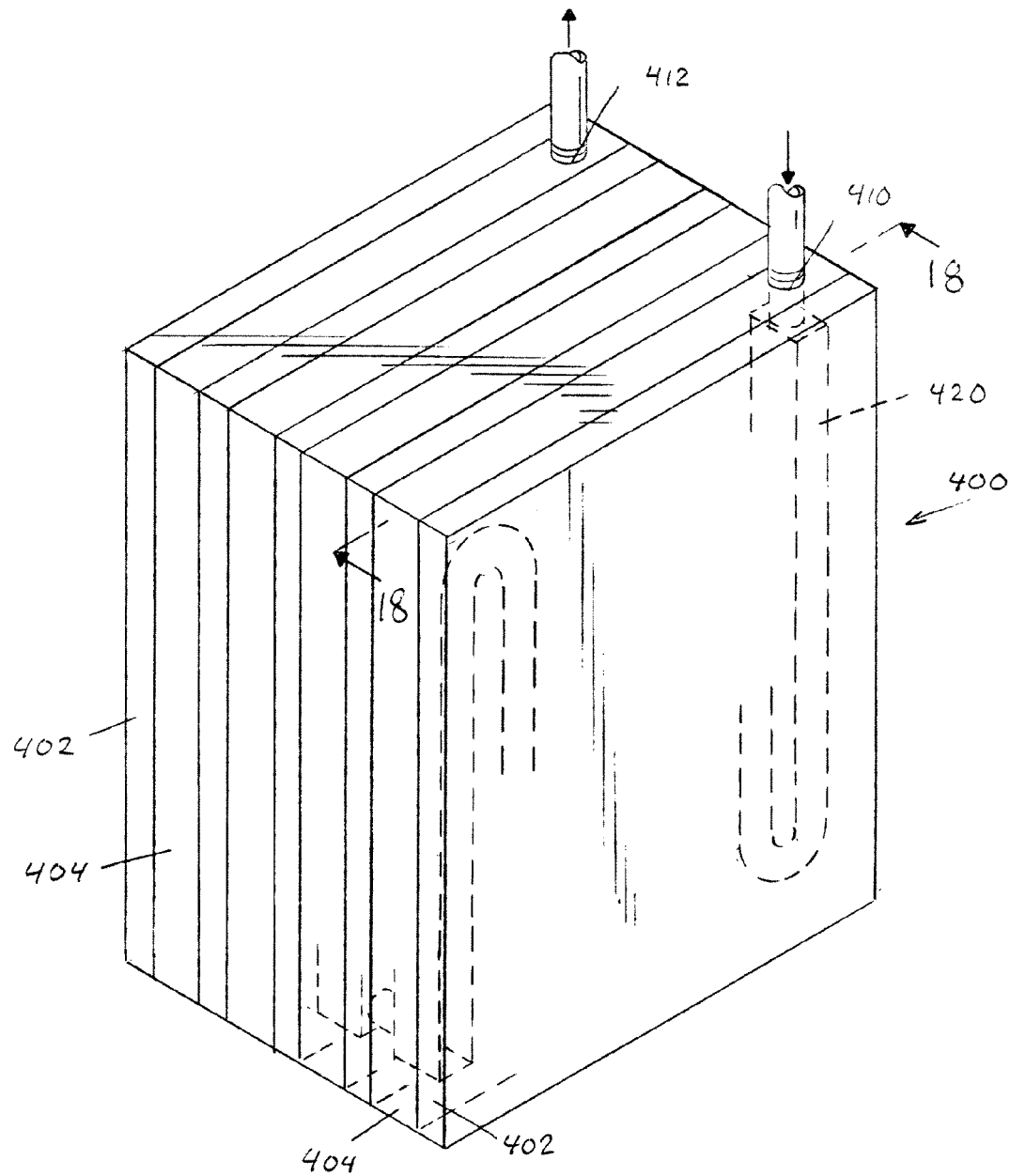
FIG. 17 is an elevation view of one non-limiting processing apparatus of the present invention that can be used as a microreactor.
Figure 18:
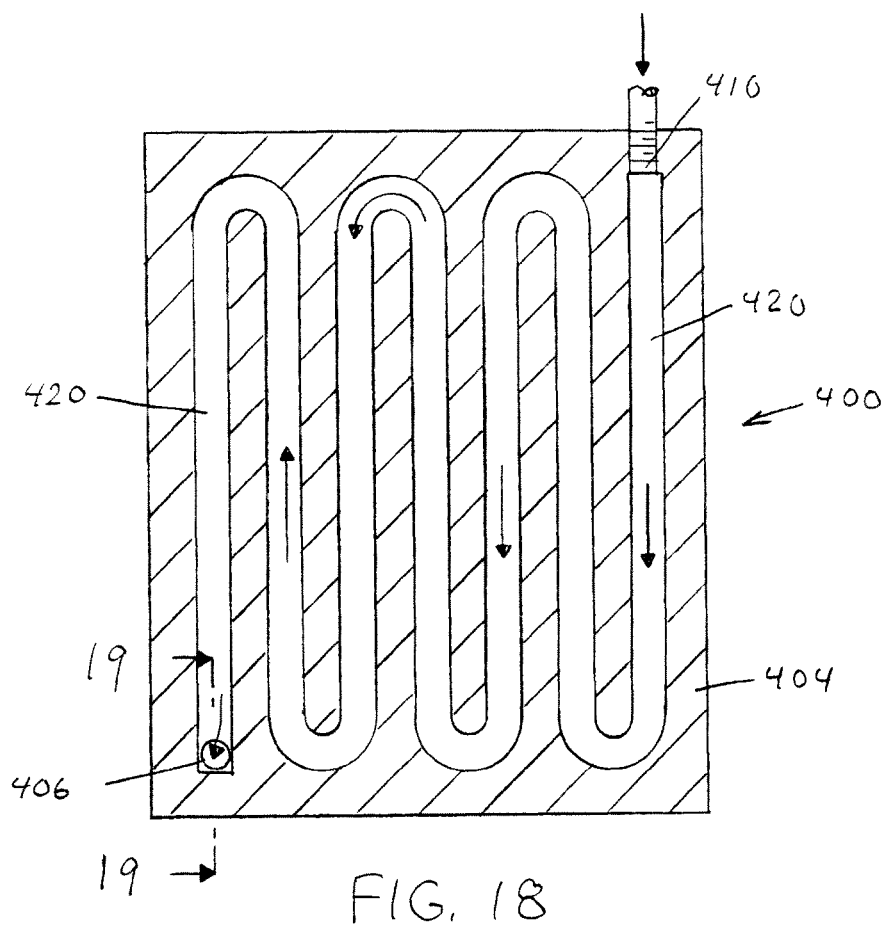
FIG. 18 is a cross-sectional view of the processing apparatus as illustrated in FIG. 17.

As best shown in FIG. 18, a single passageway 420 serpentines through the middle of the furnace element 400. As can be appreciated, more than one passageway can exist in the furnace element. As also can be appreciated, passageway paths other than or in addition to a serpentine passageway can be used. If the furnace element includes two or more passageways, the passageways can have the same or different shaped pathways. Passageway 420 is illustrated as having a generally rectangular cross-sectional shape as illustrated in FIG. 17-20; however, it can be appreciated that other or additional cross-sectional shapes (e.g., circular, other polygonal shapes, oval, etc.) can be used in one or more portions of the passageway. Passageway 420 is illustrated as having a generally constant cross-sectional size and shape along the length of the passageway; however, this is not required. For example, when one or more materials passing through the passageway increase or decrease in volume and/or pressure, the cross-sectional area of the passageway of one or more regions of the passageway can be adjusted to accommodate for such volume change.

As illustrated in FIG. 17, the furnace element 400 includes two ports 410, 412 that are in fluid communication with passageway 420. Port 410 can be used to connect to a natural gas source and/or oxygen source, or vice versa. Gas port 412 can be used to connect to an exhaust pipe to convey the combusted gasses from the furnace element. One or more of the ports can include connection arrangements to facilitate in connecting a pipe, tube, etc. to one or more of the ports; however, this is not required. As can also be appreciated, the furnace element can include a greater or lesser number of gas ports. For example, the natural gas and air and/or oxygen can separate ports, thus the furnace element would have at least three ports. In another example, one or more ports can be positioned downstream from the combustion region to introduce one or more fluids into the passageway and/or to remove combusted gasses from one or more of the passageways. As can be appreciated, many number of different arrangements for ports and port locations on the furnace element can be used. One or more mixing elements can be included in one or more of the ports and/or in passageway 420 to facilitate in the mixing of the gasses in the furnace element; however, this is not required.

Referring again to FIG. 20, metal layer 420 includes a groove or channel portion 422 that traverses the complete thickness of metal layer 404. Metal layers 402 are illustrated as not including and channels or grooves. When metal layers 402 are connected to each side of metal layer 404, passageway 420 is formed. As can be appreciated, many other or additional arrangements can be used to form one or more portions of passageway 420. For example, metal layer 404 can include a channel or groove that is less than the thickness of the metal layer. In another example, metal layer 402 can include a slot or groove that is used to at least partially form passageway 420.

Figure 19:
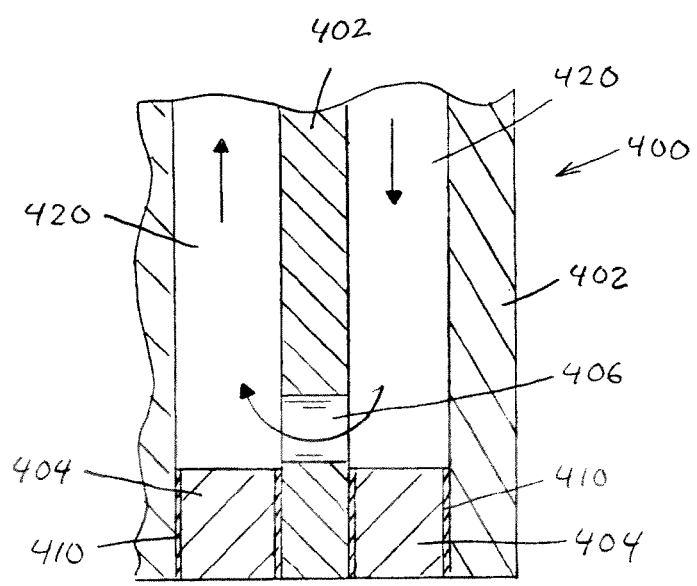
FIG. 19 is a cross-sectional view along line 19-19 of FIG. 18.

As illustrated in FIGS. 17, 19 and 20, at least one metal layer 402 includes passage opening 406. As also illustrated in FIGS. 17 and 20, the outer layer of the furnace element that is each formed by metal layer 402 does not include an opening 406; however, this is not required. Opening 406 is designed to create a fluid connection between the channel or groove in metal layers 404. As such, when the metal layers are assembled together, materials are able to flow into port 410 and out port 412 as indicated by the arrows in FIGS. 18-20. As can be appreciated, the location of openings 406 is non-limiting, thus any conceivable flow pattern through the furnace element can be created, and all such flow patterns are encompassed by this invention. Opening 406 is illustrated as being a generally circular opening; however, other opening shapes can be used.

As can be appreciated, although the processing apparatus illustrated in FIGS. 17-20 was described as a furnace element, the processing apparatus could have other uses such as, but not limited to a reactor or micro-reactor, heat exchanger, etc. As can also be appreciated, materials other than or in addition to gasses can be flowed through the processing apparatus (e.g., liquids, liquid and solid mixtures, gas and liquid mixtures, etc.).

Referring now to FIGS. 23-25, there are illustrated three non-limiting fluid mixing devices 1500, 1510, 1520. These three devices can be used to facilitate in the mixing of two or more fluids in one or more passageways of the processing apparatus. These three devices can be used to facilitate in alternating the flow pattern of one or more fluids in one or more passageways of the processing apparatus. These three devices can be incorporated in the processing apparatus and/or be positioned so as to affect one or more fluids flowing into and/or out of one or more passageways of the processing apparatus. The mixing and/or alternation of fluid flow patterns in one or more portions of one or more passageways of the processing apparatus can be used to, but not limited to, 1) positively affect desired heat transfer rates, 2) improve and/or control reaction and/or combustion rates of one or more fluids, and/or 3) obtained desired flow fluid patterns and/or fluid mixing rates. As can be appreciated, the fluid mixing devices can do other or different functions. When more than one fluid mixing device is used, the fluid mixing devices can have the same or different size and/or shape. As mentioned above, the fluid mixing devices are examples of just a few of the fluid mixing devices that can be used in the present invention.

Referring now to FIG. 23, fluid mixing device 1500 includes a central cavity 1502 that can be connected at one side to a pipe P and/or passageway of a processing apparatus. The outer surface 1504 of the fluid mixing devices includes a plurality of arcuate fins 1506. As can be appreciated, the number of fins, the size of the fins and/or shape of the fins can be varied. In this arrangement, one or more fluids flow through pipe P and through central cavity 1502. In addition, one or more fluids also flow past fins 1506. The one or more fluids that flow through cavity 1502 and past fins 1506 can be the same or different. The fluid pattern of the fluids flowing through cavity 1502 and past fins 1506 are different and generally result in rapid mixing of the fluids down stream from fluid mixing device 1500. Referring now to FIG. 24, fluid mixing device 1510 functions in a similar manner as the fluid mixing device illustrated in FIG. 23. The fin 1510 position and fin profile on fluid mixing device 1510 is different than fin position and fin profile on fluid mixing device 1500. As such, fluid mixing device 1510 includes a central cavity 1514 that can be connected at one side to a pipe and/or passageway, not shown. The outer surface 1516 of the fluid mixing devices includes a plurality of arcuate fins 1512.

Referring now to FIGS. 24-25, fluid mixing device 1520 has a partial cone-shape. The fluid mixing device 1520 includes a central cavity 1522 and has a tapering cross-sectional area. The fluid mixing device 1520 also includes an outer surface 1524 that is absent fins. The fluid can be designed to flow through the central cavity and/or about the outer surface of the fluid mixing device. Although the outer surface and the surface of the central cavity are illustrated as being smooth, one or both surfaces can include grooves, ridges, and the like.

Although the apparatus and method of the present invention has been particularly directed to the manufacture of processing apparatus such a micro-reactors and furnace elements, the technology of the present invention can be used in other fields of use. Among the many conceivable fields of use, technology areas, and devices which can utilize the method of manufacture of the present invention include, but are not limited to, the automotive industry in the fields of inertial measurement, micro-scale power generation, pressure measurement, fluid dynamics and the like (e.g., accelerometers, rate sensors, vibration sensors, pressure sensors, fuel cells, fuel processors, nozzle technology, valves and regulators, pumps, filters, catalytic converters, relays, actuators, heaters, etc.), the avionics industry in the fields of inertial measurement, RF technology, communications, active structures and surfaces and the like (e.g., conformable MEMS (active and passive), micro-satellite components, micro-thrusters, RF switches, antennas, phase shifters, displays, optical switches, accelerometers, rate sensors, vibration sensors, pressure sensors, fuel cells, fuel processors, nozzle technology, valves and regulators, pumps, filters, relays, actuators, heaters, rocket engines and/or other propulsion systems, etc.), the biological, biotechnology and chemical industry in the fields of microfluidics, microbiology, DNA assays, chemical testing, chemical processing other than the use of micro-reactors, lab-on-a-chip, tissue engineering, analytical instrumentation, bio-filtration, test and measurement, bio-computing, biomedical imaging and the like (e.g., biosensors, bioelectronic components, reaction wells, microtiterplates, pin arrays, valves, pumps, microwells and microwell arrays, microvalves, micropumps, valve seats, valve actuators (diaphragm), cavity chamber, actuator diaphragm, bio-filters, SEM, EDS, ICP, x-ray mapping, x-ray crystallography, tissue scaffolding, screens, filters, microscopes, cell sorting and filtration membranes, etc.), the medical (diagnostic and therapeutic) industry in the fields of imaging, computed tomography, angiography, fluoroscopy, radiography, interventional radiography, orthopedic, cardiac and vascular devices, catheter based tools and devices, non-invasive surgical devices, medical tubing, fasteners, surgical cutting tools and the like (e.g., airways, balloon catheters, clips, compression bars, stents, drainage tubes, ear plugs, microwells and microwell arrays, microvalves, micropumps, drug delivery chips, microwell detectors, gas proportional counters, valve seats, valve actuators (diaphragm), cavity chamber, actuator diaphragm, hearing aids, electrosurgical hand pieces and tubing, feeding devices, balloon cuffs, wire/fluid coextrusions, lumen assemblies, infusion sleeves/test chambers, introducer tips/flexible sheaths, seals/stoppers/valves, septums, shunts, implants prosthetic devices, membranes, electrode arrays, ultra-sound transducers infra-red radiation sensors, radiopaque targets or markers, scatter grids, detector arrays, etc.), the military industry in the fields of weapon safeing, arming and fusing, miniature analytical instruments, biomedical sensors, inertial measurement, distributed sensing and control, information technology and the like (e.g., MEMS fuse/safe-arm devices, ordinance guidance and control devices, gyroscopes, accelerometers, GPS, disposable sensors, spectrometers, active MEMS surfaces (large area), micro-mirror MEMS displays, etc.), the telecommunications industry in the fields of optical switches, displays, adaptive optics, and the like (e.g., micro-relays, optical attenuators, photonic switches, micro-channel plates, optical switches, displays, etc.), the energy industry (e.g., fuel cells, solar cells, automotive fuel production from natural gas, methane processing, methanol production, ethylene production, catalytic cracking of petroleum products, production of alcohols from natural gas, coal gasification processes, hydrogenation processes [e.g., fats and/or oils hydrogenation, etc.], etc.), the environmental industry (e.g., pollution and/or waste control systems, landfill gas processing, methanol production from $CO_2$, reduction of $NO_x$ and/or $SO_x$ gasses, water purification systems, etc.), the heat exchange industry, and/or the extrusion industry (e.g., die plates, die insert, auger blades, wiper blades, etc.). As can be appreciated, many other devices can be made by the manufacturing process of the present invention.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

I claim:

1. A processing apparatus designed to combust natural gas and to convert at least one by product of the combusted natural gas into a liquid alcohol, said processing apparatus comprising a plurality of metal layers, at least two of said metal layers including an opening, said opening spaced from an outer edge of said at least two metal layers, said openings of adjacently positioned metal layers forming at least one fluid channel through said metal layers that is designed to enable fluid to flow through the at least one fluid channel when said metal layers are connected together, at least two of said metal layers stacked and aligned together and connected together by at least one metal laminate, a plurality, of said metal layers have an average thickness of up to about 1000 microns, a plurality of said metal layers including at least one alignment structure, said aligned structure spaced from said opening in said metal layer and not forming said at least one fluid channel, said alignment structure positioned in substantially the same location on each of said plurality of said metal layers, at least one of said metal layers functions as a catalyst metal to fluid flowing through said opening in said metal layer.

2. The processing apparatus as defined in claim 1, wherein said metal laminate has a different composition from said plurality of said metal layers, said metal laminate having a melting temperature of at least 10° C. less than said metal layer said metal laminate is coated thereon.

3. The processing apparatus as defined in claim 2, including at least one catalyst in said at least one fluid channel, said catalyst formed of a different composition from at least one of said metal layers.

4. The processing apparatus as defined in claim 3, wherein a plurality of said metal layers are formed by a process of generating electronic representations of a plurality of metal layers, and forming a plurality of metal layers into specific shapes based on said electronic representation of said metal layers.

5. The processing apparatus as defined in claim 4, wherein a plurality of said metal layers are at least partially formed by at least one lithographic technique.

6. The processing apparatus as defined in claim 5, including first and second cavities that are connected together, each of said cavities including a plurality of metal layers that are connected together, each of said cavities having a fluid opening to enable fluid to flow into and out of said at least one fluid channel.

7. The processing apparatus as defined in claim 6, wherein said processing apparatus includes a) a furnace portion and b) a reactor or micro-reactor portion, said furnace portion designed to combust natural gas, said reactor or micro-reactor designed to convert at least one by product of said combusted natural gas into a liquid alcohol, said furnace portion and said reactor or micro-reactor portion fluidly connected together.

8. The processing apparatus as defined in claim 1, wherein said plurality of metal layers forming a plurality of fluid channels when said metal layers are connected together.

9. The processing apparatus as defined in claim 2, wherein said metal plurality of metal layers forming a plurality of fluid channels when said metal layers are connected together.

10. The processing apparatus as defined in claim 9, wherein said plurality of fluid channels are fluidly connected together during or after the fluid flows through said plurality of said metal layers.

11. The processing apparatus as defined in claim 10, including first and second cavities that are connected together, each of said cavities including a plurality of metal layers that are connected together, each of said cavities having a fluid opening to enable fluid to flow into and out of said at least one fluid channel.

12. The processing apparatus as defined in claim 11, wherein said processing apparatus includes a) a furnace portion and b) a reactor or micro-reactor portion, said furnace portion designed to combust natural gas, said reactor or micro-reactor designed to convert at least one by product of said combusted natural gas into a liquid alcohol, said furnace portion and said reactor or micro-reactor portion fluidly connected together.

13. A processing apparatus designed to combust natural gas and to convert at least one by product of the combusted natural gas into a liquid alcohol, said processing apparatus comprising a plurality of metal layers, at least two of said metal layers including an opening, said opening spaced from outer edge of said at least two metal layers, said openings of adjacently positioned metal layers forming at least one fluid channel through said metal layers that is designed to enable fluid to flow through the at least one fluid channel when said metal layers are connected together, at least two of said metal layers stacked and aligned together and connected together by at least one metal laminate, a plurality of said metal layers have an average thickness of up to about 1000 microns, a plurality of said metal layers including at least one alignment structure, said aligned structure spaced from said opening in said metal layer and not forming said at least one fluid channel, said alignment structure positioned in substantially the same location on each of said plurality of said metal layers, said metal plurality of metal layers forming a plurality of fluid channels when said metal layers are connected together, said plurality of fluid channels are fluidly connected together during or after the fluid flows through said plurality of said metal layers.

14. The processing apparatus as defined in claim 13, including first and second cavities that are connected together, each of said cavities including a plurality of metal layers that are connected together, each of said cavities having a fluid opening to enable fluid to flow into and out of said at least one fluid channel.

15. The processing apparatus as defined in claim 14, wherein said processing apparatus includes a) a furnace portion and b) a reactor or micro-reactor portion, said furnace portion designed to combust natural gas, said reactor or micro-reactor designed to convert at least one by product of said combusted natural gas into a liquid alcohol, said furnace portion and said reactor or micro-reactor portion fluidly connected together.

16. A processing apparatus designed to combust natural gas and to convert at least one by product of the combusted natural gas into a liquid alcohol, said processing apparatus comprising a plurality of metal layers, at least two of said metal layers including an opening, said opening spaced from an outer edge of said at least two metal layers, said openings of adjacently positioned metal layers forming at least one fluid channel through said metal layers that is designed to enable fluid to flow through the at least one fluid channel when said metal layers are connected together, at least two of said metal layers stacked and aligned together and connected together by at least one metal laminate, a plurality of said metal layers have an average thickness of up to about 1000 microns, a plurality of said metal layers including at least one alignment structure, said aligned structure spaced from said opening in said metal layer and not forming said at least one fluid channel, said alignment structure positioned in substantially the same location on each of said plurality of said metal layers, and including first and second cavities that are connected together, each of said cavities including a plurality of metal layers that are connected together, each of said cavities having a fluid opening to enable fluid to flow into and out of said at least one fluid channel.

17. The processing apparatus as defined in claim 16, wherein said processing apparatus includes a) a furnace portion and b) a reactor or micro-reactor portion, said furnace portion designed to combust natural gas, said reactor or micro-reactor designed to convert at least one by product of said combusted natural gas into a liquid alcohol, said furnace portion and said reactor or micro-reactor portion fluidly connected together.

18. A processing apparatus designed to combust natural gas and to convert at least one by product of the combusted natural gas into a liquid alcohol, said processing apparatus comprising a plurality of metal layers, at least two of said metal layers including an opening, said opening spaced from an outer edge of said at least two metal layers, said openings of adjacently positioned metal layers forming at least one fluid channel through said metal layers that is designed to enable fluid to flow through the at least one fluid channel when said metal layers are connected together, at least two of said metal layers stacked and aligned together and connected together by at least one metal laminate, a plurality of said metal layers have an average thickness of up to about 1000 microns, a plurality of said metal layers including at least one alignment structure, said aligned structure spaced from said opening in said metal layer and not forming said at least one fluid channel, said alignment structure positioned in substantially the same location on each of said plurality of said metal layers, said processing apparatus includes a) a furnace portion and b) a reactor or micro-reactor portion, said furnace portion designed to combust natural gas, said reactor or micro-reactor designed to convert at least one by product of said combusted natural gas into a liquid alcohol, said furnace portion and said reactor or micro-reactor portion fluidly connected together.

* * * * *